(12) United States Patent
Gabbai et al.

(10) Patent No.: US 11,510,592 B2
(45) Date of Patent: Nov. 29, 2022

(54) SYSTEMS AND METHODS FOR NON-INVASIVE DETERMINATION OF COVID-19 CORONAVIRUS INFECTION

(71) Applicant: TERAHERTZ GROUP LTD., Herzliya (IL)

(72) Inventors: Eran Gabbai, Herzliya (IL); Yaniv Maydar, Tel Aviv (IL); Regina Aharonov-Nadborny, Beit Arye (IL)

(73) Assignee: Terahertz Group Ltd., Herzliya (IL)

( * ) Notice: Subject to any disclaimer, the term of this patent is extended or adjusted under 35 U.S.C. 154(b) by 74 days.

(21) Appl. No.: 17/206,870

(22) Filed: Mar. 19, 2021

(65) Prior Publication Data
US 2021/0275055 A1    Sep. 9, 2021

Related U.S. Application Data

(63) Continuation-in-part of application No. 16/749,611, filed on Jan. 22, 2020, and a continuation-in-part of
(Continued)

(30) Foreign Application Priority Data

Mar. 31, 2020    (IL) .......................................... 273709

(51) Int. Cl.
*A61B 5/08*       (2006.01)
*A61B 5/091*      (2006.01)
(Continued)

(52) U.S. Cl.
CPC .............. *A61B 5/082* (2013.01); *A61B 5/091* (2013.01); *A61B 5/097* (2013.01); *G01N 33/497* (2013.01); *G01N 2033/4975* (2013.01)

(58) Field of Classification Search
CPC ......... G01N 33/497; G01N 2033/4975; G01N 2021/775; G01N 21/3586; G01N 21/3581;
(Continued)

(56) References Cited

U.S. PATENT DOCUMENTS

| 4,594,226 A | 6/1986 | Reedy |
| 4,671,652 A | 6/1987 | van Asselt et al. |

(Continued)

FOREIGN PATENT DOCUMENTS

| CN | 108211807 A | 6/2018 |
| CN | 110487751 A | 11/2019 |

(Continued)

OTHER PUBLICATIONS

Cheng et al., "Terahertz biosensing metamaterial absorber for virus detection based on spoof surface plasmon polaritons", International Journal of RF And Microwave Computer-Aided Engineering, May 2018, pp. 1-7, 2018 Wiley Periodicals Inc.
(Continued)

*Primary Examiner* — Don K Wong
(74) *Attorney, Agent, or Firm* — Foley & Lardner LLP

(57) ABSTRACT

A high throughput method for label-free, noncontact, non-invasive, and nondestructive detection of at least one virus infected or virus free individual from at least one tested individual is provided. The method includes collecting a sample from exhaled breath of a subject for analysis of the sample. The collecting includes the subject exhaling into at least one sampler and collecting aerosols and/or any airborne compound from the exhaled breath by passing the exhaled breath through a metamaterial membrane within the sampler. The metamaterial membrane is arranged transverse to a flow of exhaled breath through the sampler. The method further includes analyzing the sample for detection of at least one virus infected individual from at least one tested individual.

40 Claims, 44 Drawing Sheets
(13 of 44 Drawing Sheet(s) Filed in Color)

Related U.S. Application Data application No. 16/321,261, filed on Jan. 28, 2019, now Pat. No. 11,006,617, which is a continuation-in-part of application No. PCT/IL2018/050814, filed as application No. PCT/US2017/044609 on Jul. 31, 2017.

(60) Provisional application No. 63/111,091, filed on Nov. 9, 2020, provisional application No. 63/111,089, filed on Nov. 9, 2020, provisional application No. 63/075,316, filed on Sep. 8, 2020, provisional application No. 63/075,324, filed on Sep. 8, 2020, provisional application No. 63/057,319, filed on Jul. 28, 2020, provisional application No. 63/057,318, filed on Jul. 28, 2020, provisional application No. 63/051,398, filed on Jul. 14, 2020, provisional application No. 63/051,399, filed on Jul. 14, 2020, provisional application No. 63/038,920, filed on Jun. 15, 2020, provisional application No. 63/038,921, filed on Jun. 15, 2020, provisional application No. 63/032,732, filed on Jun. 1, 2020, provisional application No. 63/032,735, filed on Jun. 1, 2020, provisional application No. 63/015,714, filed on Apr. 27, 2020, provisional application No. 63/015,723, filed on Apr. 27, 2020, provisional application No. 63/012,672, filed on Apr. 20, 2020, provisional application No. 63/012,682, filed on Apr. 20, 2020, provisional application No. 63/002,404, filed on Mar. 31, 2020, provisional application No. 63/000,007, filed on Mar. 26, 2020, provisional application No. 62/992,627, filed on Mar. 20, 2020, provisional application No. 62/960,159, filed on Jan. 13, 2020, provisional application No. 62/952,509, filed on Dec. 23, 2019, provisional application No. 62/904,405, filed on Sep. 23, 2019, provisional application No. 62/535,917, filed on Jul. 23, 2017, provisional application No. 62/368,623, filed on Jul. 29, 2016.

(51) Int. Cl.
*G01N 33/497* (2006.01)
*A61B 5/097* (2006.01)

(58) Field of Classification Search
CPC ....... G01N 2333/165; G01N 33/56983; G01N 2469/10
See application file for complete search history.

(56) References Cited

U.S. PATENT DOCUMENTS

| | | | |
|---|---|---|---|
| 4,955,728 | A | 9/1990 | Hebrank |
| 5,983,830 | A | 11/1999 | Cox et al. |
| 9,279,723 | B2 | 3/2016 | Roulston et al. |
| 2004/0107912 | A1 | 6/2004 | Hebrank |
| 2009/0091742 | A1 | 4/2009 | Hebrank et al. |
| 2010/0086750 | A1 | 4/2010 | Blumberg et al. |
| 2013/0023040 | A1 | 1/2013 | Phelps et al. |
| 2014/0283626 | A1 | 9/2014 | Mcmurtry et al. |
| 2015/0145435 | A1 | 5/2015 | Ogawa |
| 2016/0050891 | A1 | 2/2016 | Phelps et al. |

FOREIGN PATENT DOCUMENTS

| | | |
|---|---|---|
| DE | 10 2012 023 947 A1 | 6/2014 |
| JP | 2018-169165 A | 11/2018 |
| WO | WO-2011/143349 A1 | 11/2011 |
| WO | WO-2014/086335 A1 | 6/2014 |
| WO | WO-2015/145435 A1 | 10/2015 |
| WO | WO-2018/023105 A1 | 2/2018 |
| WO | WO-2019/021275 A1 | 1/2019 |
| WO | WO-2021191768 A2 * | 9/2021 |

OTHER PUBLICATIONS

Maier et al., "Toward Continuous Monitoring of Breath Biochemistry: A Paper-Based Wearable Sensor for Real-Time Hydrogen Peroxide Measurement in Simulated Breath", ACS Sensors, 2019, pp. 2945-2951, vol. 4, American Chemical Society.

Rothbart et al., "Analysis of Human Breath by Millimeter-Wave/Terahertz Spectroscopy", Sensors, 2019, pp. 1-12, vol. 19, No. 2719.

Rothbart et al., "Towards Breath Gas Analysis Based on Millimeter-Wave Molecular Spectroscopy", Frequenz, 2018, pp. 87-92, vol. 72, Nos. 3-4.

Sareen et al., "IoT-based cloud framework to control ebola virus outbreak", Journal of Ambient Intelligence and Humanized Computing, Oct. 20, 2016, 18 pages, Springer.

Van Der Schee et al., "Altered exhaled biomarker profiles in children during and after rhinovirus-induced wheeze", European Respiratory Journal, 2015, pp. 440-448, vol. 45.

Alessandra Costanzo et al., "The Odour of Sex: Sex-Related Differences in Volatile Compound Composition among Barn Swallow Eggs Carrying Embryos of Either Sex", PLOS ONE, Nov. 16, 2016, pp. 1-17, vol. 11, No. 11.

Ben Webster et al., "Avian Egg Odour Encodes Information on Embryo Sex, Fertility and Development", PLOS ONE, Jan. 28, 2015, pp. 1-10, vol. 19, No. 1.

International Search Report and Written Opinion of the International Searching Authority issued in International Application No. PCT/IL2018/050814 dated Oct. 25, 2018.

Konstantinos I. Diamantaras et al., "Principal Component Neural Networks: Theory and Applications." Wiley-Inter-science, New York, 1996 (Book Review), 1998 Springer-Verlag London Limited.

Notice of Allowance on U.S. Appl. No. 16/321,261 dated Dec. 30, 2020.

OSA Publishing Co., "Terahertz Volatile Gas Sensing by Using Polymer Microporous Membranes", https://www.osapublishing.org, pp. 1-19 (2020).

P. C. Mahalanobis, "On the generalized distance in statistics.", Proceeding of the National Institute of Sciences of India, Apr. 15, 1936, pp. 49-55, vol. II, No. 1.

R. A. Fisher, "The Use of Multiple Measurements in Taxonomic Problems", Annals of Eugenics, 7 Part II, 1936, pp. 179-188.

* cited by examiner

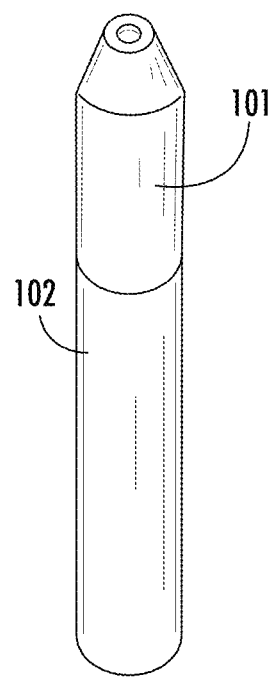
FIG. 1C
 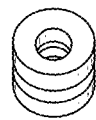 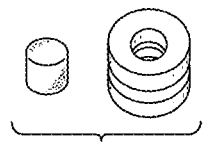 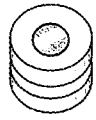
FIG. 1D    FIG. 1E    FIG. 1F    FIG. 1G

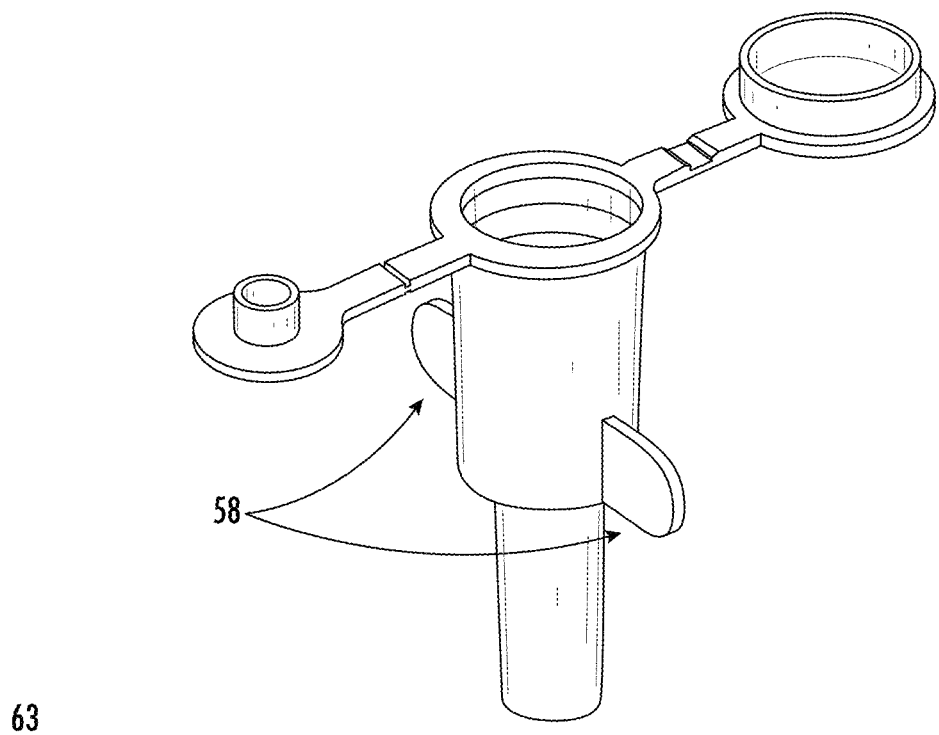
FIG. 5F
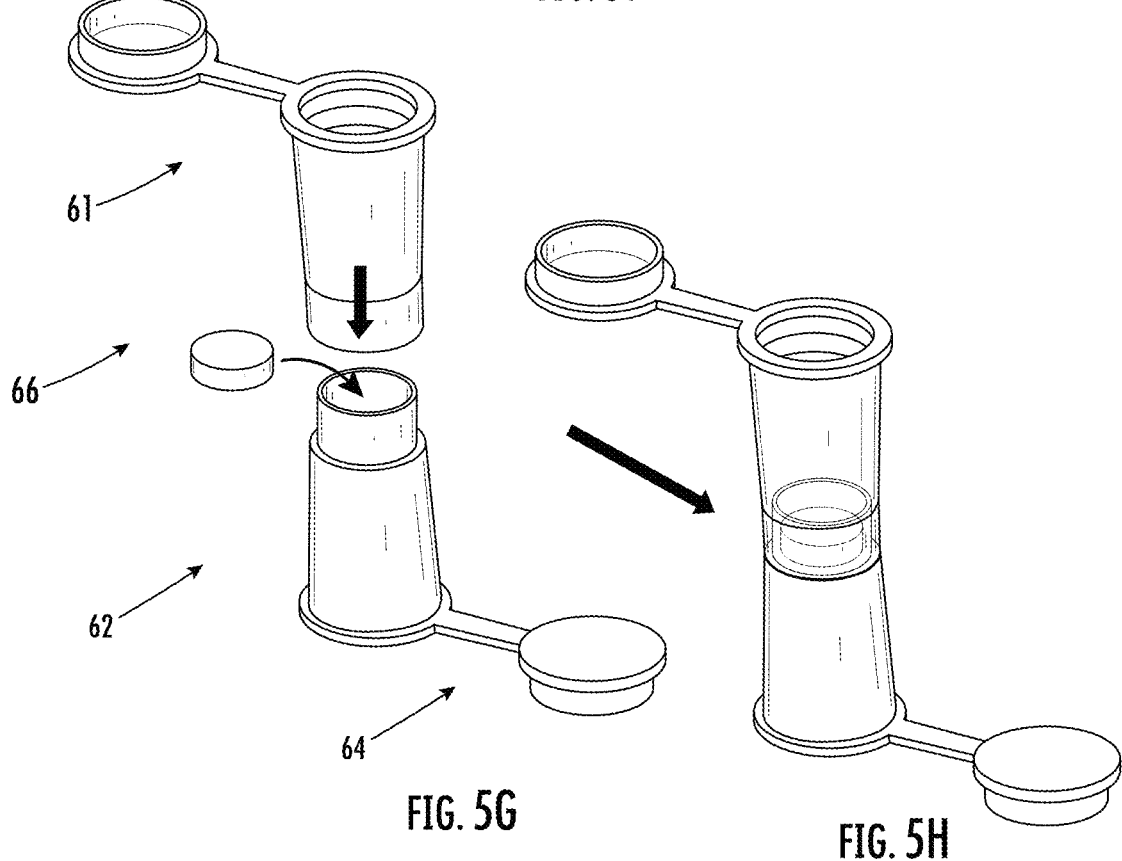
FIG. 5G
FIG. 5H

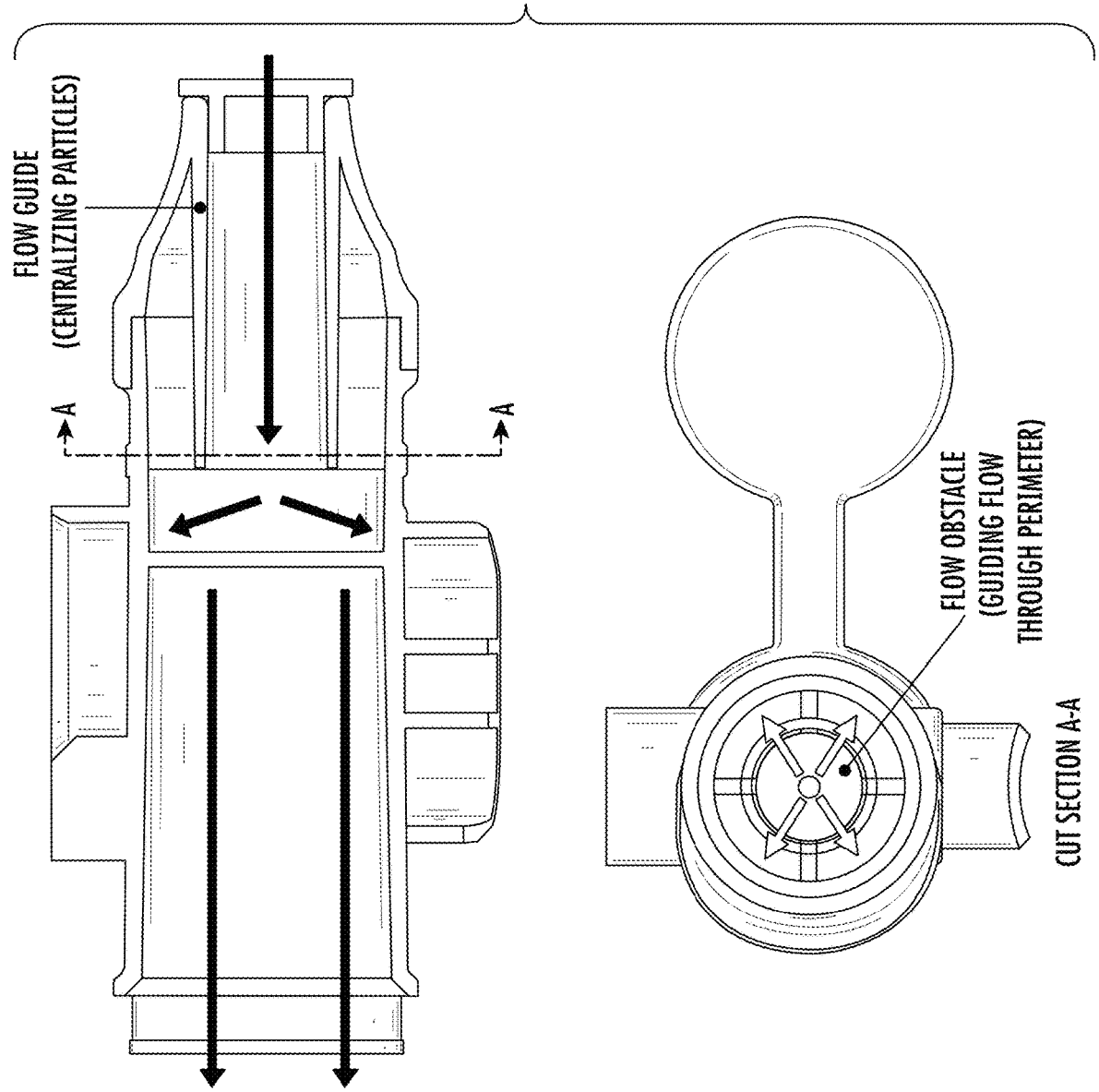

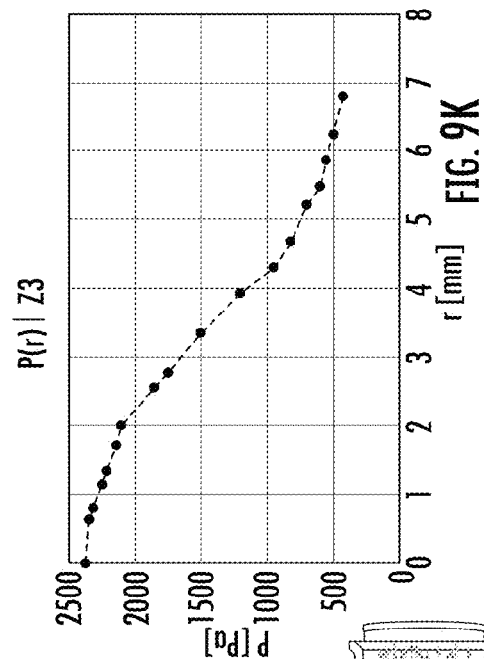
FIG. 9K
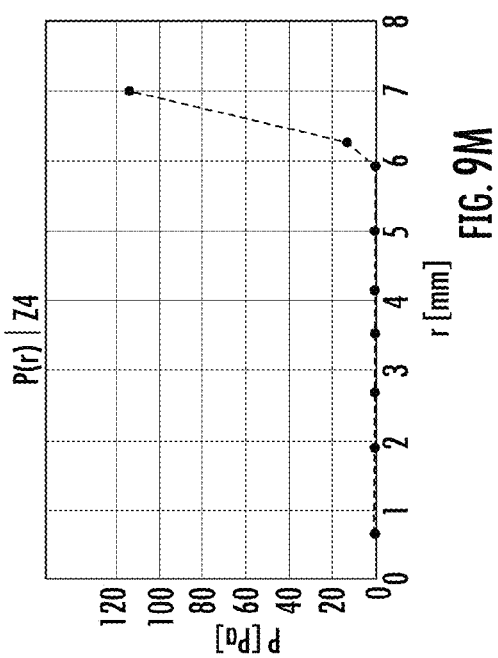
FIG. 9M
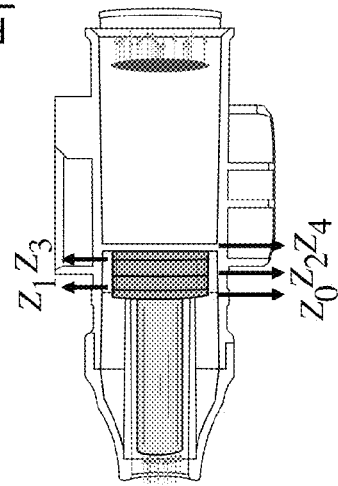
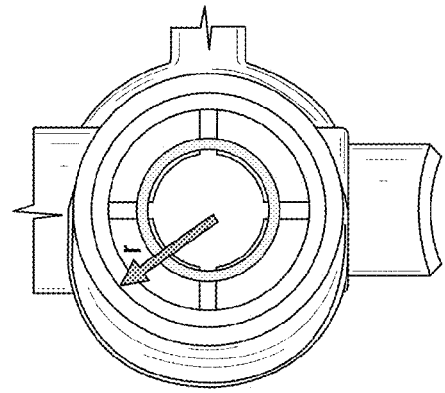
FIG. 9I
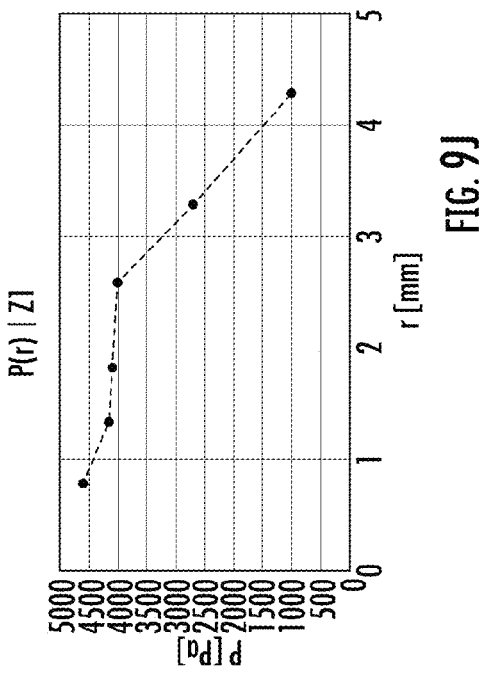
FIG. 9J
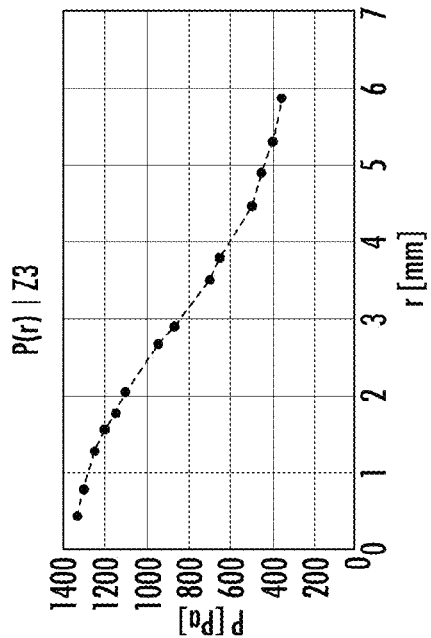
FIG. 9L

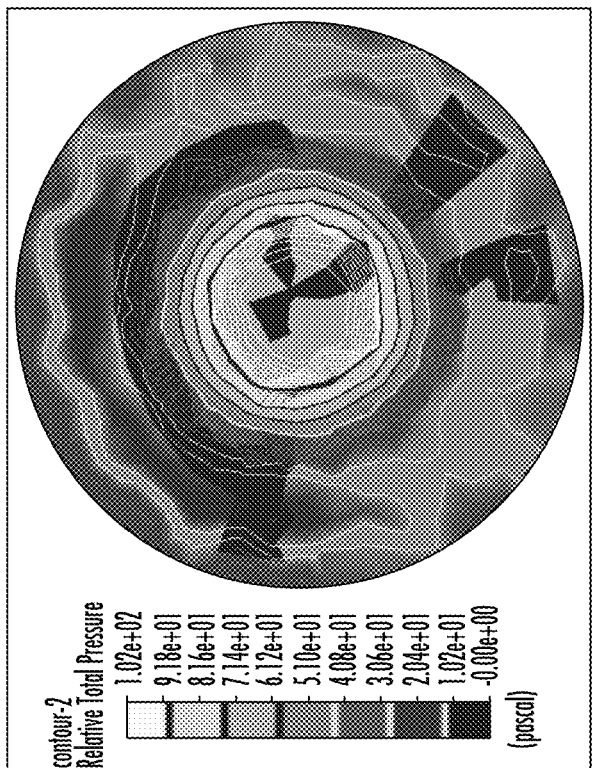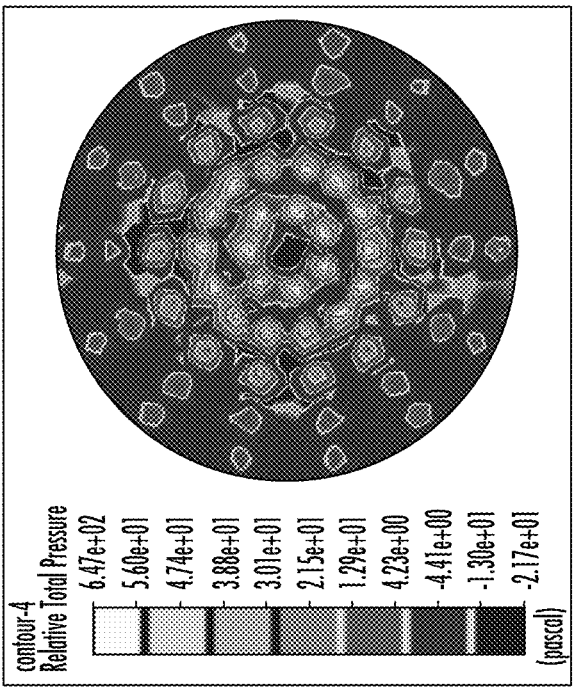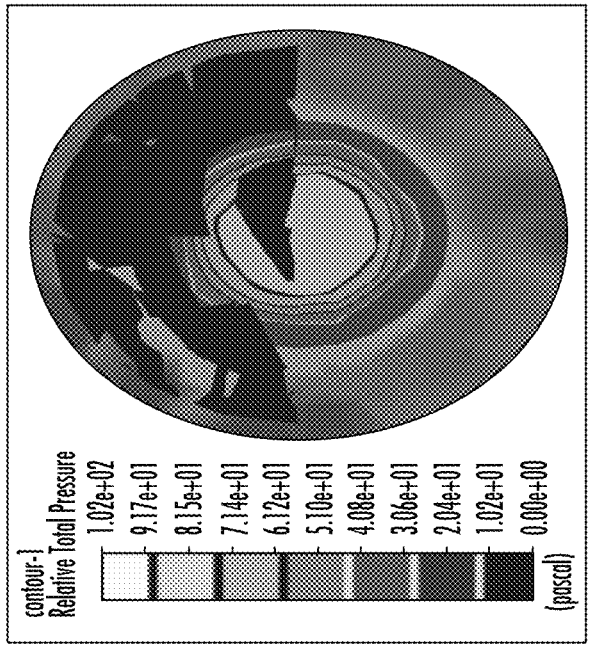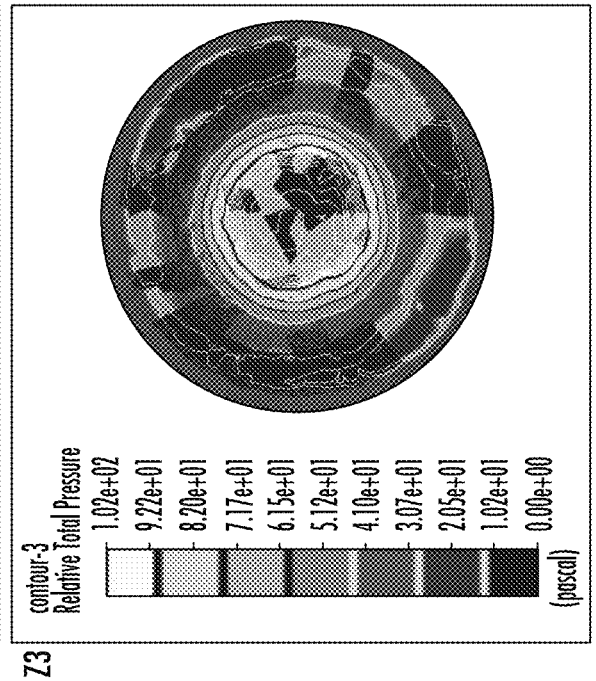
FIG. 9T

SYSTEMS AND METHODS FOR NON-INVASIVE DETERMINATION OF COVID-19 CORONAVIRUS INFECTION

CROSS-REFERENCE TO RELATED APPLICATIONS

This application is a continuation-in-part of U.S. patent application Ser. No. 16/749,611, filed on Jan. 22, 2020, which claims priority to and the benefit of U.S. Provisional Application No. 62/960,159, filed on Jan. 13, 2020, U.S. Provisional Application No. 62/952,509, filed on Dec. 23, 2019, and U.S. Provisional Application No. 62/904,405, filed on Sep. 23, 2019. U.S. patent application Ser. No. 16/749,611 is a bypass continuation-in-part of PCT/IL2018/050814, filed on Jul. 23, 2018, which claims priority to and the benefit of U.S. Provisional Application No. 62/535,917, filed on Jul. 23, 2017.

This application is also a continuation-in-part of U.S. patent application Ser. No. 16/321,261, filed on Jan. 28, 2019, which is a national stage entry of International Patent Application No. PCT/US2017/044609, filed on Jul. 31, 2017, which claims priority to and the benefit of U.S. Provisional Application No. 62/368,623, filed on Jul. 29, 2016.

This application also claims priority to and the benefit of the following provisional applications: U.S. Provisional Application No. 62/992,627, filed on Mar. 20, 2020; U.S. Provisional Application No. 63/000,077; filed on Mar. 26, 2020, U.S. Provisional Application No. 63/002,404, filed on Mar. 31, 2020, U.S. Provisional Application No. 63/012,682, filed on Apr. 20, 2020, U.S. Provisional Application No. 63/012,672, filed on Apr. 20, 2020, U.S. Provisional Application No. 63/015,714, filed on Apr. 27, 2020, U.S. Provisional Application No. 63/015,723, filed on Apr. 27, 2020, U.S. Provisional Application No. 63/032,732, filed on Jun. 1, 2020, U.S. Provisional Application No. 63/032,735, filed on Jun. 1, 2020, U.S. Provisional Application No. 63/038,920, filed on Jun. 15, 2020, U.S. Provisional Application No. 63/038,921, filed on Jun. 15, 2020, U.S. Provisional Application No. 63/051,398, filed on Jul. 14, 2020, U.S. Provisional Application No. 63/051,399, filed on Jul. 14, 2020, U.S. Provisional Application No. 63/057,319, filed on Jul. 28, 2020, U.S. Provisional Application No. 63/057,318, filed on Jul. 28, 2020, U.S. Provisional Application No. 63/075,324, filed on Sep. 8, 2020, U.S. Provisional Application No. 63/075,316, filed on Sep. 8, 2020, U.S. Provisional Application No. 63/111,089, filed on Nov. 9, 2020, and U.S. Provisional Application No. 63/111,091, filed on Nov. 9, 2020.

This application also claims priority to Israel Patent Application No. 273709, filed on Mar. 31, 2020.

All of the foregoing applications are incorporated herein by reference in their entireties.

FIELD

The present disclosure relates to systems and methods for non-invasively determination of whether individuals are infected by the COVID-19 coronavirus, and in particular, the presence or absence of COVID-19.

BACKGROUND

Coronaviruses (CoV) are a large family of viruses that cause illness ranging from the common cold to more severe diseases such as Middle East Respiratory Syndrome (MERS-CoV) and Severe Acute Respiratory Syndrome (SARS-CoV).

Coronavirus disease (COVID-19) is a new strain that was discovered in 2019 and has not been previously identified in individuals.

Coronaviruses are zoonotic, meaning they are transmitted between animals and people. Detailed investigations found that SARS-CoV was transmitted from civet cats to humans and MERS-CoV from dromedary camels to humans. Several known coronaviruses are circulating in animals that have not yet infected humans.

Common signs of infection include respiratory symptoms, fever, cough, shortness of breath and breathing difficulties. In more severe cases, infection can cause pneumonia, severe acute respiratory syndrome, kidney failure and even death.

Standard recommendations to prevent infection spread include regular hand washing, covering mouth and nose when coughing and sneezing, thoroughly cooking meat and eggs. Avoid close contact with anyone showing symptoms of respiratory illness such as coughing and sneezing. Until now no quick, label free, nondestructive method of identifying and distinguishing between a healthy human from an infected one has been presented.

Thus, there is still a long felt need for means and method for a label-free detection of Coronavirus.

The analysis of exhaled human breath is a very promising tool for medical applications. Since it is completely non-invasive, it has the potential to become a very convenient method for medical diagnoses or screenings. Furthermore, in contrast to a blood test, breath can be sampled fast and as often as required and an on-site measurement is possible. This allows also for the use of real-time analysis and detection.

The large amount of information in breath offers a path towards a better understanding of metabolism and medical diagnosis. At least some of which could be indicative to Coronavirus (COVID-19).

Thus, there is a long felt need for systems and methods to provide a noninvasive, label free determination of infection status, and namely, whether the individual is infected with COVID-19 or is instead free of COVID-19.

SUMMARY

It is one object of the present invention to provide a high throughput system for label-free, noncontact, noninvasive, and nondestructive detection of at least one virus free individual from at least one tested individual, the system comprising:

at least one sampler comprising at least one metamaterial membrane absorber located at the propagation path of volatile compounds, VCs, and/or aerosols released by said at least one tested individual breath, said metamaterial membrane absorber being configured and operable for trapping the collected volatile compounds and/or aerosols; and a control unit configured and operable for receiving data indicative of the collected volatile compounds and/or aerosols being scanned with an electromagnetic radiation in the THz range and processing said data for identifying a signature being indicative of virus free individuals to thereby provide detection of said virus free individuals.

It is one object of the present invention to provide a system for label-free, noncontact, noninvasive, and nondestructive detection of at least one virus infected individual from at least one tested individual, the system comprising:

at least one metamaterial membrane absorber located at the propagation path of volatile compounds, VCs, and/or aerosols and/or any airborne compound, released by said at least one tested individuals breath, said metamaterial membrane absorber being configured and operable for trapping the collected volatile compounds and/or aerosols; and a control unit configured and operable for receiving data indicative of the collected volatile compounds and/or aerosols being scanned with an electromagnetic radiation in the THz range and processing said data for identifying a signature being indicative of virus infected individuals to thereby provide detection of said virus infected individuals.

It is another object of the present invention to provide the system as defined above, wherein said THz range is between 200 GHz to 1200 GHz.

It is another object of the present invention to provide the system as defined above, wherein said tested individual is asymptomatic and has no symptom related to said virus.

It is another object of the present invention to provide the system as defined above, wherein said system distinguishes between a healthy individual, a virus recovered individual and an infected individual.

It is another object of the present invention to provide the system as defined above, wherein detection of said virus free individuals provides clearance to healthy individuals and/or virus recovered individuals.

It is another object of the present invention to provide the system as defined above, wherein said signature is information indicative of said virus; said information being selected from a group consisting of cell unit of said virus, viral proteins, cellular debris, debris of said virus, hydrates of said virus, hydrates of debris of said virus, hydrates of the 3D structure of said virus and a cell, aggregates of said virus, cytokines, increased level of interleukin interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the system as defined above, wherein said volatile compounds and/or aerosols create spoof surface plasmon polaritons (SSPPs) captured in said membrane.

It is another object of the present invention to provide the system as defined above, wherein said virus is selected from a group selected from COV viruses family, COVID-19, Influenza, Avian influenza and any combination thereof.

It is another object of the present invention to provide the system as defined above, wherein said virus is COVID-19.

It is another object of the present invention to provide the system as defined above, wherein said sampler is at least one selected from a group consisting of a breathalyzer, a straw-like device, any handheld device, any IOT device into which human breath is exhaled.

It is another object of the present invention to provide the system as defined above, wherein said system is at least one selected from a group consisting of a breathalyzer, any handheld device, any IOT device into which human breath is exhaled.

It is another object of the present invention to provide the system as defined above, wherein said sampler comprises a proximal end and a distal end interconnected by a main longitudinal axis, along which said at least one metamaterial membrane is positioned; and into which said tested individual exhaled breath, such that the propagation path of said exhaled breath and volatile compounds and/or aerosols therewithin intersect said at least one metamaterial membrane and absorbed therewithin.

It is another object of the present invention to provide the system as defined above, wherein said at least one metamaterial membrane is extracted from said sampler and is placed in an electromagnetic testing unit; said electromagnetic testing unit adapted to (a) scan in the THz range said metamaterial membrane absorbed with said volatile compounds and/or aerosols in said exhale breath of said tested individual; and, (b) transmit data indicative of the collected volatile compounds and/or aerosols to said control unit.

It is another object of the present invention to provide the system as defined above, wherein said sampler comprises two parts reversibly coupled to each other along a main longitudinal axis, such that (a) said at least one metamaterial membrane is positioned therebetween along said main longitudinal axis; and, (b) into said sampler said tested individual exhale breath, such that the propagation path of said exhaled breath and volatile compounds and/or aerosols therewithin intersect said at least one metamaterial membrane and absorbed therewithin.

It is another object of the present invention to provide the system as defined above, wherein said sampler is airtight sealed such that said volatile compounds, VCs, and/or aerosols released by said at least one tested individuals breath are prevented from exiting said sampler.

It is another object of the present invention to provide the system as defined above, wherein said membrane is enclosed within at least one capsule; wherein said capsule is sealed.

It is another object of the present invention to provide the system as defined above, wherein said sampler is RFID tagged with each of said tested individual, such that detection of said virus free individuals is traced back to each of said tested individual.

It is another object of the present invention to provide the system as defined above, wherein said sampler is a disposable unit.

It is another object of the present invention to provide the system as defined above, wherein said electromagnetic testing unit comprising at least one electromagnetic radiation transmitter and at least one electromagnetic radiation detector.

It is another object of the present invention to provide the system as defined above, wherein the membrane is positionable within the electromagnetic radiation emitted by the transmitter.

It is another object of the present invention to provide the system as defined above, wherein said data being processed by said control unit is at least one absorption spectrum of said membrane.

It is another object of the present invention to provide the system as defined above, wherein processing of said at least one absorption spectrum of said membrane additionally comprising pattern recognition of said at least one absorption spectrum.

It is another object of the present invention to provide the system as defined above, wherein said pattern recognition comprising at least one selected from a group consisting identification of special features of the pattern, identification of main and side peaks, the number of main and side peaks, the width of the peaks and the distance therebetween and any combination thereof.

It is another object of the present invention to provide the system as defined above, wherein said membrane is in communication with a vacuum source, a gas collection device coupled to the vacuum source, wherein the membrane is capable of capturing volatile compounds and/or aerosols.

It is another object of the present invention to provide the system as defined above, wherein said membrane is in communication with a vacuum source, a gas collection device coupled to the vacuum source, wherein the membrane is capable of capturing at least one selected from a group consisting of aerosols, volatile compounds, VCs, and any combination thereof.

It is another object of the present invention to provide the system as defined above, wherein said membrane is cleaned by applying at least one selected from a group consisting of positive/negative pressure or electricity to release said VCs and/or aerosols.

It is another object of the present invention to provide the system as defined above, wherein said membrane is coated with at least one material selected from a group consisting of Silicon, or Silicon Graphene, acting as a reflector, and any combination thereof.

It is another object of the present invention to provide the system as defined above, wherein said membrane is made of at least one material selected from a group consisting of Meta-Material Membrane, Semi Pressure Permeable Membrane, meta-material, PET, open-cell foam-based melamine and any combination thereof.

It is another object of the present invention to provide the system as defined above, additionally comprising an electromagnetic radiation transmitter and detector.

It is another object of the present invention to provide the system as defined above, wherein the membrane is positionable within the electromagnetic radiation emitted by the transmitter.

It is another object of the present invention to provide the system as defined above, wherein said control unit is configured and operable for performing a pattern recognition of said signature.

It is another object of the present invention to provide the system as defined above, wherein said system additionally comprising at one communicable and readable database; said database comprising collected volatile compounds and/or aerosols being scanned with an electromagnetic radiation in the THz range.

It is another object of the present invention to provide the system as defined above, wherein said system additionally comprising at one communicable and readable database; said database comprising at least one selected from a group consisting of aerosol, volatile compounds, VCs, and any combination thereof collected and being scanned with an electromagnetic radiation in the THz range of at least one tested individual.

It is another object of the present invention to provide the system as defined above, wherein said system has 2 modes of operation: (a) a learning phase; and, (b) a detection phase.

It is another object of the present invention to provide the system as defined above, wherein, in said learning phase, said control unit trains a machine learning model to detect at least one parameter in the absorption spectrum of said membrane with said collected volatile compounds and/or aerosols being scanned with an electromagnetic radiation in the THz range of a plurality of membrane stored in said communicable and readable database in order to generate information data being indicative of said virus free individuals.

It is another object of the present invention to provide the system as defined above, wherein, in said learning phase, said control unit trains a machine learning model to detect at least one parameter in the absorption spectrum of said membrane with said collected volatile compounds and/or aerosols being scanned with an electromagnetic radiation in the THz range of a plurality of membrane stored in said communicable and readable database in order to generate information data being indicative of said virus infected individuals.

It is another object of the present invention to provide the system as defined above, wherein said parameter selected from a group consisting of, trends in said database of said at least one tested individuals, eigenvector of said database of said at least one tested individuals, eigenvalues of said database of said at least one tested individuals, feature extraction step being configured to estimate the most relevant vectors defining the data using a principal component analysis, a pattern classification using a combined linear and nonlinear pattern recognition approach, and any combination thereof.

It is another object of the present invention to provide the system as defined above, wherein said parameter selected from a group consisting of, trends in said database of said at least one tested individuals, eigenvector of said database of said at least one tested individuals, eigenvalues of said database of said at least one tested individuals, feature extraction step being configured to estimate the most relevant vectors defining the data using a principal component analysis, a pattern classification using a combined linear and nonlinear pattern recognition approach, known symptoms of said virus, known healthy individuals, healthy individual vital signs selected from fever, sweat, body temperature, blood pressure, pulse (heart rate), and breathing rate (respiratory rate) and any combination thereof, virus free individual vital signs selected from fever, sweat, body temperature, blood pressure, pulse (heart rate), and breathing rate (respiratory rate) and any combination thereof, medicaments being administered to said tested individual, and any combination thereof.

It is another object of the present invention to provide the system as defined above, wherein, in said learning phase, said data is either supervised or unsupervised data; and, said training by said control unit is performed by at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds and/or aerosols being scanned with an electromagnetic radiation in the THz range stored in said communicable and readable database in order to generate information data being indicative of at least one said virus free individuals.

It is another object of the present invention to provide the system as defined above, wherein, in said learning phase, said training by said control unit is performed by at least one algorithm selected from a group consisting of Leave One Out (LOO) algorithm, Principal Component Analysis algorithm, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds (and/or aerosols) being scanned with an electromagnetic radiation in the THz range stored in said communicable and readable database in order to generate information data being indicative of at least one said virus infected individuals.

It is another object of the present invention to provide the system as defined above, wherein, in said detection phase, said data is either supervised or unsupervised data; and, said control unit performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds and/or aerosols being scanned with an electromagnetic radiation in the THz range stored in said communicable and readable database in order to generate information data being indicative of at least one said virus free individuals.

It is another object of the present invention to provide the system as defined above, wherein, in said detection phase, said control unit detects said signature the absorption spectrum of said membrane with said VCs and/or aerosols being indicative of at least one said virus free individuals by means of said trained machine learning model.

It is another object of the present invention to provide the system as defined above, wherein, in said detection phase, said control unit detects said signature the absorption spectrum of said membrane with said VCs and/or aerosols being indicative of at least one said virus infected individuals by means of said trained machine learning model.

It is another object of the present invention to provide the system as defined above, wherein said system additionally comprising at least one communicable and readable database storing instructions which, when executed by the at least one data processor, result in operations comprising training a machine learning model to detect at least one parameter of said collected volatile compounds and/or aerosols being scanned with an electromagnetic radiation in the THz range of at least one tested individuals stored in said communicable and readable database in order to generate information data being indicative of said virus free or virus-free individuals; and, after said step of training, real time detecting said parameter by means of said trained machine learning model.

It is another object of the present invention to provide the system as defined above, wherein said data is either supervised or unsupervised data; and, said control unit performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof in order to generate information data being indicative of said virus free individuals.

It is another object of the present invention to provide the system as defined above, wherein said control unit performs at least one algorithm selected from a group consisting of Leave One Out (LOO) algorithm, Principal Component Analysis algorithm, k-nearest neighbors algorithm, Quadrature, Fisher's linear discriminant, Fisher's nonlinear discriminant, Network Acceleration algorithm (NNA), any machine learning algorithm and any combination thereof in order to generate information data being indicative of said virus infected individuals.

It is another object of the present invention to provide the system as defined above, wherein said Principal Component Analysis is characterized by the following formula:

$$J = \frac{(m_1 - m_2)^2}{(\sigma_1^2 + \sigma_2^2)}$$

where J is the power of separation between two groups.

It is another object of the present invention to provide the system as defined above, wherein said control unit additionally performs Fast Fourier Transformation in order to generate information data being indicative of said virus free or virus infected individuals.

It is another object of the present invention to provide the system as defined above, wherein said membrane is made of hardened extruded plastic.

It is another object of the present invention to provide the system as defined above, wherein said membrane is able to trap at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1-cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, $NO_2$ and any combination thereof.

It is another object of the present invention to provide the system as defined above, wherein said membrane is single-use, disposable membrane.

It is another object of the present invention to provide the system as defined above, wherein said membrane is reusable.

It is another object of the present invention to provide the system as defined above, wherein said volatile compounds and/or aerosols comprising at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1 cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, $NO_2$ and any combination thereof.

It is another object of the present invention to provide the system as defined above, wherein said at least one selected from a group consisting of aerosol, volatile compounds, VCs, and any combination thereof comprising at least one selected from a group consisting of organic compound, non organic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, NO2 and any combination thereof.

It is another object of the present invention to provide the system as defined above, wherein said membrane is removable from the sampling apparatus.

It is another object of the present invention to provide the system as defined above, wherein said detection is completed within a period of time being less than 40 seconds.

It is another object of the present invention to provide the system as defined above, further comprising a spectroscopic assembly including a radiation transmitter unit being configured and operable to scan said membrane holding the collected volatile compounds and/or aerosols by generating an electromagnetic radiation in the range of THz within a scanning window of about 100 GHz and a detection unit being configured and operable to detect an electromagnetic radiation emitted by said collected volatile compounds and/or aerosols.

It is another object of the present invention to provide the system as defined above, wherein said system additionally comprising signaling means adapted to signal the user that sufficient enough of VCs and/or aerosols have been captured in said membrane or that said detection has been completed.

It is another object of the present invention to provide the system as defined above, wherein said signaling means are either optical or vocal means.

It is another object of the present invention to provide a high throughput system for label-free, noncontact, noninvasive, and nondestructive detection of at least one virus free individuals from at least one tested individual, the system comprising: at least one sampler comprising at least one metamaterial membrane absorber located at the propagation path of volatile compounds, VCs, and/or aerosols released by said at least one tested individuals breath, said metamaterial membrane absorber being configured and operable for trapping the collected volatile compounds and/or aerosols;

It is another object of the present invention to provide a method for label-free, noncontact, noninvasive, and nondestructive detection of at least one virus infected individual from at least one tested individual, the method comprising: receiving data indicative of collected at least one selected from a group consisting of aerosol, volatile compounds, VCs, and any combination thereof being scanned with electromagnetic radiation in the THz range; and processing said data for identifying a signature being indicative of said virus infected individuals.

It is another object of the present invention to provide the method as defined above, wherein said processing comprises performing a pattern recognition of said signature.

It is another object of the present invention to provide the system as defined above, further comprising at least one electromagnetic testing unit comprising at least one electromagnetic radiation transmitter and at least one electromagnetic radiation detector; wherein said membrane, after absorbing said volatile compounds and/or aerosols, being positionable within the electromagnetic radiation emitted by said at least one transmitter; such that said electromagnetic testing unit is adapted to (a) scan in the THz range said metamaterial membrane absorbed with said volatile compounds and/or aerosols in said exhaled breath of said tested individual; and, (b) transmit data indicative of the collected volatile compounds and/or aerosols to said control unit; and further comprising a control unit configured and operable for receiving data indicative of the collected volatile compounds and/or aerosols from said electromagnetic testing unit and processing said data for identifying a signature being indicative of virus free individuals to thereby provide detection of said virus free individuals.

It is another object of the present invention to provide the method as defined above, further comprising performing a THz spectroscopy of said membrane capturing said collected volatile compounds or aerosols.

It is another object of the present invention to provide the method as defined above, further comprising scanning the collected volatile compounds or aerosols with electromagnetic radiation in the THz range within a scanning window of about 100 GHz.

It is another object of the present invention to provide the method as defined above, further comprising trapping collected volatile compounds and/or aerosols by suction, wherein said trapping is performed within a period of time being less than 40 seconds.

It is another object of the present invention to provide the method as defined above, additionally comprising the step of providing at one communicable and readable database; said database comprising absorption spectra of collected volatile compounds and/or aerosols captured in said membrane being scanned with an electromagnetic radiation in the THz range.

It is another object of the present invention to provide the system as defined above, wherein said THz range is between 200 GHz to 1200 GHz.

It is another object of the present invention to provide the method or system as defined above, wherein said tested individual is asymptomatic and has no symptom related to said virus.

It is another object of the present invention to provide the method or system as defined above, wherein said system distinguishes between a healthy individual, a virus recovered individual and an infected individual.

It is another object of the present invention to provide the method or system as defined above, wherein detection of said virus free individuals provides clearance to healthy individuals and/or virus recovered individuals.

It is another object of the present invention to provide the system as defined above, wherein said signature is information indicative of said virus; said information being selected from a group consisting of cell unit of said virus, viral proteins, cellular debris, debris of said virus, hydrates of said virus, hydrates of debris of said virus, hydrates of the 3D structure of said virus and a cell, aggregates of said virus, cytokines, increased level of interleukin (IL)-2, interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the method or system as defined above, wherein said volatile compounds and/or aerosols create spoof surface plasmon polaritons (SSPPs) captured in said membrane.

It is another object of the present invention to provide the method as defined above, wherein said virus is COVID-19.

It is another object of the present invention to provide the system as defined above, wherein said virus is selected from a group selected from COV viruses family, COVID-19, Influenza, Avian influenza and any combination thereof.

It is another object of the present invention to provide the system as defined above, wherein said sampler is at least one selected from a group consisting of a breathalyzer, a straw-like device, any handheld device, any IOT device into which human breath is exhaled.

It is another object of the present invention to provide the method as defined above, wherein said method is performed by a system being selected from a group consisting of a breathalyzer, any handheld device, any IOT device into which human breath is exhaled.

It is another object of the present invention to provide the system as defined above, wherein said sampler comprises a proximal end and a distal end interconnected by a main longitudinal axis, along which said at least one metamaterial membrane is positioned; and into which said tested individual exhale breath, such that the propagation path of said exhaled breath and volatile compounds and/or aerosols therewithin intersect said at least one metamaterial membrane and absorbed therewithin.

It is another object of the present invention to provide the system as defined above, wherein said sampler is airtight sealed such that said volatile compounds, VCs, and/or aerosols released by said at least one tested individuals breath are prevented from exiting said sampler.

It is another object of the present invention to provide the system as defined above, wherein said membrane is enclosed within at least one capsule; wherein said capsule is sealed.

It is another object of the present invention to provide the system as defined above, wherein said sampler is RFID tagged with each of said tested individual, such that detection of said virus free individuals is traced back to each of said tested individual.

It is another object of the present invention to provide the system as defined above, wherein said sampler is a disposable unit.

It is another object of the present invention to provide the method or system as defined above, wherein said data being processed by said control unit is at least one absorption spectrum of said membrane.

It is another object of the present invention to provide the method or system as defined above, wherein processing of said at least one absorption spectrum of said membrane additionally comprising pattern recognition of said at least one absorption spectrum.

It is another object of the present invention to provide the method or system as defined above, wherein said pattern recognition comprising at least one selected from a group consisting identification of special features of the pattern, identification of main and side peaks, the number of main and side peaks, the width of the peaks and the distance therebetween and any combination thereof.

It is another object of the present invention to provide the method as defined above, wherein said membrane is in communication with a vacuum source, a gas collection device coupled to the vacuum source, wherein the membrane is capable of capturing at least one selected from a group consisting of aerosols, volatile compounds, VCs, and any combination thereof.

It is another object of the present invention to provide the system as defined above, wherein said membrane is in communication with a vacuum source, a gas collection device coupled to the vacuum source, wherein the membrane is capable of capturing volatile compounds and/or aerosols.

It is another object of the present invention to provide the method or system as defined above, wherein said membrane is cleaned by applying at least one selected from a group consisting of positive/negative pressure or electricity to release said VCs and/or aerosols.

It is another object of the present invention to provide the method or system as defined above, wherein said membrane is coated with at least one material selected from a group consisting of Silicon, or Silicon Graphene, acting as a reflector, and any combination thereof.

It is another object of the present invention to provide the method or system as defined above, wherein said membrane is made of at least one material selected from a group consisting of Meta-Material Membrane, Semi Pressure Permeable Membrane, meta-material, PET, open-cell foam-based melamine and any combination thereof.

It is another object of the present invention to provide the system as defined above, wherein said control unit is configured and operable for performing a pattern recognition of said signature.

It is another object of the present invention to provide the system as defined above, wherein said system additionally comprising at one communicable and readable database; said database comprising collected volatile compounds and/or aerosols being scanned with an electromagnetic radiation in the THz range.

It is another object of the present invention to provide the system as defined above, wherein said system has 2 modes of operation: (a) a learning phase; and, (b) a detection phase.

It is another object of the present invention to provide the system as defined above, wherein, in said learning phase, said control unit trains a machine learning model to detect at least one parameter in the absorption spectrum of said membrane with said collected volatile compounds and/or aerosols being scanned with an electromagnetic radiation in the THz range of a plurality of membrane stored in said communicable and readable database in order to generate information data being indicative of said virus free individuals.

It is another object of the present invention to provide the method as defined above, additionally comprising an electromagnetic radiation transmitter and detector.

It is another object of the present invention to provide the method as defined above, wherein the membrane is positionable within the electromagnetic radiation emitted by the transmitter.

It is another object of the present invention to provide the method as defined above, wherein said control unit is configured and operable for performing a pattern recognition of said signature.

It is another object of the present invention to provide the method as defined above, additionally comprising at one communicable and readable database; said database comprising collected volatile compounds and/or aerosols being scanned with an electromagnetic radiation in the THz range.

It is another object of the present invention to provide the method as defined above, wherein said method has 2 modes of operation: (a) a learning phase; and, (b) a detection phase.

It is another object of the present invention to provide the method as defined above, wherein, in said learning phase, said control unit trains a machine learning model to detect at least one parameter in the absorption spectrum of said membrane with said collected volatile compounds and/or aerosols being scanned with an electromagnetic radiation in the THz range of a plurality of membrane stored in said communicable and readable database in order to generate information data being indicative of said virus infected individuals.

It is another object of the present invention to provide the method as defined above, wherein, in said learning phase, said control unit trains a machine learning model to detect at least one parameter in the absorption spectrum of said membrane with said collected volatile compounds and/or aerosols being scanned with an electromagnetic radiation in the THz range of a plurality of membrane stored in said communicable and readable database in order to generate information data being indicative of said virus infected individuals.

It is another object of the present invention to provide the method as defined above, wherein aid parameter selected from a group consisting of, trends in said database of said at least one tested individual, eigenvector of said database of said at least one tested individual, eigenvalues of said database of said at least one tested individual, feature extraction step being configured to estimate the most relevant vectors defining the data using a principal component analysis, a pattern classification using a combined linear and nonlinear pattern recognition approach, and any combination thereof.

It is another object of the present invention to provide the system as defined above, wherein aid parameter selected from a group consisting of, trends in said database of said at least one tested individuals, eigenvector of said database of said at least one tested individuals, eigenvalues of said database of said at least one tested individuals, feature extraction step being configured to estimate the most relevant vectors defining the data using a principal component analysis, a pattern classification using a combined linear and nonlinear pattern recognition approach, known symptoms of said virus, known healthy individuals, healthy individual vital signs selected from fever, sweat, body temperature, blood pressure, pulse (heart rate), and breathing rate (respiratory rate) and any combination thereof, virus free individual vital signs selected from fever, sweat, body temperature, blood pressure, pulse (heart rate), and breathing rate (respiratory rate) and any combination thereof, medicaments being administered to said tested individual, and any combination thereof.

It is another object of the present invention to provide the system as defined above, wherein, in said learning phase, said data is either supervised or unsupervised data; and, said training by said control unit is performed by at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds and/or aerosols being scanned with an electromagnetic radiation in the THz range stored in said communicable and readable database in order to generate information data being indicative of at least one said virus free individuals.

It is another object of the present invention to provide the method as defined above, wherein, in said detection phase, said control unit performs at least one algorithm selected from a group consisting of Leave One Out (LOO) algorithm, Principal Component Analysis algorithm, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds and/or aerosols being scanned with an electromagnetic radiation in the THz range stored in said communicable and readable database in order to generate information data being indicative of at least one said virus infected individual.

It is another object of the present invention to provide the system as defined above, wherein, in said detection phase, said data is either supervised or unsupervised data; and, said control unit performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds and/or aerosols being scanned with an electromagnetic radiation in the THz range stored in said communicable and readable database in order to generate information data being indicative of at least one said virus free individuals.

It is another object of the present invention to provide the system as defined above, wherein, in said detection phase, said control unit detects said signature the absorption spectrum of said membrane with said VCs and/or aerosols being indicative of at least one said virus free individuals by means of said trained machine learning model.

As defined above, wherein, in said detection phase, said control unit detects said signature the absorption spectrum of said membrane with said VCs and/or aerosols being indicative of at least one said virus infected individual by means of said trained machine learning model.

It is another object of the present invention to provide the method as defined above, additionally comprising at least one communicable and readable database storing instructions which, when executed by the at least one data processor, result in operations comprising: training a machine learning model to detect at least one parameter of said collected volatile compounds and/or aerosols being scanned with an electromagnetic radiation in the THz range of at least one tested individual stored in said communicable and readable database in order to generate information data being indicative of said virus infected individuals; and, after said step of training, real time detecting said parameter by means of said trained machine learning model.

It is another object of the present invention to provide the system as defined above, wherein said system additionally comprising at least one communicable and readable database storing instructions which, when executed by the at least one data processor, result in operations comprising: training a machine learning model to detect at least one parameter of said collected volatile compounds and/or aerosols being scanned with an electromagnetic radiation in the THz range of at least one tested individuals stored in said communicable and readable database in order to generate information data being indicative of said virus free individuals; and, after said step of training, real time detecting said parameter by means of said trained machine learning model.

It is another object of the present invention to provide the system as defined above, wherein said data is either supervised or unsupervised data; and, said control unit performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof in order to generate information data being indicative of said virus free individuals.

It is another object of the present invention to provide the method as defined above, wherein said control unit performs at least one algorithm selected from a group consisting of Leave One Out (LOO) algorithm, Principal Component Analysis algorithm, k-nearest neighbors algorithm, Quadrature, Fisher's linear discriminant, Fisher's nonlinear discriminant, Network Acceleration algorithm (NNA), any machine learning algorithm and any combination thereof in order to generate information data being indicative of said virus infected individuals.

It is another object of the present invention to provide the system as defined above, wherein said control unit additionally performs Fast Fourier Transformation in order to generate information data being indicative of said virus free individuals.

It is another object of the present invention to provide the method as defined above, wherein said Principal Component Analysis is characterized by the following formula:

$$J = \frac{(m_1 - m_2)^2}{(\sigma_1^2 + \sigma_2^2)}$$

where J is the power of separation between two groups.

It is another object of the present invention to provide the method as defined above, wherein said control unit additionally performs Fast Fourier Transformation in order to generate information data being indicative of said virus infected individuals.

It is another object of the present invention to provide the method or system as defined above, wherein said membrane is made of hardened extruded plastic.

It is another object of the present invention to provide the method as defined above, wherein said membrane is able to trap at least one selected from a group consisting of organic compound, non organic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane (CH4), Carbon dioxide (CO2), Nitrous oxide (N2O), Ozone (O3), Chlorofluorocarbons (CFCs), Hydrofluorocarbons (includes HCFCs and HFCs), NO, NO2 and any combination thereof.

It is another object of the present invention to provide the system as defined above, wherein said membrane is able to trap at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane (CH4), Carbon dioxide (CO2), Nitrous oxide (N2O), Ozone (O3), Chlorofluorocarbons (CFCs), Hydrofluorocarbons (includes HCFCs and HFCs), NO, NO2, viral proteins, cellular debris, debris of said virus, hydrates of said virus, hydrates of debris of said virus, hydrates of the 3D structure of said virus and a cell, aggregates of said virus, cytokines, increased level of interleukin interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the method or system as defined above, wherein said membrane is single-use, disposable membrane.

It is another object of the present invention to provide the method or system as defined above, wherein said membrane is reusable.

It is another object of the present invention to provide the method as defined above, wherein said at least one selected from a group consisting of aerosol, volatile compounds, VCs, and any combination thereof comprising at least one selected from a group consisting of organic compound, non organic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane (CH4), Carbon dioxide (CO2), Nitrous oxide (N2O), Ozone (O3), Chlorofluorocarbons (CFCs), Hydrofluorocarbons (includes HCFCs and HFCs), NO, NO2 and any combination thereof.

It is another object of the present invention to provide the system as defined above, wherein said volatile compounds and/or aerosols comprise at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane (CH4), Carbon dioxide (CO2), Nitrous oxide (N2O), Ozone (O3), Chlorofluorocarbons (CFCs), Hydrofluorocarbons (includes HCFCs and HFCs), NO, NO2, viral proteins, cellular debris, debris of said virus, hydrates of said virus, hydrates of debris of said virus, hydrates of the 3D structure of said virus and a cell, aggregates of said virus, cytokines, increased level of interleukin (IL)-2, interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the method or system as defined above, wherein said membrane is removable from the sampling apparatus.

It is another object of the present invention to provide the method or system as defined above, wherein said detection is completed within a period of time being less than 40 seconds.

It is another object of the present invention to provide the method or system as defined above, further comprising a spectroscopic assembly including a radiation transmitter unit being configured and operable to scan said membrane holding the collected volatile compounds and/or aerosols by generating an electromagnetic radiation in the range of THz within a scanning window of about 100 GHz and a detection unit being configured and operable to detect an electromagnetic radiation emitted by said collected volatile compounds and/or aerosols.

It is another object of the present invention to provide the method as defined above, method or additionally comprising signaling means adapted to signal the user that sufficient enough of VCs and/or aerosols have been captured in said membrane or that said detection has been completed.

It is another object of the present invention to provide the system as defined above, wherein said method or system additionally comprising signaling means adapted to signal the user that sufficient enough of VCs and/or aerosols have been captured in said membrane or that said detection has been completed.

It is another object of the present invention to provide the method or system as defined above, wherein said signaling means are either optical or vocal means.

It is another object of the present invention to provide a sampler to be integrated into a system for label-free, non-contact, noninvasive, and nondestructive detection of at least one virus free individuals from at least one tested individual, the sampler comprising: a proximal end and a distal end interconnected by a main longitudinal axis, along which at least one metamaterial membrane absorber is positioned; and into which said tested individual exhale breath, such that the propagation path of said exhaled breath and volatile compounds, VCs, and/or aerosols therewithin intersect said at least one metamaterial membrane and absorbed therewithin, said metamaterial membrane absorber being configured and operable for trapping the collected volatile compounds and/or aerosols.

It is another object of the present invention to provide the sampler as defined above, wherein said system additionally comprising a control unit configured and operable for receiving data indicative of the collected volatile compounds and/or aerosols being scanned with an electromagnetic radiation in the THz range and processing said data for identifying a signature being indicative of virus free individuals to thereby provide detection of said virus free individuals.

It is another object of the present invention to provide the sampler as defined above, wherein said sampler is airtight sealed such that said volatile compounds, VCs, and/or aerosols released by said at least one tested individuals breath are prevented from exiting said sampler.

It is another object of the present invention to provide the sampler as defined above, wherein said membrane is enclosed within at least one capsule; wherein said capsule is sealed.

It is another object of the present invention to provide the sampler as defined above, wherein said sampler is RFID tagged with each of said tested individual, such that detection of said virus free individuals is traced back to each of said tested individual.

It is another object of the present invention to provide the sampler as defined above, wherein said sampler is a disposable unit.

It is another object of the present invention to provide the sampler as defined above, wherein said THz range is between 200 GHz to 1200 GHz.

It is another object of the present invention to provide the sampler as defined above, wherein said tested individual is asymptomatic and has no symptom related to said virus.

It is another object of the present invention to provide the sampler as defined above, wherein said system distinguishes between a healthy individual, a virus recovered individual and an infected individual.

It is another object of the present invention to provide the sampler as defined above, wherein detection of said virus free individuals provides clearance to healthy individuals and/or virus recovered individuals.

It is another object of the present invention to provide the sampler as defined above, wherein said signature is information indicative of said virus; said information being selected from a group consisting of cell unit of said virus, viral proteins, cellular debris, debris of said virus, hydrates of said virus, hydrates of debris of said virus, hydrates of the 3D structure of said virus and a cell, aggregates of said virus, cytokines, increased level of interleukin (IL)-2, interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the sampler as defined above, wherein said volatile compounds and/or aerosols create spoof surface plasmon polaritons (SSPPs) captured in said membrane.

It is another object of the present invention to provide the sampler as defined above, wherein said virus is selected from a group selected from COV viruses family, COVID-19, Influenza, Avian influenza and any combination thereof.

It is another object of the present invention to provide the sampler as defined above, wherein said sampler is at least one selected from a group consisting of a breathalyzer, a straw-like device, any handheld device, any IOT device into which human breath is exhaled.

It is another object of the present invention to provide the sampler as defined above, wherein said at least one metamaterial membrane is extracted from said sampler and is placed in an electromagnetic testing unit; said electromagnetic testing unit adapted to (a) scan in the THz range said metamaterial membrane absorbed with said volatile compounds and/or aerosols in said exhaled breath of said tested individual; and, (b) transmit data indicative of the collected volatile compounds and/or aerosols to said control unit.

It is another object of the present invention to provide the sampler as defined above, wherein said sampler comprises two parts reversibly coupled to each other along a main longitudinal axis, such that (a) said at least one metamaterial membrane is positioned therebetween along said main longitudinal axis; and, (b) into said sampler said tested individual exhale breath, such that the propagation path of said exhaled breath and volatile compounds and/or aerosols therewithin intersect said at least one metamaterial membrane and absorbed therewithin.

It is another object of the present invention to provide the sampler as defined above, wherein said electromagnetic testing unit comprising at least one electromagnetic radiation transmitter and at least one electromagnetic radiation detector.

It is another object of the present invention to provide the sampler as defined above, wherein the membrane is positionable within the electromagnetic radiation emitted by the transmitter.

It is another object of the present invention to provide the sampler as defined above, wherein said data being processed by said control unit is at least one absorption spectrum of said membrane.

It is another object of the present invention to provide the sampler as defined above, wherein processing of said at least one absorption spectrum of said membrane additionally comprising pattern recognition of said at least one absorption spectrum.

It is another object of the present invention to provide the sampler as defined above, wherein said pattern recognition comprising at least one selected from a group consisting of identification of special features of the pattern, identification of main and side peaks, the number of main and side peaks, the width of the peaks and the distance therebetween and any combination thereof.

It is another object of the present invention to provide the sampler as defined above, wherein said membrane is in communication with a vacuum source, a gas collection device coupled to the vacuum source, wherein the membrane is capable of capturing volatile compounds and/or aerosols.

It is another object of the present invention to provide the sampler as defined above, wherein said membrane is cleaned by applying at least one selected from a group consisting of positive/negative pressure or electricity to release said VCs and/or aerosols.

It is another object of the present invention to provide the sampler as defined above, wherein said membrane is coated with at least one material selected from a group consisting of Silicon, or Silicon Graphene, acting as a reflector, and any combination thereof.

It is another object of the present invention to provide the sampler as defined above, wherein said membrane is made of at least one material selected from a group consisting of Meta-Material Membrane, Semi Pressure Permeable Membrane, meta-material, PET, open-cell foam-based melamine and any combination thereof.

It is another object of the present invention to provide the sampler as defined above, wherein said control unit is configured and operable for performing a pattern recognition of said signature.

It is another object of the present invention to provide the sampler as defined above, wherein said system additionally comprising at one communicable and readable database; said database comprising collected volatile compounds and/or aerosols being scanned with an electromagnetic radiation in the THz range.

It is another object of the present invention to provide the sampler as defined above, wherein said system has 2 modes of operation: (a) a learning phase; and, (b) a detection phase.

It is another object of the present invention to provide the sampler as defined above, wherein, in said learning phase, said control unit trains a machine learning model to detect at least one parameter in the absorption spectrum of said membrane with said collected volatile compounds and/or aerosols being scanned with an electromagnetic radiation in the THz range of a plurality of membrane stored in said communicable and readable database in order to generate information data being indicative of said virus free individuals.

It is another object of the present invention to provide the sampler as defined above, wherein aid parameter selected from a group consisting of, trends in said database of said at least one tested individuals, eigenvector of said database of said at least one tested individuals, eigenvalues of said database of said at least one tested individuals, feature extraction step being configured to estimate the most relevant vectors defining the data using a principal component analysis, a pattern classification using a combined linear and nonlinear pattern recognition approach, known symptoms of said virus, known healthy individuals, healthy individual vital signs selected from fever, sweat, body temperature, blood pressure, pulse (heart rate), and breathing rate (respiratory rate) and any combination thereof, virus free individual vital signs selected from fever, sweat, body temperature, blood pressure, pulse (heart rate), and breathing rate (respiratory rate) and any combination thereof, medicaments being administered to said tested individual, and any combination thereof.

It is another object of the present invention to provide the sampler as defined above, wherein, in said learning phase, said data is either supervised or unsupervised data; and, said training by said control unit is performed by at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds and/or aerosols being scanned with an electromagnetic radiation in the THz range stored in said communicable and readable database in order to generate information data being indicative of at least one said virus free individuals.

It is another object of the present invention to provide the sampler as defined above, wherein, in said detection phase, said data is either supervised or unsupervised data; and, said control unit performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds and/or aerosols being scanned with an electromagnetic radiation in the THz range stored in said communicable and readable database in order to generate information data being indicative of at least one said virus free individuals.

It is another object of the present invention to provide the sampler as defined above, wherein, in said detection phase, said control unit detects said signature the absorption spectrum of said membrane with said VCs and/or aerosols being indicative of at least one said virus free individuals by means of said trained machine learning model.

It is another object of the present invention to provide the sampler as defined above, wherein said system additionally comprising at least one communicable and readable database storing instructions which, when executed by the at least one data processor, result in operations comprising: training a machine learning model to detect at least one parameter of said collected volatile compounds and/or aerosols being scanned with an electromagnetic radiation in the THz range of at least one tested individuals stored in said communicable and readable database in order to generate information data being indicative of said virus free individuals; and, after said step of training, real time detecting said parameter by means of said trained machine learning model.

It is another object of the present invention to provide the sampler as defined above, wherein said data is either supervised or unsupervised data; and, said control unit performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof in order to generate information data being indicative of said virus free individuals.

It is another object of the present invention to provide the sampler as defined above, wherein said control unit additionally performs Fast Fourier Transformation in order to generate information data being indicative of said virus free individuals.

It is another object of the present invention to provide the sampler as defined above, wherein said membrane is made of hardened extruded plastic.

It is another object of the present invention to provide the sampler as defined above, wherein said membrane is able to trap at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, $NO_2$, viral proteins, cellular debris, debris of said virus, hydrates of said virus, hydrates of debris of said virus, hydrates of the 3D structure of said virus and a cell, aggregates of said virus, cytokines, increased level of interleukin interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the sampler as defined above, wherein said membrane is single-use, disposable membrane.

It is another object of the present invention to provide the sampler as defined above, wherein said membrane is reusable.

It is another object of the present invention to provide the sampler as defined above, wherein said volatile compounds and/or aerosols comprising at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, $NO_2$, viral proteins, cellular debris, debris of said virus, hydrates of said virus, hydrates of debris of said virus, hydrates of the 3D structure of said virus and a cell, aggregates of said virus, cytokines, increased level of interleukin (IL)-2, interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the sampler as defined above, wherein said membrane is removable from the sampling apparatus.

It is another object of the present invention to provide the sampler as defined above, wherein said detection is completed within a period of time being less than 40 seconds.

It is another object of the present invention to provide the sampler as defined above, further comprising a spectroscopic assembly including a radiation transmitter unit being configured and operable to scan said membrane holding the collected volatile compounds and/or aerosols by generating an electromagnetic radiation in the range of THz within a scanning window of about 100 GHz and a detection unit being configured and operable to detect an electromagnetic radiation emitted by said collected volatile compounds and/or aerosols.

It is another object of the present invention to provide the sampler as defined above, wherein said system additionally comprising signaling means adapted to signal the user that sufficient enough of VCs and/or aerosols have been captured in said membrane or that said detection has been completed.

It is another object of the present invention to provide the sampler as defined above, wherein said signaling means are either optical or vocal means.

It is another object of the present invention to provide a high throughput method for label-free, noncontact, noninvasive, and nondestructive detection of at least one virus free individual from at least one tested individual, the method comprising: receiving data indicative of collected volatile compounds, VCs, and/or aerosols being scanned with electromagnetic radiation in the THz range; and processing said data for identifying a signature being indicative of said virus free individuals.

It is another object of the present invention to provide the method as defined above, wherein said THz range is between 200 GHz to 1200 GHz.

It is another object of the present invention to provide the method as defined above, wherein said tested individual is asymptomatic and has no symptom related to said virus.

It is another object of the present invention to provide the method as defined above, wherein said system distinguishes between a healthy individual, a virus recovered individual and an infected individual.

It is another object of the present invention to provide the method as defined above, wherein detection of said virus free individuals provides clearance to healthy individuals and/or virus recovered individuals.

It is another object of the present invention to provide the method as defined above, wherein said signature is information indicative of said virus; said information being selected from a group consisting of cell unit of said virus, viral proteins, cellular debris, debris of said virus, hydrates of said virus, hydrates of debris of said virus, hydrates of the 3D structure of said virus and a cell, aggregates of said virus, cytokines, increased level of interleukin interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the method as defined above, wherein said processing comprises performing a pattern recognition of said signature.

It is another object of the present invention to provide the method as defined above, further comprising scanning the collected volatile compounds and/or aerosols with electromagnetic radiation in the THz range within a scanning window of about 100 GHz.

It is another object of the present invention to provide the method as defined above, additionally comprising the step of providing at one communicable and readable database; said database comprising absorption spectra of collected volatile compounds and/or aerosols captured in said membrane being scanned with an electromagnetic radiation in the THz range.

It is another object of the present invention to provide the method as defined above, wherein said volatile compounds and/or aerosols create spoof surface plasmon polaritons (SSPPs) captured in said membrane.

It is another object of the present invention to provide the method as defined above, wherein said virus is selected from a group selected from COV viruses family, COVID-19, Influenza, Avian influenza and any combination thereof.

It is another object of the present invention to provide the method as defined above, wherein said method is performed by a system being selected from a group consisting of a breathalyzer, any handheld device, any IOT device into which human breath is exhaled.

It is another object of the present invention to provide the method as defined above, wherein said data being processed by said control unit is at least one absorption spectrum of said membrane.

It is another object of the present invention to provide the method as defined above, wherein processing of said at least one absorption spectrum of said membrane additionally comprising pattern recognition of said at least one absorption spectrum.

It is another object of the present invention to provide the method as defined above, wherein said pattern recognition comprising at least one selected from a group consisting identification of special features of the pattern, identification of main and side peaks, the number of main and side peaks, the width of the peaks and the distance therebetween and any combination thereof.

It is another object of the present invention to provide the method as defined above, wherein said membrane is in communication with a vacuum source, a gas collection device coupled to the vacuum source, wherein the membrane is capable of capturing volatile compounds and/or aerosols.

It is another object of the present invention to provide the method as defined above, wherein said membrane is cleaned by applying at least one selected from a group consisting of positive/negative pressure or electricity to release said VCs and/or aerosols.

It is another object of the present invention to provide the method as defined above, wherein said membrane is coated with at least one material selected from a group consisting of Silicon, or Silicon Graphene, acting as a reflector, and any combination thereof.

It is another object of the present invention to provide the method as defined above, wherein said membrane is made of at least one material selected from a group consisting of Meta-Material Membrane, Semi Pressure Permeable Membrane, meta-material, PET, open-cell foam-based melamine and any combination thereof.

It is another object of the present invention to provide the method as defined above, additionally comprising an electromagnetic radiation transmitter and detector.

It is another object of the present invention to provide the method as defined above, wherein the membrane is positionable within the electromagnetic radiation emitted by the transmitter.

It is another object of the present invention to provide the method as defined above, additionally comprising at one communicable and readable database; said database comprising collected volatile compounds and/or aerosols being scanned with an electromagnetic radiation in the THz range.

It is another object of the present invention to provide the method as defined above, wherein said method has 2 modes of operation: (a) a learning phase; and, (b) a detection phase.

It is another object of the present invention to provide the method as defined above, wherein, in said learning phase, said control unit trains a machine learning model to detect at least one parameter in the absorption spectrum of said membrane with said collected volatile compounds and/or aerosols being scanned with an electromagnetic radiation in the THz range of a plurality of membrane stored in said communicable and readable database in order to generate information data being indicative of said virus free individuals.

It is another object of the present invention to provide the method as defined above, wherein aid parameter selected from a group consisting of, trends in said database of said at least one tested individuals, eigenvector of said database of said at least one tested individuals, eigenvalues of said database of said at least one tested individuals, feature extraction step being configured to estimate the most relevant vectors defining the data using a principal component analysis, a pattern classification using a combined linear and nonlinear pattern recognition approach, known symptoms of said virus, known healthy individuals, healthy individual vital signs selected from fever, sweat, body temperature, blood pressure, pulse (heart rate), and breathing rate (respiratory rate) and any combination thereof, virus free individual vital signs selected from fever, sweat, body temperature, blood pressure, pulse (heart rate), and breathing rate (respiratory rate) and any combination thereof, medicaments being administered to said tested individual, and any combination thereof.

It is another object of the present invention to provide the method as defined above, wherein, in said learning phase, said data is either supervised or unsupervised data; and, said training by said control unit is performed by at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds and/or aerosols being scanned with an electromagnetic radiation in the THz range stored in said communicable and readable database in order to generate information data being indicative of at least one said virus free individuals.

It is another object of the present invention to provide the method as defined above, wherein, in said detection phase, said data is either supervised or unsupervised data; and, said control unit performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds and/or aerosols being scanned with an electromagnetic radiation in the THz range stored in said communicable and readable database in order to generate information data being indicative of at least one said virus free individuals.

It is another object of the present invention to provide the method as defined above, wherein, in said detection phase, said control unit detects said signature the absorption spectrum of said membrane with said VCs and/or aerosols being indicative of at least one said virus free individuals by means of said trained machine learning model.

It is another object of the present invention to provide the method as defined above, additionally comprising at least one communicable and readable database storing instructions which, when executed by the at least one data processor, result in operations comprising: training a machine learning model to detect at least one parameter of said collected volatile compounds and/or aerosols being scanned with an electromagnetic radiation in the THz range of at least one tested individuals stored in said communicable and readable database in order to generate information data being indicative of said virus free individuals; and, after said step of training, real time detecting said parameter by means of said trained machine learning model.

It is another object of the present invention to provide the method as defined above, wherein said control unit additionally performs Fast Fourier Transformation in order to generate information data being indicative of said virus free individuals.

It is another object of the present invention to provide the method as defined above, wherein said membrane is made of hardened extruded plastic.

It is another object of the present invention to provide the method as defined above, wherein said membrane is able to trap at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, $NO_2$, viral proteins, cellular debris, debris of said virus, hydrates of said virus, hydrates of debris of said virus, hydrates of the 3D structure of said virus and a cell, aggregates of said virus, cytokines, increased level of interleukin interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the method as defined above, wherein said membrane is single-use, disposable membrane.

It is another object of the present invention to provide the method as defined above, wherein said membrane is reusable.

It is another object of the present invention to provide the method as defined above, wherein said membrane is removable from the sampling apparatus.

It is another object of the present invention to provide the method as defined above, further comprising a spectroscopic assembly including a radiation transmitter unit being configured and operable to scan said membrane holding the collected volatile compounds and/or aerosols by generating an electromagnetic radiation in the range of THz within a scanning window of about 100 GHz and a detection unit being configured and operable to detect an electromagnetic radiation emitted by said collected volatile compounds and/or aerosols.

It is another object of the present invention to provide the method as defined above, additionally comprising signaling means adapted to signal the user that sufficient enough of VCs and/or aerosols have been captured in said membrane or that said detection has been completed.

It is another object of the present invention to provide the method as defined above, wherein said signaling means are either optical or vocal means.

It is another object of the present invention to provide a high throughput method for label-free, noncontact, noninvasive, and nondestructive detection of at least one virus free individual from at least one tested individual, the method comprising: providing at least one sampler comprising at least one metamaterial membrane absorber located at the propagation path of volatile compounds, VCs, and/or aerosols released by said at least one tested individual breath, said metamaterial membrane absorber being configured and operable for trapping the collected volatile compounds and/or aerosols; receiving data indicative of collected volatile compounds, VCs, and/or aerosols being scanned with electromagnetic radiation in the THz range; and processing said data for identifying a signature being indicative of said virus free individuals.

It is another object of the present invention to provide the method as defined above, wherein said THz range is between 200 GHz to 1200 GHz.

It is another object of the present invention to provide the method as defined above, wherein said tested individual is asymptomatic and has no symptom related to said virus.

It is another object of the present invention to provide the method as defined above, wherein said system distinguishes between a healthy individual, a virus recovered individual and an infected individual.

It is another object of the present invention to provide the method as defined above, wherein detection of said virus free individuals provides clearance to healthy individuals and/or virus recovered individuals.

It is another object of the present invention to provide the method as defined above, wherein said signature is information indicative of said virus; said information being selected from a group consisting of cell unit of said virus, viral proteins, cellular debris, debris of said virus, hydrates of said virus, hydrates of debris of said virus, hydrates of the 3D structure of said virus and a cell, aggregates of said virus, cytokines, increased level of interleukin (IL)-2, interleukin IL-7, interleukin-2 receptor (IL-2R), interleukin-6 (IL-6), granulocytecolony, stimulating factor, interferon-γ, inducible protein 10, monocyte chemoattractant, protein 174, macrophage, inflammatory protein 1-α, and tumor necrosis factor-α, and any combination thereof.

It is another object of the present invention to provide the method as defined above, wherein said volatile compounds and/or aerosols create spoof surface plasmon polaritons (SSPPs) captured in said membrane.

It is another object of the present invention to provide the method as defined above, wherein said virus is selected from a group selected from COV viruses family, COVID-19, Influenza, Avian influenza and any combination thereof.

It is another object of the present invention to provide the method as defined above, wherein said sampler is at least one selected from a group consisting of a breathalyzer, a straw-like device, any handheld device, any IOT device into which human breath is exhaled.

It is another object of the present invention to provide the method as defined above, wherein said sampler comprises a proximal end and a distal end interconnected by a main longitudinal axis, along which said at least one metamaterial membrane is positioned; and into which said tested individual exhaled breath, such that the propagation path of said exhaled breath and volatile compounds and/or aerosols therewithin intersect said at least one metamaterial membrane and absorbed therewithin.

It is another object of the present invention to provide the method as defined above, wherein said sampler is airtight sealed such that said volatile compounds, VCs, and/or aerosols released by said at least one tested individuals breath are prevented from exiting said sampler.

It is another object of the present invention to provide the method as defined above, wherein said membrane is enclosed within at least one capsule; wherein said capsule is sealed.

It is another object of the present invention to provide the method as defined above, wherein said sampler is RFID tagged with each of said tested individual, such that detection of said virus free individuals is traced back to each of said tested individual.

It is another object of the present invention to provide the method as defined above, wherein said sampler is a disposable unit.

It is another object of the present invention to provide the method as defined above, wherein said at least one metamaterial membrane is extracted from said sampler and is placed in an electromagnetic testing unit; said electromagnetic testing unit adapted to (a) scan in the THz range said metamaterial membrane absorbed with said volatile compounds and/or aerosols in said exhale breath of said tested individual; and, (b) transmit data indicative of the collected volatile compounds and/or aerosols to said control unit.

It is another object of the present invention to provide the method as defined above, wherein said sampler comprises two parts reversibly coupled to each other along a main longitudinal axis, such that (a) said at least one metamaterial membrane is positioned therebetween along said main longitudinal axis; and, (b) into said sampler said tested individual exhale breath, such that the propagation path of said exhaled breath and volatile compounds and/or aerosols therewithin intersect said at least one metamaterial membrane and absorbed therewithin.

It is another object of the present invention to provide the method as defined above, wherein said electromagnetic testing unit comprising at least one electromagnetic radiation transmitter and at least one electromagnetic radiation detector.

It is another object of the present invention to provide the method as defined above, wherein the membrane is positionable within the electromagnetic radiation emitted by the transmitter.

It is another object of the present invention to provide the method as defined above, wherein said data being processed by said control unit is at least one absorption spectrum of said membrane.

It is another object of the present invention to provide the method as defined above, wherein processing of said at least one absorption spectrum of said membrane additionally comprising pattern recognition of said at least one absorption spectrum.

It is another object of the present invention to provide the method as defined above, wherein said pattern recognition comprising at least one selected from a group consisting identification of special features of the pattern, identification of main and side peaks, the number of main and side peaks, the width of the peaks and the distance therebetween and any combination thereof.

It is another object of the present invention to provide the method as defined above, wherein said membrane is in communication with a vacuum source, a gas collection device coupled to the vacuum source, wherein the membrane is capable of capturing volatile compounds and/or aerosols.

It is another object of the present invention to provide the method as defined above, wherein said membrane is cleaned by applying at least one selected from a group consisting of positive/negative pressure or electricity to release said VCs and/or aerosols.

It is another object of the present invention to provide the method as defined above, wherein said membrane is coated with at least one material selected from a group consisting of Silicon, or Silicon Graphene, acting as a reflector, and any combination thereof.

It is another object of the present invention to provide the method as defined above, wherein said membrane is made of at least one material selected from a group consisting of Meta-Material Membrane, Semi Pressure Permeable Membrane, meta-material, PET, open-cell foam-based melamine and any combination thereof.

It is another object of the present invention to provide the method as defined above, wherein said control unit is configured and operable for performing a pattern recognition of said signature.

It is another object of the present invention to provide the method as defined above, wherein said system additionally comprising at one communicable and readable database; said database comprising collected volatile compounds and/or aerosols being scanned with an electromagnetic radiation in the THz range.

It is another object of the present invention to provide the method as defined above, wherein said data is either supervised or unsupervised data; and, said control unit performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof in order to generate information data being indicative of said virus free individuals.

It is another object of the present invention to provide the method as defined above, wherein said control unit additionally performs Fast Fourier Transformation in order to generate information data being indicative of said virus free individuals.

It is another object of the present invention to provide the method as defined above, wherein said membrane is made of hardened extruded plastic.

It is another object of the present invention to provide the method as defined above, wherein said membrane is able to trap at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, $NO_2$, viral proteins, cellular debris, debris of said virus, hydrates of said virus, hydrates of debris of said virus, hydrates of the 3D structure of said virus and a cell, aggregates of said virus, cytokines, increased level of interleukin interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the method as defined above, wherein said membrane is single-use, disposable membrane.

It is another object of the present invention to provide the method as defined above, wherein said membrane is reusable.

It is another object of the present invention to provide the method as defined above, wherein said volatile compounds and/or aerosols comprising at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1 cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane (CH4), Carbon dioxide (CO2), Nitrous oxide (N2O), Ozone (O3), Chlorofluorocarbons (CFCs), Hydrofluorocarbons (includes HCFCs and HFCs), NO, NO2, viral proteins, cellular debris, debris of said virus, hydrates of said virus, hydrates of debris of said virus, hydrates of the 3D structure of said virus and a cell, aggregates of said virus, cytokines, increased level of interleukin (IL)-2, interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the method as defined above, wherein said membrane is removable from the sampling apparatus.

It is another object of the present invention to provide the method as defined above, wherein said detection is completed within a period of time being less than 40 seconds.

It is another object of the present invention to provide the method as defined above, further comprising a spectroscopic assembly including a radiation transmitter unit being configured and operable to scan said membrane holding the collected volatile compounds and/or aerosols by generating an electromagnetic radiation in the range of THz within a scanning window of about 100 GHz and a detection unit being configured and operable to detect an electromagnetic radiation emitted by said collected volatile compounds and/or aerosols.

It is another object of the present invention to provide the method as defined above, wherein said system additionally comprising signaling means adapted to signal the user that sufficient enough of VCs and/or aerosols have been captured in said membrane or that said detection has been completed.

It is another object of the present invention to provide the method as defined above, wherein said signaling means are either optical or vocal means.

It is another object of the present invention to provide the method as defined above, wherein said processing comprises performing a pattern recognition of said signature.

It is another object of the present invention to provide the method as defined above, further comprising scanning the collected volatile compounds and/or aerosols with electromagnetic radiation in the THz range within a scanning window of about 100 GHz.

It is another object of the present invention to provide the method as defined above, additionally comprising the step of providing at one communicable and readable database; said database comprising absorption spectra of collected volatile compounds and/or aerosols captured in said membrane being scanned with an electromagnetic radiation in the THz range.

It is another object of the present invention to provide the method as defined above, wherein said volatile compounds and/or aerosols create spoof surface plasmon polaritons (SSPPs) captured in said membrane.

It is another object of the present invention to provide the method as defined above, wherein said virus is selected from a group selected from COV viruses family, COVID-19, Influenza, Avian influenza and any combination thereof.

It is another object of the present invention to provide the method as defined above, wherein said method is performed by a system being selected from a group consisting of a breathalyzer, any handheld device, any IOT device into which human breath is exhaled.

It is another object of the present invention to provide the method as defined above, wherein said data being processed by said control unit is at least one absorption spectrum of said membrane.

It is another object of the present invention to provide the method as defined above, wherein processing of said at least one absorption spectrum of said membrane additionally comprising pattern recognition of said at least one absorption spectrum.

It is another object of the present invention to provide the method as defined above, wherein said pattern recognition comprising at least one selected from a group consisting identification of special features of the pattern, identification of main and side peaks, the number of main and side peaks, the width of the peaks and the distance therebetween and any combination thereof.

It is another object of the present invention to provide the method as defined above, wherein said membrane is in communication with a vacuum source, a gas collection device coupled to the vacuum source, wherein the membrane is capable of capturing volatile compounds and/or aerosols.

It is another object of the present invention to provide the method as defined above, wherein said membrane is cleaned by applying at least one selected from a group consisting of positive/negative pressure or electricity to release said VCs and/or aerosols.

It is another object of the present invention to provide the method as defined above, wherein said membrane is coated with at least one material selected from a group consisting of Silicon, or Silicon Graphene, acting as a reflector, and any combination thereof.

It is another object of the present invention to provide the method as defined above, wherein said membrane is made of at least one material selected from a group consisting of Meta-Material Membrane, Semi Pressure Permeable Membrane, meta-material, PET, open-cell foam-based melamine and any combination thereof.

It is another object of the present invention to provide the method as defined above, additionally comprising an electromagnetic radiation transmitter and detector.

It is another object of the present invention to provide the method as defined above, wherein the membrane is positionable within the electromagnetic radiation emitted by the transmitter.

It is another object of the present invention to provide the method as defined above, additionally comprising at one communicable and readable database; said database comprising collected volatile compounds and/or aerosols being scanned with an electromagnetic radiation in the THz range.

It is another object of the present invention to provide the method as defined above, wherein said method has 2 modes of operation: (a) a learning phase; and, (b) a detection phase.

It is another object of the present invention to provide the method as defined above, wherein, in said learning phase, said control unit trains a machine learning model to detect at least one parameter in the absorption spectrum of said membrane with said collected volatile compounds and/or aerosols being scanned with an electromagnetic radiation in the THz range of a plurality of membrane stored in said communicable and readable database in order to generate information data being indicative of said virus free individuals.

It is another object of the present invention to provide the method as defined above, wherein aid parameter selected from a group consisting of, trends in said database of said at least one tested individuals, eigenvector of said database of said at least one tested individuals, eigenvalues of said database of said at least one tested individuals, feature extraction step being configured to estimate the most relevant vectors defining the data using a principal component analysis, a pattern classification using a combined linear and nonlinear pattern recognition approach, known symptoms of said virus, known healthy individuals, healthy individual vital signs selected from fever, sweat, body temperature, blood pressure, pulse (heart rate), and breathing rate (respiratory rate) and any combination thereof, virus free individual vital signs selected from fever, sweat, body temperature, blood pressure, pulse (heart rate), and breathing rate (respiratory rate) and any combination thereof, medicaments being administered to said tested individual, and any combination thereof.

It is another object of the present invention to provide the method as defined above, wherein, in said learning phase, said data is either supervised or unsupervised data; and, said training by said control unit is performed by at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds and/or aerosols being scanned with an electromagnetic radiation in the THz range stored in said communicable and readable database in order to generate information data being indicative of at least one said virus free individuals.

It is another object of the present invention to provide the method as defined above, wherein, in said detection phase, said data is either supervised or unsupervised data; and, said control unit performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds and/or aerosols being scanned with an electromagnetic radiation in the THz range stored in said communicable and readable database in order to generate information data being indicative of at least one said virus free individuals.

It is another object of the present invention to provide the method as defined above, wherein, in said detection phase, said control unit detects said signature the absorption spectrum of said membrane with said VCs and/or aerosols being indicative of at least one said virus free individuals by means of said trained machine learning model.

It is another object of the present invention to provide the method as defined above, additionally comprising at least one communicable and readable database storing instructions which, when executed by the at least one data processor, result in operations comprising training a machine learning model to detect at least one parameter of said collected volatile compounds and/or aerosols being scanned with an electromagnetic radiation in the THz range of at least one tested individuals stored in said communicable and readable database in order to generate information data being indicative of said virus free individuals; and, after said step of training, real time detecting said parameter by means of said trained machine learning model.

It is another object of the present invention to provide the method as defined above, wherein said control unit additionally performs Fast Fourier Transformation in order to generate information data being indicative of said virus free individuals.

It is another object of the present invention to provide the method as defined above, wherein said membrane is made of hardened extruded plastic.

It is another object of the present invention to provide the method as defined above, wherein said membrane is able to trap at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane (CH4), Carbon dioxide (CO2), Nitrous oxide (N2O), Ozone (O3), Chlorofluorocarbons (CFCs), Hydrofluorocarbons (includes HCFCs and HFCs), NO, NO2, viral proteins, cellular debris, debris of said virus, hydrates of said virus, hydrates of debris of said virus, hydrates of the 3D structure of said virus and a cell, aggregates of said virus, cytokines, increased level of interleukin interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the method as defined above, wherein said membrane is single-use, disposable membrane.

It is another object of the present invention to provide the method as defined above, wherein said membrane is reusable.

It is another object of the present invention to provide the method as defined above, wherein said membrane is removable from the sampling apparatus.

It is another object of the present invention to provide the method as defined above, further comprising a spectroscopic assembly including a radiation transmitter unit being configured and operable to scan said membrane holding the collected volatile compounds and/or aerosols by generating an electromagnetic radiation in the range of THz within a scanning window of about 100 GHz and a detection unit being configured and operable to detect an electromagnetic radiation emitted by said collected volatile compounds and/or aerosols.

It is another object of the present invention to provide the method as defined above, additionally comprising signaling means adapted to signal the user that sufficient enough of VCs and/or aerosols have been captured in said membrane or that said detection has been completed.

It is another object of the present invention to provide the method as defined above, wherein said signaling means are either optical or vocal means.

It is another object of the present invention to provide the system as defined above, utilized for homeland security applications.

It is another object of the present invention to provide the system as defined above, utilized in public places selected from airports, schools, public clinic, convention centers, parks, kindergartens, stadiums and any combination thereof.

It is another object of the present invention to provide the system as defined above, utilized for homeland security applications.

It is another object of the present invention to provide the system as defined above, utilized in public places selected from airports, schools, public clinic, convention centers, parks, kindergartens, stadiums and any combination thereof.

It is another object of the present invention to provide the sampler as defined above, utilized in a system for homeland security applications.

It is another object of the present invention to provide the sampler as defined above, utilized in a system for public places selected from airports, schools, public clinic, convention centers, parks, kindergartens, stadiums and any combination thereof.

It is another object of the present invention to provide the method as defined above, utilized for homeland security applications.

It is another object of the present invention to provide the method as defined above, utilized in public places selected from airports, schools, public clinic, convention centers, parks, kindergartens, stadiums and any combination thereof.

It is another object of the present invention to provide the method as defined above, utilized for homeland security applications.

It is another object of the present invention to provide the method as defined above, utilized in public places selected from airports, schools, public clinic, convention centers, parks, kindergartens, stadiums and any combination thereof.

It is another object of the present invention to provide the method or system or sampler as defined above, additionally comprising at least one filter disposed on said membrane.

It is another object of the present invention to provide the method or system or sampler as defined above, wherein said filter is adapted to affect the absorption signal detected in the absorption spectrum when said VCs and/or aerosols are absorbed on said membrane.

It is another object of the present invention to provide the method or system or sampler as defined above, wherein said filter is at least one selected from a group consisting of ring resonator, directional antenna, antenna, band-stop filter, notch filter and any combination thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In order to understand the invention and to see how it may be carried out in practice, embodiments will now be described, by way of non-limiting example only, with reference to the accompanying drawings. Features shown in the drawings are meant to be illustrative of only some embodiments of the invention, unless otherwise implicitly indicated. In the drawings like reference numerals are used to indicate corresponding parts, and in which:

FIG. 1b schematically illustrates the exemplary embodiment of FIG. 1a.

FIG. 1c schematically illustrates the exemplary embodiment of FIG. 1a.

FIG. 1d schematically illustrates the exemplary embodiment of FIG. 1a.

FIG. 1e schematically illustrates the exemplary embodiment of FIG. 1a.

FIG. 1f schematically illustrates the exemplary embodiment of FIG. 1a.

FIG. 1g schematically illustrates the exemplary embodiment of FIG. 1a.

FIG. 5f schematically illustrates another exemplary embodiment of the sampler and/or method of sampling with the same.

FIG. 5g schematically illustrates another exemplary embodiment of the sampler and/or method of sampling with the same.

FIG. 5h schematically illustrates another exemplary embodiment of the sampler and/or method of sampling with the same.

FIG. 9a illustrates a schematic of a sampler according to an exemplary embodiment.

FIG. 9i illustrates performance of the sampler.
FIG. 9j illustrates performance of the sampler.
FIG. 9k illustrates performance of the sampler.
FIG. 9l illustrates performance of the sampler.
FIG. 9m illustrates performance of the sampler.
FIG. 9o illustrates performance of the sampler.

FIG. 9t illustrates contour plots of the sampler performance.

DETAILED DESCRIPTION

Figure 1A:
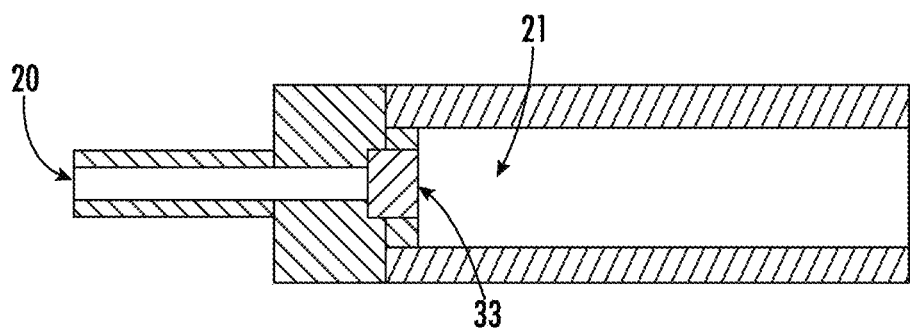
FIG. 1a schematically illustrates an exemplary embodiment of the sampler and the membrane therewithin.

Because the illustrated embodiments of the present invention may, for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.
Any reference in the specification to a method should be applied mutatis mutandis to a system capable of executing the method. Conversely, any reference in the specification to a system should be applied mutatis mutandis to a method that may be executed by the system.

The term "healthy individual" refers hereinafter to a CoV free individual (namely COVID-19 free individual) and/or recovered Cov individual (namely COVID-19 recovered individual).

The term "Coronaviruses (CoV)" refers to a large family of viruses that cause illness ranging from the common cold to more severe diseases such as Middle East Respiratory Syndrome (MERS-CoV) and Severe Acute Respiratory Syndrome (SARS-CoV).

The term "Coronavirus disease (COVID-19)" refers to a new strain of the CoV family that was discovered in 2019 and has not been previously identified in humans.

Coronaviruses are zoonotic, meaning they are transmitted between animals and people. Detailed investigations found that SARS-CoV was transmitted from civet cats to humans and MERS-CoV from dromedary camels to humans. Several known coronaviruses are circulating in animals that have not yet infected humans.

Common signs of infection include respiratory symptoms, fever, cough, shortness of breath and breathing difficulties. In more severe cases, infection can cause pneumonia, severe acute respiratory syndrome, kidney failure and even death.

Standard recommendations to prevent infection spread include regular hand washing, covering mouth and nose when coughing and sneezing, thoroughly cooking meat and eggs, and avoiding close contact with anyone showing symptoms of respiratory illness such as coughing and sneezing.

The term "band-stop filter" or "band-rejection filter" refers hereinafter to a filter that passes most frequencies unaltered, but attenuates those in a specific range to very low levels. It is the opposite of a band-pass filter. A notch filter is a band-stop filter with a narrow stopband. Thus, a notch Filter is also known as a Band Stop filter or Band Reject Filter. These filters reject/attenuate signals in a specific frequency band called the stop band frequency range and pass the signals above and below this band. For example, if a Notch Filter has a stop band frequency from 1500 MHz to 1550 MHz, it will pass all signals from DC to 1500 MHz and above 1550 MHz. It will only block those signals from 1500 MHz to 1550 MHz.

The term "debris" or "cellular debris" refers hereinafter to organic waste left over after a cell dies by undergoing apoptosis or lysis.

The term "Influenza" or "the flu", is an infectious disease caused by an influenza virus. Three of the four types of influenza viruses affect humans: Type A, Type B, and Type C. Type D has not been known to infect humans, but is believed to have the potential to do so. Usually, the virus is spread through the air from coughs or sneezes. This is believed to occur mostly over relatively short distances. It can also be spread by touching surfaces contaminated by the virus and then touching the eyes, nose, or mouth. A person may be infectious to others both before and during the time they are showing symptoms. The infection may be confirmed by testing the throat, sputum, or nose for the virus. A number of rapid tests are available; however, people may still have the infection even if the results are negative. A type of polymerase chain reaction that detects the virus's RNA is more accurate.

It can be difficult to distinguish between the common cold and influenza in the early stages of these infections. Influenza symptoms are a mixture of symptoms of common cold and pneumonia, body ache, headache, and fatigue. Diarrhea is not usually a symptom of influenza in adults, although it has been seen in some human cases of the H5N1 "bird flu" and can be a symptom in children. The symptoms most reliably seen in influenza are shown in the adjacent table.

The specific combination of fever and cough has been found to be the best predictor; diagnostic accuracy increases with a body temperature above 38° C. (100.4° F.). Two decision analysis studies suggest that during local outbreaks of influenza, the prevalence will be over 70%. Even in the absence of a local outbreak, diagnosis may be justified in the elderly during the influenza season as long as the prevalence is over 15%.

The term "Avian influenza" refers hereinafter to a variety of influenza caused by viruses adapted to birds.

The term "common cold" or "cold" refers hereinafter to a viral infectious disease of the upper respiratory tract that primarily affects the nose. The throat, sinuses, and larynx may also be affected. Well over 200 virus strains are implicated in causing the common cold, with rhinoviruses being the most common. They spread through the air during close contact with infected people or indirectly through contact with objects in the environment, followed by transfer to the mouth or nose. There is no vaccine for the common cold. The primary methods of prevention are handwashing; not touching the eyes, nose or mouth with unwashed hands; and staying away from sick people.

The term "Viral protein" refers herein to both a component and a product of a virus. Viral proteins are grouped according to their functions, and groups of viral proteins include structural proteins, nonstructural proteins, regulatory, and accessory proteins. Viruses are non-living and they do not have the means to reproduce on their own. They depend on their host cell's metabolism for energy, enzymes, and precursors, in order to reproduce. Thus, viruses do not code for many of their own viral proteins, and instead use the host cell's machinery to produce the viral proteins they require for replication.

The term "Cytokines" refers herein to a broad and loose category of small proteins (~5-20 kDa) important in cell signaling. Cytokines are peptides, and cannot cross the lipid bilayer of cells to enter the cytoplasm. Cytokines have been shown to be involved in autocrine, paracrine and endocrine signaling as immunomodulating agents. Their definite distinction from hormones is still part of ongoing research.

Cytokines include chemokines, interferons, interleukins, lymphokines, and tumor necrosis factors, but generally not hormones or growth factors (despite some overlap in the terminology).

Cytokines are produced by a broad range of cells, including immune cells like macrophages, B lymphocytes, T lymphocytes and mast cells, as well as endothelial cells, fibroblasts, and various stromal cells; a given cytokine may be produced by more than one type of cell.

They act through receptors, and are especially important in the immune system; cytokines modulate the balance between humoral and cell-based immune responses, and they regulate the maturation, growth, and responsiveness of particular cell populations. Some cytokines enhance or inhibit the action of other cytokines in complex ways.

They are important in health and disease, specifically in host responses to infection, immune responses, inflammation, trauma, sepsis, cancer, and reproduction.

Over-secretion of cytokines can trigger a dangerous syndrome known as a cytokine storm.

Cytokines storms may have been the cause of severe adverse events during a clinical trial of TGN1412.

Cytokine storms are also suspected to be the main cause of death in the 1918 "Spanish Flu" pandemic. Deaths were weighted more heavily towards people with healthy immune systems, due to their ability to produce stronger immune responses, with dramatic increases in cytokine levels.

In the 2019-21 coronavirus pandemic, a number of deaths due to COVID-19 have been attributable to cytokine release storms.

The term "hypercytokinemia" refers herein to a potentially fatal immune reaction consisting of a positive feedback loop between cytokines and immune cells, with highly elevated levels of various cytokines.

The term "Cytokine release syndrome" or "cytokine storm syndrome (CSS)" refers herein to a form of systemic inflammatory response syndrome (SIRS) that can be triggered by a variety of factors such as infections and certain drugs. It occurs when large numbers of white blood cells are activated and release inflammatory cytokines, which in turn activate yet more white blood cells. CRS is also an adverse effect of some monoclonal antibody drugs, as well as adoptive T-cell therapies. Severe cases have been called cytokine storms.

In addition to adoptive T-cell therapies, severe CRS or cytokine reactions can occur in a number of infectious and non-infectious diseases including graft-versus-host disease (GVHD), coronavirus disease 2019 (COVID-19), acute respiratory distress syndrome (ARDS), sepsis, Ebola, avian influenza, smallpox, and systemic inflammatory response syndrome (SIRS).

Although, severe acute respiratory syndrome coronavirus 2 (SARS-CoV-2) is sufficiently cleared by the early acute phase anti-viral response in most individuals, some progress to a hyperinflammatory condition, often with life-threatening pulmonary involvement. This systemic hyperinflammation results in inflammatory lymphocytic and monocytic infiltration of the lung and the heart, causing ARDS and cardiac failure. Patients with fulminant COVID-19 and ARDS have classical serum biomarkers of CRS including elevated CRP, LDH, IL-6, and ferritin.

The term "Polymerase chain reaction (PCR)" refers herein to a method widely used in molecular biology to rapidly make millions to billions of copies of a specific DNA sample allowing scientists to take a very small sample of DNA and amplify it to a large enough amount to study in detail. Often, nucleic acids are readily labeled with tags that facilitate detection or purification.

Usually in PCR and/or in other biological testing methods biological labeling is required. Such labeling is a time-consuming technique. Thus, it could be advantageous to have a label-free testing method.

The term "PCR Ct" refers hereinafter to the PCR cycle number at which the sample's reaction curve intersects the threshold line. This value tells how many cycles it took to detect a real signal from the samples. Real-Time PCR runs will have a reaction curve for each sample, and therefore many Ct values. Ct values are inverse to the amount of target nucleic acid that is in the sample, and correlate to the number of target copies in the sample. Lower Ct values (e.g., below 34 cycles) indicate high amounts of target sequence. Higher Ct values (above 34 cycles) mean lower amounts of the target nucleic acid.

The term "humidity" refers hereinafter to the concentration of water vapor present in the air. The term "barometric pressure" refers hereinafter to the pressure within the atmosphere of Earth.

The term "high throughput" refers hereinafter to the use of equipment, automation equipment or partial thereof to permit rapid, highly parallel research or to provide results of the tests being conducted. It could address biological questions that are otherwise unattainable using conventional methods. It may incorporate techniques from optics, physics, chemistry, biology or image analysis.

The term "Metamaterial" refers herein to any material engineered to have a property that is not found in naturally occurring materials. They are made from assemblies of multiple elements fashioned from composite materials such as metals and plastics. The materials are usually arranged in repeating patterns, at scales that are smaller than the wavelengths of the phenomena they influence. Metamaterials derive their properties not from the properties of the base materials, but from their newly designed structures. Their precise shape, geometry, size, orientation and arrangement gives them their smart properties capable of manipulating electromagnetic waves: by blocking, absorbing, enhancing, or bending waves, to achieve benefits that go beyond what is possible with conventional materials.

Appropriately designed metamaterials can affect waves of electromagnetic radiation or sound in a manner not observed in bulk materials. Those that exhibit a negative index of refraction for particular wavelengths have attracted significant research. These materials are known as negative-index metamaterials.

The term "Polyethylene terephthalate, PET" refers herein to the most common thermoplastic polymer resin of the polyester family and is used in fibers for clothing, containers for liquids and foods, thermoforming for manufacturing, and in combination with glass fiber for engineering resins.

Pet's structure is given in the following formula, Formula I:

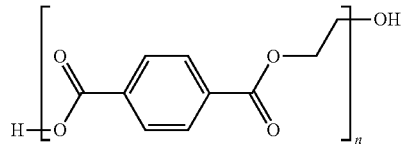

Formula I

The term 'Linear discriminant analysis' (LDA), refers herein after to a normal discriminant analysis (NDA), or discriminant function analysis is a generalization of Fisher's linear discriminant, a method used in statistics, pattern recognition, and machine learning to find a linear combination of features that characterizes or separates two or more classes of objects or events. The resulting combination may be used as a linear classifier, or, more commonly, for dimensionality reduction before later classification. The present invention utilizes Fisher's linear discriminant and/or Fisher's nonlinear discriminant.

In pattern recognition, the term "k-nearest neighbors algorithm (k-NN)" refers to a non-parametric method used for classification and regression. In both cases, the input consists of the k closest training examples in the feature space. The output depends on whether k-NN is used for classification or regression:

In k-NN classification, the output is a class membership. An object is classified by a plurality vote of its neighbors, with the object being assigned to the class most common among its k nearest neighbors (k is a positive integer, typically small). If k=1, then the object is simply assigned to the class of that single nearest neighbor.

In k-NN regression, the output is the property value for the object. This value is the average of the values of k nearest neighbors.

k-NN is a type of instance-based learning, or lazy learning, where the function is only approximated locally and all computation is deferred until classification.

Both for classification and regression, a useful technique can be to assign weights to the contributions of the neighbors, so that the nearer neighbors contribute more to the average than the more distant ones. For example, a common weighting scheme consists in giving each neighbor a weight of 1/d, where d is the distance to the neighbor.

The neighbors are taken from a set of objects for which the class (for k-NN classification) or the object property value (for k-NN regression) is known. This can be thought of as the training set for the algorithm, though no explicit training step is required.

A peculiarity of the k-NN algorithm is that it is sensitive to the local structure of the data.

The present invention relates to the use of Terahertz (THz) in detection of healthy (Covid-19 free or recovered) individuals vs. Covid-19 infected individuals. The term "THz radiation" generally refers herein below to any of the electromagnetic wave frequencies that lie in the range extending from around 100 GHz to 30 THz.

The use of THz has great advantages over IR and UV as the sensitivity and the detection threshold is very low thus, can detect information relating to Covid-19 (as will be described herein below), at very early stages thereof. IR and UV can detect information relating to Covid-19 at very late stages of the disease.

The information that can be detected is selected from a group consisting of cell unit of said virus, viral proteins, cellular debris, debris of said virus, hydrates of said virus, hydrates of debris of said virus, hydrates of the 3D structure of said virus and a cell, aggregates of said virus, cytokines, increased level of interleukin (IL)-2, IL-7, granulocytecolony, stimulating factor, interferon-γ, inducible protein 10, monocyte chemoattractant, protein 1, macrophage, inflammatory protein 1-α, and tumor necrosis factor-α and any combination thereof.

The advantages of the present invention include, inter alia, the following: Early Detection of Asymptomatic carriers of COVID-19; Fast Coronavirus Test detection—up to 1 minute; preferably less than 40 sec; High Throughput—800-1,500/Tests/Day; and, Non-Invasive—the testing includes blowing several times into the sampler.

The present invention provides a label free, noncontact, non-invasive method for the detection of COVID-19, without the need to amplify the DNA sample, 1st, 2nd and 3rd virus waves of the infection.

The term "collected media" refers hereinafter to any volatiles compound, VC, and/or aerosol and/or any chemical and biological compounds transmitted airborne that were released in the breath by at least one individual being tested.

The term "volatiles" or "volatiles compound" or "VCs" generally refers herein below to volatile compound and/or mix of compounds. According to at least one embodiment, the VCs can be organic compound and/or mix of compounds or inorganic compound and/or mix of compounds. It is also within the scope of the present invention wherein the VC is a mix of organic and inorganic compound\s.

The present invention provides a label free, noncontact, non-invasive method for the detection of COVID-19, without the need to amplify the DNA sample, 1st, 2nd and 3rd virus waves of the infection.

Furthermore, the present invention provides a breathalyzer or breathalyzer-like device that will enable the detection of COVID-19 in the exhaled breath of humans. There are many advantages thereto. As the COVID-19 is infectious by droplets and contact, testing the infectious agent in the breath and not from the blood stream is advantageous. Furthermore, as will be explained in the below, the severity of the disease can be diagnosed.

The present invention provides a membrane metamaterial absorber for different virus detection based on detection of trends of spoof surface plasmon polaritons (SSPPs) in THz band. The exhaled breath of humans will contain VCs and/or aerosols that will be captured in the membrane (e.g., made of PET or open-cell foam-based melamine) and will create SSPPs. Detection of specific trends in the absorption spectrum in THz bands.

The term "Surface plasmon polaritons (SPPs)" are a special type of surface wave (highly localized) that exists on the interface of two media (e.g., metal-dielectric) with opposite permittivities at optical frequencies. In the optical regime, the electromagnetic (EM) field of incident waves interacts with the plasma of electrons near the surface of the metal and therefore excites collective oscillations propagating along the interface. The interaction is so strong that the EM field is tightly confined to the interface.

SPPs are not supported below the far-infrared frequency because the strong field confinement no longer exists. In fact, at lower frequencies, metals behave close to perfectly electric conductors (PECs) rather than plasmas at optical frequencies. The first "artificial" surface plasmon polaritons are termed as the spoof SPPs.

To produce spoof SPPs at Terahertz frequencies, plasmonic metamaterials are utilized to provide subwavelength structures on a metal surface. Spoof SPPs inherit the properties of natural SPPs, including dispersion characteristics, field confinement, and subwavelength resolution, and therefore are highly expected to offer new solutions for advanced circuits and systems with high integration, compact size, and excellent performance.

Strongly confined SSPPs modes (caused by the VCs and/or aerosols of exhaled breath) are extracted from the absorption spectra of biosensing metamaterial absorber associated with local field enhancement. Identification of trends in said absorption spectrum together with refractive index libraries will provide identification and detection of the virus.

Thus, the provision of a membrane metamaterial absorber integrated within a breathalyzer for the detection of trends or signature of spoof SPPs (created by the VCs and/or aerosols of exhaled breath) at Terahertz frequencies of human breath provides a non-invasive, non-contact, label free detection of the COVID-19.

The different trends will be detected by comparing the absorption spectrum of healthy tested individuals vs. infected ones. For the comparison of both the absorption spectra, the inventors of the present invention believe that detection of COVID-19 infected or COVID-19-free (healthy) individuals can be identified.

Thus, according to another embodiment, THz technology enables the detection of COVID-19 infected or COVID-19-free (healthy) individuals, by means of label-free, noncontact, noninvasive, and nondestructive method.

The technique of the present invention is capable of detecting a trends in the absorption spectrum of spoof surface plasmon polaritons (SSPPs) (captured in the membrane and created due to VCs and/or aerosols in the exhaled breath of health people) due to the THz spectroscopy technique being capable of detection of materials/compounds at very low concentrations, below PPB (parts per billion).

Volatiles emitted from the breath convey information on the person being infected with COVID-19 or a healthy one. Said VCs and/or aerosols will be captured in the membrane (e.g., made of PET or open-cell foam-based melamine) can cause the creation of SSPPs. The membrane will be irradiated with THz frequencies and the absorption spectrum thereof will be analyzed. The same is true for healthy individuals. By identifying different trends, the identification of COVID-19 infected or COVID-19 free (healthy) people could be identified.

In general, a membrane metamaterial absorber for different virus detection in THz band will be integrated in a breathalyzer. The identification of strongly confined SSPPs modes, extracted from the absorption spectra of biosensing metamaterial absorber, like trends signature, will provide identification and detection of the virus' infected and virus-free (healthy) individuals; namely in COVID-19.

The proposed THz biosensing metamaterial absorber chip will perform ultrasensitive, high resolution detection by extracting the shifted resonance frequencies ($\Delta F$) and the changed values at maximum absorptions ($\Delta A$). Each virus species will have a dedicated fingerprint signature in terms of the $\Delta F$ and $\Delta A$.

Furthermore, the absorption will provide an indication as to the severity of the disease.

According to at least one embodiment, the collection system (the breathalyzer) will comprises the membrane biosensing chip and an integrated THz detection by means of a VCSEL (Vertical Cavity Surface Emitting Laser) that can be implemented in handheld devices.

According to another embodiment, the collection system (the breathalyzer) will be in communication with a THz detection system.

The membrane can be a pressure permeable membrane (e.g., Meta-Material Membrane (MMM) or Semi Pressure Permeable Membrane, e.g., meta-material PET or open-cell foam-based melamine based membrane).

Vacuum can also be applied to accelerate the flow of the air (from the exhaled air). Then, after the exhaled air has been sampled, the membrane are scanned with THz waves and the specific is detected based.

Therefore, according to a broad aspect of the present invention, there is provided a system for detecting COVID-19 infected or free (healthy) people by means of the detection of trends in the absorption spectra of said metamaterial absorber membrane by scanning thereof with electromagnetic radiation in the THz range.

Thus, the membrane (with the collected SSPPs from the breath trapped therewithin) is scanned with an electromagnetic radiation in the THz range, and processing the data for identifying a signature being indicative of at least one COVID-19 property to thereby generate information data being indicative of at least one COVID-19 infected or free (healthy) individuals.

The terms "membrane metamaterial absorber" or "biosensing metamaterial absorber chip" refer to a membrane being capable of trapping collected SSPPs and VCs and/or aerosols from a human breath therein. According to at least one embodiment, the membrane is integrated in a breathalyzer. According to at least one embodiment, the membrane is made of PET or open-cell foam-based melamine and any combination thereof. According to at least one embodiment, the membrane is placed in a PTFE (Polytetrafluoroethylene, aka. Teflon) disposable holder. According to at least one embodiment, the membrane integrated in the membrane housing into the sample, and after the air breath is taken, the membrane housing (and the membrane) is inserted into a dedicated capsule (which will be scanned by means of the THz scanner). According to at least one embodiment, the capsule is a disposable, sterile PTFE (Polytetrafluoroethylene, aka. Teflon)—based capsule.

The term "sampler" or "disposable, hand-held tube" refers hereinafter to the sampler with which the breath sample from the tested individual is taken. According to at least one embodiment, the sampler is made of polyoxymethylene-based (aka Delrin).

The term "Leave One Out (LOO)" refers hereinafter to a statistical method that is used to evaluate the efficacy of any classification procedure, with a relatively low number of samples, in order to teach and train spectroscopy systems to analyze spectral vectors. According to this machine learning method, the training is performed repeatedly, each time after excluding one training sample from the training data of the group, and then testing on those individual vectors that were excluded from training. Based on that specific learning process of LOO, a prediction is made for the left-out spectra and compared to the actual PCR results.

The term "Principal Component Analysis" refers hereinafter to mathematical technique. According to said technique, the mean (symbol below as "m") is subtracted from each spectrum (after being normalized by its associated reference) and the covariance (symbol below as small sigma as standard deviation) matrix of the combined spectra is computed. The eigen-values of this matrix are found, and the largest values are used to compute their respective eigen-vectors. This procedure is essentially a linear transformation of the normalized spectra into a set of vectors that best represent the training samples and are less prone to noise. These eigen-vectors (also called feature vectors) are then used to obtain a set of co-efficient vectors, one for each input spectrum, whose length equals the number of the feature vectors selected.

Thus, it is an object of the present invention to provide means and method for distinguishing between COVID-19 infected people and healthy ones.

The inventors of the present invention found that each individual has a unique mixture of VCs and/or aerosols which may be identified with THz technology. Thus, a healthy individual and a COVID-19 infected individual will have a different VC or different mixture thereof.

According to at least one embodiment, in general, the tested individuals are sampled in the breathalyzer (it could be aided by the use of vacuum suction), and the VCs and/or aerosols are trapped in a pressure dischargeable membrane (e.g., Meta-Material Membrane (MMM) Semi Pressure Permeable Membrane, e.g., meta-material PET or open-cell foam-based melamine based membrane), such that when the breath is exhaled by the human, the membrane is located at the propagation path of the VCs and/or aerosols released from the human.

The use of vacuum accelerates the flow of the volatiles and the use of the membrane provides for trapping the collected volatile compounds and/or aerosols within the membrane upon releasing the negative pressure (i.e. vacuum).

Then the membrane is scanned with THz waves and the specific VCs and/or aerosols for infected or healthy tested are detected based on the individual fingerprints trends in the adsorption. The membrane is then capable of releasing/discharging the trapped vapors by an operation including also positive or negative pressure.

Therefore, according to a broad aspect of the present invention, there is provided a system for detection of COVID-19 infected or free (healthy) individuals.

The system may also comprise a control unit configured and operable for receiving data indicative of the collected VCs and/or aerosols being scanned with an electromagnetic radiation in the THz range, and processing the data for identifying a signature being indicative of an infected COVID-19 individual and a healthy one.

According to at least one embodiment, a control unit is configured to receive and process the response signal emitted by the membrane and identify spectral special features indicative of a THz signature of the COVID-19 infected or free (healthy) individual. The inventors found that COVID-19 has its own THz signature. Thus, individual human can be distinguished from healthy ones. In some embodiments, the control unit is configured and operable for performing a pattern recognition of the THz signature. The control unit is configured generally as a computing/electronic utility including inter alia such utilities as data input and output utilities, memory, and data processing utility. The utilities of the control unit may thus be implemented by suitable circuitry and/or by software and/or hardware components including computer readable code configured for implementing the operations method.

The features of the present invention may comprise a general-purpose or special-purpose computer system including various computer hardware components, which are discussed in greater detail below. Features within the scope of the present invention also include computer-readable media for carrying or having computer-executable instructions, computer-readable instructions, or data structures stored thereon. Such computer-readable media may be any available media, which are accessible by a general-purpose or special-purpose computer system. By way of example, without limitation, such computer-readable media can comprise physical storage media such as RAM, ROM, EPROM, flash disk, CD-ROM or other optical disk storage, magnetic disk storage or other magnetic storage devices, or any other media which can be used to carry or store desired program code means in the form of computer-executable instructions, computer-readable instructions, or data structures and which may be accessed by a general-purpose or special-purpose computer system. Computer-readable media may include a computer program or computer application downloadable to the computer system over a network, such as a wide area network (WAN), e.g. Internet.

In this description and in the following claims, a "control unit" is defined as one or more software modules, one or more hardware modules, or combinations thereof, which work together to perform operations on electronic data. For example, the definition of processing utility includes the hardware components of a personal computer, as well as software modules, such as the operating system of a personal computer. The physical layout of the modules is not relevant. A computer system may include one or more computers coupled via a computer network. Likewise, a computer system may include a single physical device where internal modules (such as a memory and processor) work together to perform operations on electronic data. While any computer system may be mobile, the term "mobile computer system" or the term "mobile computer device" as used herein especially includes laptop computers, netbook computers, cellular telephones, smartphones, wireless telephones, personal digital assistants, portable computers with touch sensitive screens, and the like.

The control unit of the present invention may be implemented as part of a signal processing center, and/or as a portable (e.g. handheld) THz reading device. Data input utility includes a communication module for receiving the response THz signal, an optional data output utility for generating data relating to identified virus(s), a memory (i.e. non-volatile computer readable medium) for storing a learning database i.e. preselected data indicative of THz signatures of the Spoof SPPs and therefore of the virus, and a data processing utility adapted for identifying the COVID-19 infected or free (healthy) individuals. The database may be implemented with Microsoft Access, Cybase, Oracle, or other suitable commercial database systems. In some embodiments the system is configured in a cloud-based configuration and/or utilize Internet based computing so that parts of processing utility, and/or memory may reside in multiple distinct geographic locations. After the THz response signal(s) is/are received, the data processing utility is enabled to process the signal(s). Results of the signal processing step may be displayed and/or stored in storage and/or sent to a data communication unit for transfer to a sorting device. The memory may include instructions executable by data processing utility. The instructions may be operable to enable data processing utility to receive the THz response signal(s), to process the THz response signal (s), to identify at least one fingerprint signature of the absorption spectrum of a membrane to which VC (from the exhaled breath of human) will be captured therewithin (to create Spoof SPPs). Thereafter the membrane will be irradiated with THz frequencies. The absorption spectrum will be analyzed to find trends indicative of the virus, and to output via the data output utility a notification regarding the detection or failure to detect the virus (i.e., the infected with COVID-19 individuals). Memory and may be relayed via wireless or wired connection by an external unit to a central database.

In some embodiments, the control unit activates a spectroscopy assembly configured and operable for obtaining the THz signature. Spectroscopic assembly may or may not be a part of the system of the present invention. According to one embedment of the present invention, the system is a breathalyzer and the spectroscopy assembly (in the THz range) is integrated within the system. In such an embodiment, the THz capabilities are based on a VCSEL (Vertical Cavity Surface Emitting Laser) and can be integrated in TOT devices as well as handheld devices. Alternatively, the spectroscopy assembly in not integrated in the system and the absorption spectrum is communicated to said spectroscopy assembly to be analyzed.

The processing utility signals to THz radiation transmitter unit to emit THz radiation passing though the membrane (being in the optical path of the THz radiation). Data input receives a radiation signal pattern via radiation detection unit. The radiation signal pattern is the radiation that was not adsorbed by the membrane. The radiation signal pattern contains the THz signature. Processing utility may transmit data regarding the signal pattern via the data output utility, via a data communication (e.g. via cellular network) to a communication module of a central computer. The processing utility may record the received data in a learning database in memory and/or may query/cross-reference the received data with data in the learning database to identify virus properties and may communicate such data to a mobile device at which processing utility may signal to display a message corresponding to the virus data. To this end, the preselected data stored in the learning database may be used to compare the THz pattern/signature of the VCs and/or aerosols (captured in the membrane and created the Spoof SPPs) with the signatures or trends stored in the learning database.

The membrane metamaterial absorber may be a pressure permeable membrane configured as a dense, compressed structure made of fibers (e.g. mesh) such that the pressure permeable membrane responds to the application/release of vacuum as a pressure dischargeable membrane. The membrane metamaterial absorber may be configured as a metamaterial membrane being a material deriving its properties not from the properties of the basic materials, but from its designed structure. The metamaterial membrane may comprise a plurality of layers of metamaterial encapsulated in a plastic housing, produced with an accuracy of ±10 microns.

In some embodiments, the system (breathalyzer) includes a spectroscopic assembly including a radiation transmitter unit being configured and operable to produce THz frequency radiation and a detection unit being configured and operable to detect an electromagnetic radiation emitted/influenced by the spoof surface plasmon polaritons (SSPPs) and/or the VCs and/or aerosols captured in the membrane.

In particular, according to at least one embodiment, the radiation transmitter unit is operable for irradiating the membrane with a radiation having a wavelength in the range extending from around 100 GHz to 30 THz and to scan the membrane within a scanning window of about 100 GHz. Although, for the sake of clarification, the radiation transmitter unit and the detection unit are represented as two separate physical elements, they can be integrated in the same physical element or in the same housing. In a specific and non-limiting example, radiation transmitter unit is configured and operable for generating inspecting and reference electro-magnetic radiation components of substantially the same frequency contents, and for sweeping/scanning the frequency. Detection unit may be located in a first path of the inspecting radiation components after passing through the membrane and in a second path of the reference radiation component directly propagating from the transmitter unit. The spectroscopic assembly may be configured to induce a predetermined frequency difference between a frequency of the inspecting radiation component and the reference radiation component interacting at the detection unit such that a signal resulting from the interaction between the inspecting and reference components is indicative of one or more properties of the virus at a location where the inspecting radiation interacts with the membrane.

The system (breathalyzer) of the present invention may comprise the spectroscopy assembly as described above or may directly receive data emitted by the VCs and/or aerosols (and/or the spoof surface plasmon polaritons (SSPPs)) in the membrane obtained by an external spectroscopy assembly as described above or as conventionally used in the field. The spectroscopy systems include photo-mixing, heterodyne detection, and chirped-pulse THz spectroscopy. Another spectroscopy method is to use the THz resonance field in a photonic crystal, a waveguide device or frequency multiplier.

In some embodiments, the system is connectable to a communication network with a host computer, which is external to the control unit. Alternatively, the spectroscopic assembly can be also attached to the control unit by using a coupling member of any type. The control unit is configured and operable to control the operation of the spectroscopic assembly. The control unit may be integrated within the spectroscopic assembly or may be a separate element communicating with the spectroscopic assembly via wired or wireless communication. If the control unit is integrated within the spectroscopic assembly, THz signature identification does not require or employ any type of electronic components, circuitry or antenna. It should be appreciated, that signal exchange and communication is enabled between the modules of the system by virtue of appropriate wiring, or wirelessly. For example, the spectroscopic assembly and the control unit can be connected by IR (Infra-Red), RF (radio frequency including Bluetooth) or cable control. If the spectroscopic assembly and the control unit are integrated in the same physical housing, the THz signature is stored in the control unit. The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections, and vice versa. Also, a plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Moreover, in some embodiments, the thickness of the membrane may be selected to be at least several times (e.g. at least four times) the wavelength of the electromagnetic radiation. The thickness should be selected to be sufficiently wide to enable to capture a sufficient amount of spoof surface plasmon polaritons (SSPPs) allowing to perform an analysis providing an identifiable THz signature.

It should be noted that the THz signature is sensitive to low changes in the vapor composition and provides a detection with high resolution. The high resolution of the THz signature enables to differentiate between signatures of different viruses. If the resolution of the signature is not good enough, the THz signatures would overlap and a differentiation between them is then impossible. By contrast, the use of infrared radiation does not provide an identifiable signal. A spectroscopic analysis using an infrared radiation including the collection of the gas and the separation of the different chemical components, yields poor results. Moreover, the high rate of gas delivery required by the infrared spectroscopy does not permit collection of the carrier and separated components in a small area. In some embodiments, prior to step of trapping the VCs and/or aerosols within the membrane (by the exhaled breath), the detection method may comprise the step of obtaining a reference spectrum by performing a THz spectroscopy on a reference clean membrane. In some embodiments, the method may comprise the step of cleaning a membrane having trapped VCs and/or aerosols for a further use by applying a positive/negative pressure.

In some embodiments, the method may further comprises a step of recording a THz signature in the learning database. The learning database may be configured to provide a THz fingerprint/signature associated with the one or more absorption spectrum of VCs and/or aerosols from COVID-19 infected or free (healthy) individuals. For example, the method may include storing in the learning database preselected data indicative of the signature of the signal and/or properties of the VCs and/or aerosols associated with COVID-19 infected or free (healthy) individuals with the signature. The step of processing the data may further include comparing the received THz data to data in the learning database. Received THz data may be logged in a learning database. Logged received THz data may be used for future analyses of future viruses.

Optionally, step of processing the data may further include assessing one or more properties of the trends in absorption spectrum of VCs and/or aerosols or spoof surface plasmon polaritons (SSPPs) as indicative to the COVID-19 infected or free (healthy) individuals, based on the learning database data. Assessing one or more properties may be performed using a statistical analysis in which received THz data is compared to learning database THz data and a statistical comparison is performed. If a predetermined level of similarity is shown, the THz data is considered to have a certain property.

More specifically, the processing of the control unit comprises the step of providing a mathematical interpretation of pattern recognition based on a learning algorithm such as a Neural Network Acceleration algorithm (NNA). The interpretation of the pattern recognition is based on identification of special features of the pattern such as the identification of main and side peaks, the number of main and side peaks, the width of the peaks and the distance between them.

According to another embodiment, the membrane with be coated with Silicon or Silicon Graphene, acting as a reflector, to enhance the signal.

In some embodiments, the processing step, may comprise the following steps: an optional preprocessing step being configured to remove irrelevant spectral trends present in the measurements, and to filter out random measurement noise; a feature extraction step being configured to estimate the most relevant vectors defining the data using a principal component analysis; and a pattern classification step using a combined linear and nonlinear pattern recognition approach.

In a specific and non-limiting example, the optional preprocessing step may include the step of establishing the learning database. The step of establishing the learning database may comprise the steps of collecting the scans, preprocessing the scans as described above, and performing a Fourier Transformation on the results. The feature extraction step may include the step of subtracting a reference processed data from the sample processed data. The resulting data belongs to or represents only VCs' and/or aerosols' virus related information (without data relating to the membrane). The step of subtracting the reference processed data (e.g. membrane results) from the sample processed data (e.g. virus sample results) may be followed by a step of performing a second Fourier transformation on the virus related information to provide the specific virus related signals.

The pattern classification step may include the steps comparing all the obtained results to the learning database. When the learning database is established, the same sampled membrane are tested biologically by Polymerase Chain Reaction (PCR) method for the COVID-19 detection.

As described above, the absorption spectra is read and compared to a database via software matching algorithms. The database contains spectral fingerprints of the trends in the absorption spectra (obtained from scanning the membrane with the VCs and/or aerosols captured therewithin) with a specified signature or trend/s therewithin representing detection of COVID-19 infected or free (healthy) individual. In a particular embodiment, terahertz radiation within the 200-1200 GHz range is used. The software matching algorithm compares the collected spectrum to the catalogued fingerprint within pre-determined confidence bounds, and detects the virus by determining whether or not the read spectrum falls within the error bounds of the fingerprint.

In an embodiment, membranes may be recycled via application of electricity to release the VCs and/or aerosols and/or spoof surface plasmon polaritons (SSPPs) from the membrane. The "cleaned" membrane is cycled back into place on the sampling apparatus. In other embodiments, the membrane can be cleaned by reversing the flow of the vacuum motor, which causes air to pass through the membrane and push the absorbed molecules from the membrane. In certain embodiments, each membrane may be used only once and then replaced by a new membrane.

The mathematical analysis is described below. After establishing the learning data base, all next measured data is compared to the learning database by using the same mathematical process. The inventors of the present invention have found that different THz signatures being indicative of different properties of viruses can be detected. Thus, the present invention can detect VCs and/or aerosols from infected or free (healthy) COVID-19 individual. The inventors of the present invention believe that the identification of the special features of the pattern such as the number of peaks, the distance between the main peaks, the identification of main and side peaks, the width of the peaks enables to define the properties of the virus. In other words, the inventors have found that obtaining a ratio between the THz signatures of different membrane enables identification of infected and healthy individuals.

By utilizing a Neural Network Analysis (NNA) system which is based on machine-learning ability, the system will continuously improve with each additional performance as database (DB) grows. The learning process is essential to "educate" the system to include more spectral variations within its solution space. In order to improve the predication, the sampling size has to be increased so the statistics will be able to validate for the model.

According to at least one embodiment, Leave One Out (LOO) algorithm is the one of the methods that could be used for the analysis of the Terahertz spectra detection, in order to provide accurate detection of the virus.

It is acknowledged that LOO is a statistical method used to evaluate the efficacy of any classification procedure, with a relatively low number of samples, in order to teach and train spectroscopy systems to analyze spectral vectors. According to this machine learning method, the training is performed repeatedly, each time after excluding one training sample from the training data of the group, and then testing on those individual vectors that were excluded from training. Based on that specific learning process of LOO, a prediction is made for the left-out spectra and compared to the actual PCR results.

The actual classification of each spectral vector is made by either using a linear classification method (see Fisher R. A. The Use of Multiple Measurements in Taxonomic Problems. Annals of Eugenics, 7 Part II:179-188, 1936) or using the Mahalanobis distance classifier (see Mahalanobis, P. C.

On the generalized distance in statistics. Proceeding of the National Institute of Sciences of India. 2(1):49:55). Both methods use the classes' means and covariances to assign each input vector to its own class based on its multi-dimensional distances from each class. Therefore, the results obtained clearly indicate that this procedure is adequate for classifying unseen spectra into their associated classes, with a high probability of detection and low "false-alarm" rates.

According to another embodiment, the method is based on a "Principal Component Analysis" (see Konstantinos, I. D. and Sun-Yuang, K. Principal Component Neural Networks: Theory and Applications. Wiley-Inter-science, New York, 1996). According to this mathematical technique, the mean (symbol below as "m") is subtracted from each spectrum (after being normalized by its associated reference) and the covariance (symbol below as small sigma as standard deviation) matrix of the combined spectra is computed. The eigen-values of this matrix are found, and the largest values are used to compute their respective eigen-vectors. This procedure is essentially a linear transformation of the normalized spectra into a set of vectors that best represent the training samples and are less prone to noise. These eigen-vectors (also called feature vectors) are then used to obtain a set of co-efficient vectors, one for each input spectrum, whose length equals the number of the feature vectors selected.

The Principal Component Analysis is represented by the following formula:

$$J = \frac{(m_1 - m_2)^2}{(\sigma_1^2 + \sigma_2^2)}$$

where J is the power of separation between two groups, m1 and m2 are the means of each group, σ1 and σ2 are the standard deviations of each group, and the two groups are on a continuous measurement where m2=the value of m1 at one standard deviation.

The purpose of the spectral classification stage is to train the algorithm, by using a known set of spectra and then to classify previously unseen spectra into their respective classes, with a minimal number of errors. The target for 100% separation is J>19 (as shown in the equation above).

According to at least one embodiment, the membrane is made of hardened extruded plastic, containing pores of two specific sizes, and acting as Ketones trap. It should be noted that the compound could also be, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane (CH4), Carbon dioxide (CO2), Nitrous oxide (N2O), Ozone (O3), Chlorofluorocarbons (CFCs), Hydrofluorocarbons (includes HCFCs and HFCs), NO, NO2, aromatic alcohols, aldehydes and any combination thereof and not just Ketones.

According to another embodiment of the present invention is to provide a single-use, disposable membranes. According to another embodiment the membrane is reusable.

It should be noted that LDA, k-nearest neighbors algorithm (k-NN) algorithm can also be used as well as LOO.

As mentioned above, Terahertz (THz) radiation is known to interact with polar molecules via rotational or/and vibrational transition levels. These interactions are manifested as absorption. The frequency THz spectrum obtained by scanning the membrane is indicative of various chemical materials including volatile compounds, VCs, and/or aerosols having individual specific fingerprints or trends.

As described above, the control unit is configured to receive and process the response signal emitted by the testes individual and identify spectral special features indicative of a THz signature of the VCs and/or aerosols indicative of COVID-19 infected or free (healthy) individual. The information included in the THz signature is thus associated with the sorting process. The system (breathalyzer) is configured to be used with at least one tested individual with exhaled breath having VCs and/or aerosols with properties identifiable by THz inspection, such that upon examination by THz analysis, infected individuals or individuals who are COVID-19 free (healthy) may be identified. The inventors found that infected individuals and healthy ones have different THz signature.

In some embodiments, the control unit is configured and operable for performing a pattern recognition of the THz signature. The control unit is configured generally as a computing/electronic utility including inter alia such utilities as data input and output utilities, memory, and data processing utility. The utilities of the control unit may thus be implemented by suitable circuitry and/or by software and/or hardware components including computer readable code configured for implementing the operations of methods described below.

The features of the present invention may comprise a general-purpose or special-purpose computer system including various computer hardware components, which are discussed in greater detail below. Features within the scope of the present invention also include computer-readable media for carrying or having computer-executable instructions, computer-readable instructions, or data structures stored thereon. Such computer-readable media may be any available media, which are accessible by a general-purpose or special-purpose computer system. By way of example, without limitation, such computer-readable media can comprise physical storage media such as RAM, ROM, EPROM, flash disk, CD-ROM or other optical disk storage, magnetic disk storage or other magnetic storage devices, or any other media which can be used to carry or store desired program code means in the form of computer-executable instructions, computer-readable instructions, or data structures and which may be accessed by a general-purpose or special-purpose computer system. Computer-readable media may include a computer program or computer application downloadable to the computer system over a network, such as a wide area network (WAN), e.g. Internet.

In this description and in the following claims, a "control unit" is defined as one or more software modules, one or more hardware modules, or combinations thereof, which work together to perform operations on electronic data. For example, the definition of processing utility includes the hardware components of a personal computer, as well as software modules, such as the operating system of a personal computer. The physical layout of the modules is not relevant. A computer system may include one or more computers coupled via a computer network. Likewise, a computer system may include a single physical device where internal modules (such as a memory and processor) work together to perform operations on electronic data. While any computer system may be mobile, the term "mobile computer system"

or the term "mobile computer device" as used herein especially includes laptop computers, netbook computers, cellular telephones, smartphones, wireless telephones, personal digital assistants, portable computers with touch sensitive screens, and the like.

The control unit of the present invention may be implemented as part of a signal processing center, and/or as a portable (e.g. handheld) THz reading device. Data input utility includes a communication module for receiving the response THz signal, an optional data output utility for generating data relating to identified healthy individuals, infected ones, a memory (i.e. non-volatile computer readable medium) for storing a learning database i.e. preselected data indicative of THz signatures of the healthy individuals versus the infected ones, and a data processing utility adapted for identifying infected or healthy ones.

The database may be implemented with Microsoft Access, Cybase, Oracle, or other suitable commercial database systems. In some embodiments the system is configured in a cloud-based configuration and/or utilize Internet based computing so that parts of processing utility, and/or memory may reside in multiple distinct geographic locations.

After the THz response signal(s) is/are received, the data processing utility is enabled to process the signal(s). Results of the signal processing step may be displayed and/or stored in storage and/or sent to a data communication unit for transfer to a sorting device. The memory may include instructions executable by data processing utility. The instructions may be operable to enable data processing utility to receive the THz response signal(s), to process the THz response signal (s), to identify at least one property in the absorption spectrum of the membrane (captured with the VCs and/or aerosols), and to output via the data output utility a notification regarding if the individual is healthy or infected.

In some embodiments, the control unit activates a spectroscopy assembly configured and operable for obtaining the THz signature. Spectroscopic assembly may or may not be a part of the system of the present invention. The processing utility signals to THz radiation transmitter unit to emit THz radiation passing though the membrane (being in the optical path of the THZ radiation).

Data input receives a radiation signal pattern via radiation detection unit. The radiation signal pattern is the radiation that was not adsorbed by the membrane. The radiation signal pattern contains the THz signature. Processing utility may transmit data regarding the signal pattern (such as infected or healthy) via the data output utility, via a data communication (e.g. via cellular network) to a communication module of a central computer.

The processing utility may record the received data in a learning database in memory and/or may query/cross-reference the received data with data in the learning database to identify the properties and may communicate such data to a mobile device at which processing utility may signal to display a message corresponding to the data. To this end, the preselected data stored in the learning database may be used to compare the THz pattern/signature of the collected volatile compounds (organic or inorganic) and/or aerosols with the signatures of healthy or infected COVID-19 individuals stored in the learning database.

Vacuum may also be applied to ease suction of the VCs and/or aerosols (once a human exhale breath into the system, i.e., into the breathalyzer). The working range of vacuums which may be employed is about 600 mmHg for a short time period. The time range for application of these vacuums is from about one second to five seconds.

Identification of infected or healthy individual would be enabled by time period of less than 60 seconds. More specifically less than 30 seconds; even more specifically less than 20 seconds.

The membrane may be a pressure permeable membrane configured as a dense, compressed structure made of fibers (e.g. mesh) such that the pressure permeable membrane responds to the application/release of vacuum as a pressure dischargeable membrane. The pressure dischargeable membrane may be configured as a metamaterial membrane being a material deriving its properties not from the properties of the basic materials, but from its designed structure. The metamaterial membrane may comprise a plurality of layers of metamaterial encapsulated in a plastic housing, produced with an accuracy of ±10 microns.

In some embodiments, the system includes a spectroscopic assembly including a radiation transmitter unit being configured and operable to produce THz frequency radiation and a detection unit being configured and operable to detect an electromagnetic radiation emitted by the collected volatile compounds and/or aerosols. In particular, radiation transmitter unit is operable for irradiating the membrane with a radiation having a wavelength in the range extending from around 100 GHz to 30 THz and to scan the permeable membrane holding the collected volatile compounds and/or aerosols within a scanning window of about 100 GHz.

Although, for the sake of clarification, the radiation transmitter unit and the detection unit are represented as two separate physical elements, they can be integrated in the same physical element or in the same housing. In a specific and non-limiting example, radiation transmitter unit is configured and operable for generating inspecting and reference electro-magnetic radiation components of substantially the same frequency contents, and for sweeping/scanning the frequency. Detection unit may be located in a first path of the inspecting radiation components after passing through the membrane and in a second path of the reference radiation component directly propagating from the transmitter unit.

The spectroscopic assembly may be configured to induce a predetermined frequency difference between a frequency of the inspecting radiation component and the reference radiation component interacting at the detection unit such that a signal resulting from the interaction between the inspecting and reference components is indicative of one or more properties of the VCs and/or aerosols indicative of COVID-19 infected individuals at a location where the inspecting radiation interacts with the membrane (capturing the VCs and/or aerosols).

The system (breathalyzer) of the present invention may comprise the spectroscopy assembly as described above or may directly receive data emitted by the collected volatile compounds and/or aerosols obtained by an external spectroscopy assembly as described above or as conventionally used in the field. For example, one spectroscopy method is to radiate THz waves directly on the membrane itself and acquire their spectral information, such as the fingerprint feature or decay signals of a pulse as response signals. The spectroscopy systems include photo-mixing, heterodyne detection, and chirped-pulse THz spectroscopy. Another spectroscopy method is to use the THz resonance field in a photonic crystal, a waveguide device or frequency multiplier.

The membrane is located at the propagation path of the volatile compounds and/or aerosols. The membrane is also positioned within the optical path of the electromagnetic radiation emitted by the transmitter unit.

For example, the membrane may be spaced-apart from spectroscopic assembly. The membrane is interrogated by the spectroscopic assembly. Alternatively, the membrane may be a part of the spectroscopic assembly.

In some embodiments, the system is connectable to a communication network with a host computer, which is external to the control unit. Alternatively, the spectroscopic assembly can be also attached to the control unit by using a coupling member of any type. The control unit is configured and operable to control the operation of the spectroscopic assembly. The control unit may be integrated within the spectroscopic assembly or may be a separate element communicating with the spectroscopic assembly via wired or wireless communication.

If the control unit is integrated within the spectroscopic assembly, THz signature identification does not require or employ any type of electronic components, circuitry or antenna. It is not shown in detail, but should be appreciated, that signal exchange and communication is enabled between the modules of the system by virtue of appropriate wiring, or wirelessly. For example, the spectroscopic assembly and the control unit can be connected by IR (Infra-Red), RF (radio frequency including Bluetooth) or cable control. If the spectroscopic assembly and the control unit are integrated in the same physical housing, the THz signature is stored in the control unit. The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections, and vice versa. Also, a plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

The transmitter unit is placed at a certain distance from the membrane. The distance between the transmitter unit and the membrane may be selected to be at a close proximity being less than the wavelength of the electromagnetic radiation. For example, this distance may be selected to be below 1 mm for a radiation in the range of about 200 GHz to 1200 GHz. In a specific and non-limiting example, the distance between the transmitter unit and the membrane is selected to be in the range of about 0.599-0.749 mm. In this connection, it should be understood that, due to the propagation path in the THz range, if the distance between the transmitter unit and the membrane is selected to be less than the wavelength of the electromagnetic radiation, the result signal(s) will be screened from the environment (i.e. not affected by surrounding changes such as changes in humidity, temperature . . . ), eliminating the need to perform the acquisition of the response signal(s) in a controlled environment (e.g. a clean room such as a hood, or under inert conditions including cleaning with nitrogen or helium gas). Moreover, the short distance between the transmitter unit and membrane eliminates the absorbance of the THz signal by the environment.

Moreover, in some embodiments, the thickness of the membrane may be selected to be at least several times (e.g. at least four times) the wavelength of the electromagnetic radiation. The thickness should be selected to be sufficiently wide to enable to capture a sufficient amount of volatile compounds and/or aerosols allowing to perform an analysis providing an identifiable THz signature.

In some embodiments, the membrane is configured and operable for trapping the collected volatile compounds and/or aerosols within a period of time being less than 60 sec. more preferable, less than 30 sec.

In this connection, it should be noted that the capability of the system to identify a THz signature, provides a fast inspection rate, being a significant parameter for quickly identifying COVID-19 infected or free (healthy) individuals. It should be understood that, as described above, the THz radiation is capable of providing an identifiable signature even when the collected volatile compounds and/or aerosols are present in the vapor collection in a very-low concentration below PPB. In other words, the THz signature is sensitive to low changes in the vapor composition and provides a detection with high resolution. The high resolution of the THz signature enables to differentiate between signatures of different viruses or from a healthy individual to a COVID-19 infected individual. If the resolution of the signature is not good enough, the THz signatures would overlap and a differentiation between them is then impossible. By contrast, the use of infrared radiation does not provide an identifiable signal. A spectroscopic analysis using an infrared radiation including the collection of the gas and the separation of the different chemical components, yields poor results. Moreover, the high rate of gas delivery required by the infrared spectroscopy does not permit collection of the carrier and separated components in a small area. Furthermore, the period of time for collecting a certain amount of volatile compounds and/or aerosols which can be spectroscopically analyzed by using infrared radiation, is much higher. For example, the time consumed to be able to obtain an identifiable infrared spectral data is about half an hour. In addition, the concentration of the volatile compounds and/or aerosols in the aforementioned approach is too low to yield adequate infrared absorption. In other words, much higher concentrations are needed to provide an identifiable signal. The use of Raman techniques can provide an identifiable signal even with low concentrations of the volatile compounds and/or aerosols, however, the data collection time is much longer than with the technique of the present invention and is therefore not suitable for commercial use. Moreover, it should be noted that techniques known in the art using THz spectroscopy provide a spectral analysis of each chemical component of the collected volatile compounds and/or aerosols, separately indicating the presence of concentration of each collected volatile compound, which is highly time consuming. Since the period of time spent for trapping a minimal quantity of collected volatile compounds and/or aerosols being in a sufficient concentration for providing an identifiable signature is less than 20 sec.

The following description provides a flow chart exemplifies the system operation for identifying COVID-19 infected or COVID-19 free (healthy) individuals. The method comprises the steps of receiving data indicative of collected volatile compounds and/or aerosols being scanned with electromagnetic radiation in the THz range in step and processing the data for identifying a signature being indicative infected individuals/healthy individuals. The step of processing may comprise step of performing a pattern recognition of the signature.

In some embodiments, prior to receiving data indicative of collected volatile compounds and/or aerosols, the method further comprises performing a THz spectroscopy of the membrane. This may be implemented by scanning the collected volatile compounds and/or aerosols captured in the membrane with an electromagnetic radiation in the THz range within a scanning window of about 100 GHz (e.g. by collecting 500 measurements). This narrow scanning window enables to perform a fast scanning of the membrane and to reduce the period of time required for performing the inspection process. Moreover, this narrow scanning window also enables fast noise cancellation and an increase in accuracy of the measurements.

In some embodiments, prior to performing a THz spectroscopy of the membrane, the method may comprise the step of trapping collected volatile and/or aerosols compounds by suction, wherein the trapping is performed within a period of time being less than 30 sec.

In some embodiments, prior to step of trapping the collected volatile compounds and/or aerosols by suction, the method may comprise the step of obtaining a reference spectrum by performing a THz spectroscopy on a reference clean membrane being the same membrane used in the above. In some embodiments, the method may comprise the step of cleaning a membrane having trapped volatile compounds and/or aerosols for a further use by applying a positive/negative pressure.

In a specific and non-limiting example, performing a THz spectroscopy is implemented by scanning the membrane and collecting 500 measurements. The spectral data is processed, the spectrum of the membrane obtained filled with VCs and/or aerosols (from exhaled breath) is compared to the reference spectral data.

In some embodiments, method may further comprise the step of recording a THz signature in the learning database. The learning database may be configured to provide a THz fingerprint/signature associated with the one or more VC found in exhaled breath in COVID-19 free (healthy) individuals.

In some embodiments, method may further comprise the step of recording a THz signature in the learning database. The learning database may be configured to provide a THz fingerprint/signature associated with the one or more VC and/or aerosols found in exhaled breath in COVID-19 infected individuals.

The step of processing the data may further include comparing the received THz data to data in the learning database. Received THz data may be logged in a learning database. Logged received THz data may be used for future analyses.

Optionally, the step of processing the data may further include assessing one or more properties of an VCs and/or aerosols captured in the membrane based on the learning database data. Assessing one or more properties may be performed using a statistical analysis in which received THz data is compared to learning database THz data and a statistical comparison is performed. If a predetermined level of similarity is shown, the THz data is considered to have a certain property. After the step of performing THz spectroscopy, the membrane may be discharged of VCs and/or aerosols content via various methods which include desorption of VCs and/or aerosols and discharge with vacuum or high pressure flow.

According to another embodiment, the processing of the control unit comprises the step of providing a mathematical interpretation of pattern recognition based on a learning algorithm such as a Neural Network Acceleration algorithm (NNA). The interpretation of the pattern recognition is based on identification of special features of the pattern such as the identification of main and side peaks, the number of main and side peaks, the width of the peaks and the distance between them.

In some embodiments, the processing step of the method, may comprise the following steps: an optional preprocessing step being configured to remove irrelevant spectral trends present in the measurements, and to filter out random measurement noise; a feature extraction step being configured to estimate the most relevant vectors defining the data using a principal component analysis; and a pattern classification step using a combined linear and nonlinear pattern recognition approach.

In a specific and non-limiting example, the optional preprocessing step may include the step of establishing the learning database. The step of establishing the learning database may comprise the steps of collecting the scans, preprocessing the scans as described above, and performing a Fourier Transformation on the results.

A feature extraction step may include the step of subtracting a reference processed data from the sample processed data. The resulting data belongs to or represents only membraned with VCs and/or aerosols captured therewithin related information (without data relating to the membrane). The step of subtracting the reference processed data (e.g. membrane results) from the sample processed data (e.g. membraned with VCs and/or aerosols captured therewithin) may be followed by a step of performing a second Fourier transformation on the membrane related information to provide the specific VCs and/or aerosols related signals, among them the infected/healthy partitioning signals.

The pattern classification step may include the steps comparing all the obtained results to the learning database. When the learning database is established, the same tested individuals are tested biologically by Polymerase Chain Reaction (PCR) method for determination if they are healthy or infected. Then all the vectors obtained by the mathematical process and the variations (i.e. the mathematically calculated differences) between the samples are "translated" to infected determination and differentiation into two groups (infected and healthy samples).

As described above, the system distinguishes between COVID-19 infected and healthy individuals by measuring volatile compounds (VCs, organic or inorganic) and/or aerosols in the exhaled breath of said individuals, enabling non-invasive detection of infected or healthy individuals.

Thus, VCs and/or aerosols (from exhaled breath of humans) are adsorbed onto the membranes. The "loaded" membranes are then analyzed by applying electromagnetic radiation (e.g., between 600-750µm in the case of the terahertz part of the spectrum, though other bands of the electromagnetic spectrum may be used) to the membrane and observing the change in the electromagnetic radiation. Analysis of the membrane may be accomplished using an electromagnetic radiation transmitter and an electromagnetic radiation detector typical of a spectrometer operating at terahertz wavelengths. During analysis the membrane is positioned within the beam of electromagnetic radiation emitted by the transmitter. The electromagnetic radiation passes into the membrane and the interaction of the VCs and/or aerosols trapped in the membrane alter the electromagnetic radiation. After contacting the membrane, the altered electromagnetic radiation is captured by the electromagnetic radiation detector. The changes in the electromagnetic radiation can be used to determine what VCs and/or aerosols are being released in the breath of the tested individuals. By analyzing the type and amount of VCs and/or aerosols, either infected or healthy tested individuals can be determined.

Electromagnetic radiation in the terahertz range may be used to analyze VCs and/or aerosols. The analysis spectra may be generated using absorbance, transmittance, reflectance, or Raman spectroscopy.

In a preferred embodiment, terahertz electromagnetic radiation is used for the detection of VCs and/or aerosols captured in a membrane. As used herein terahertz electromagnetic radiation refers to radiation having a wavelength of between 1 mm to 0.01 mm. In a particular embodiment, terahertz radiation within the 600-750μη range is used to determine the VC content in a PET or open-cell foam-based melamine membrane. The electromagnetic radiation detector generates an absorption spectrum. Absorption spectra can be obtained in the frequency domain, or in the time domain and translated to frequency via Fourier transform, depending on the spectroscopic method used.

The absorption spectra is read and compared to a database via software matching algorithms. The database contains spectral fingerprints of a healthy individual and an infected one. The software matching algorithm compares the collected spectrum to the catalogued fingerprint within predetermined confidence bounds, and identifies an COVID-19 infected or free (healthy) individual by determining whether or not the read spectrum falls within the error bounds of the fingerprint. In an embodiment, membranes may be recycled via application of electricity to release the VCs and/or aerosols from the membrane. The "cleaned" membrane is cycled back into place on the sampling apparatus. In other embodiments, the membrane can be cleaned by reversing the flow of the vacuum motor, which causes air to pass through the membrane and push the absorbed molecules from the membrane. In certain embodiments, each membrane may be used only once and then replaced by a new membrane.

According to at least one embodiment, the membranes are single used; alternatively, the membrane are cleaned and reused.

In an embodiment, the device includes a gas collection device which is placed proximate to the membrane to collect the VCs and/or aerosols exhaled from the breath of the tested individuals.

According to at least one embodiment, the system will inform the user, by means of optical illustration, voice or any other means, if sufficient enough of air is exhaled and analysis can begin. For example, the system can have a red light if there is not enough of VCs and/or aerosols (from the exhaled air) and a green light is the is.

Once a sufficient amount of gas is collected, the membrane can be analyzed using techniques set forth herein to determine the VC content of the gas (by means of analyzing the spectrum, as described above). The inventors of the present invention found that each mix or blend of VCs and/or aerosols has a separate THz signature which can be translated by using the teachings of the present invention to distinct peaks of the Fourier transformation. Therefore, the identification of the special features of the pattern such as the number of peaks, the distance between the main peaks, the identification of main and side peaks, the width of the peaks enables to define and identify a healthy individual from an infected one. In other words, the inventors have found that obtaining a ratio between the THz signatures of different individuals being tested properties enables identification of these properties, and that the specific identification of each VC component as well as each concentration is not necessary to identify a healthy or a COVID-19 infected individual.

It could be that the volatiles will be not only Ketones but a mixture of Ketones and/or, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, $NO_2$ and any combination thereof.

Thus, by utilizing a Neural Network Analysis (NNA) system which is based on machine-learning ability, the system will continuously improve with each additional performance as database (DB) grows. The learning process is essential to "educate" the system to include more spectral variations within its solution space. In order to improve the predication, the sampling size has to be increased so the statistics will be able to validate for the model.

According to at least one embodiment, Leave One Out (LOO) algorithm is the one of the methods that could be used for the analysis of the Terahertz spectra detection, in order to provide accurate detection of a COVID-19 infected individual or a healthy individual.

It is acknowledged that LOO is a statistical method used to evaluate the efficacy of any classification procedure, with a relatively low number of samples, in order to teach and train spectroscopy systems to analyze spectral vectors. According to this machine learning method, the training is performed repeatedly, each time after excluding one training sample from the training data of the group, and then testing on those individual vectors that were excluded from training. Based on that specific learning process of LOO, a prediction is made for the left-out spectra and compared to the actual PCR results.

The actual classification of each spectral vector is made by either using a linear classification method (see Fisher R. A. The Use of Multiple Measurements in Taxonomic Problems. Annals of Eugenics, 7 Part II:179-188, 1936) or using the Mahalanobis distance classifier (see Mahalanobis, P.C. On the generalized distance in statistics. Proceeding of the National Institute of Sciences of India. 2(1):49:55). Both methods use the classes' means and covariances to assign each input vector to its own class based on its multi-dimensional distances from each class. Therefore, the results obtained clearly indicate that this procedure is adequate for classifying unseen spectra into their associated classes, with a high probability of detection and low "false-alarm" rates.

According to another embodiment, the method is based on a "Principal Component Analysis" (see Konstantinos, I.D. and Sun-Yuang, K. Principal Component Neural Networks: Theory and Applications. Wiley-Inter-science, New York, 1996). According to this mathematical technique, the mean (symbol below as "m") is subtracted from each spectrum (after being normalized by its associated reference) and the covariance (symbol below as small sigma as standard deviation) matrix of the combined spectra is computed. The eigen-values of this matrix are found, and the largest values are used to compute their respective eigen-vectors. This procedure is essentially a linear transformation of the normalized spectra into a set of vectors that best represent the training samples and are less prone to noise.

These eigen-vectors (also called feature vectors) are then used to obtain a set of co-efficient vectors, one for each input spectrum, whose length equals the number of the feature vectors selected.

The Principal Component Analysis is represented by the following formula:

$$J = \frac{(m_1 - m_2)^2}{(\sigma_1^2 + \sigma_2^2)}$$

where J is the power of separation between two groups, m1 and m2 are the means of each group, σ1 and σ2 are the standard deviations of each group, and the two groups are on a continuous measurement where m2=the value of m1 at one standard deviation. The purpose of the spectral classification stage is to train the algorithm, by using a known set of spectra and then to classify previously unseen spectra into their respective classes, with a minimal number of errors. The target for 100% separation is J>19 (as shown in the equation above).

According to at least one embodiment, the membrane is made of hardened extruded plastic, containing pores of two specific sizes, and acting as Ketones trap. It should be noted that the compound could also be, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane (CH4), Carbon dioxide (CO2), Nitrous oxide (N2O), Ozone (O3), Chlorofluorocarbons (CFCs), Hydrofluorocarbons (includes HCFCs and HFCs), NO, NO2, aromatic alcohols, aldehydes and any combination thereof and not just Ketones.

According to another embodiment of the present invention is to provide a single-use, disposable membranes. According to another embodiment the membrane is reusable.

Reference is now made to FIGS. 1a-g 1 illustrating an embodiment of the sampler of the present invention. According to this embodiment, the sampler (which will be integrated into a system for label-free, noncontact, noninvasive, and nondestructive detection of at least one virus infected or free (healthy) individuals from at least one tested individual), comprising a proximal end and a distal end interconnected by a main longitudinal axis, along which at least one metamaterial membrane absorber (34, see FIG. 2) is positioned; and into which said tested individual exhale breath, such that the propagation path of said exhaled breath and volatile compounds, VCs, and/or aerosols therewithin intersect said at least one metamaterial membrane and absorbed therewithin. The exhaled air enters the sampler at 20 and exits at 21.

In FIG. 1a, the membrane 34 is enclosed in a membrane housing (also refers to as a membrane holder) 33.

Figure 1B:
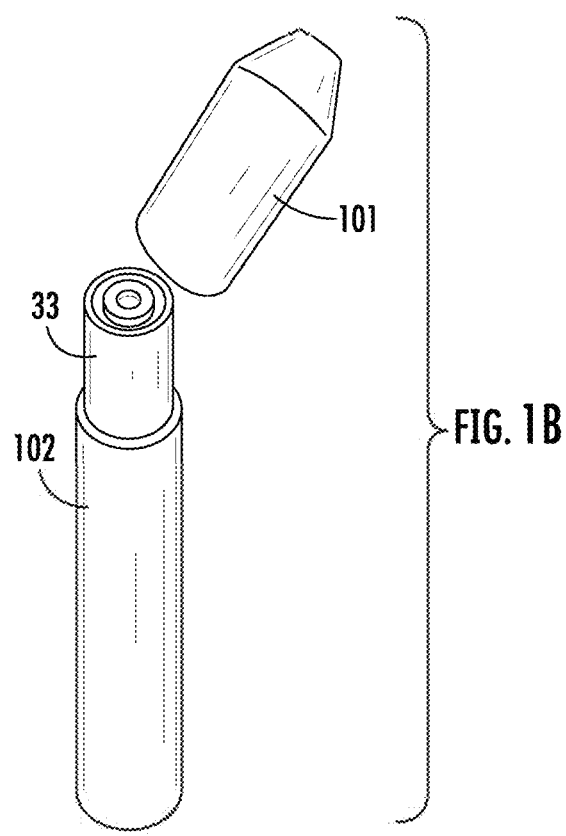

Reference is now made to FIGS. 1b-1c illustrating the sampler.

According to at least one embodiment of the present invention, the sampler comprises 2 parts, a proximal part 102 and a distal part 101 interconnected by a main longitudinal axis. Said distal part is adapted to be placed in proximity to the testes subject mouth (for receiving the exhaled breath).

Said sampler is characterized by 2 configurations, an open configuration (shown in FIG. 1b) in which the distal and proximal part are disconnected and the membrane (along with the membrane housing can be inserted or extracted from the sampler; and a closed configuration (shown in FIG. 1c) in which the distal and proximal part are connected and the sampler can be used.

Reference is now made to FIGS. 1d-1g illustrating the membrane 34 (see FIG. 1d), the membrane housing 33 (see FIG. 1e), the membrane 34 alongside the membrane housing 33 (see FIG. 1f) and the membrane 34 integrated within the membrane housing 33 (see FIG. 1g).

It is noted that the metamaterial membrane absorber 30 being configured and operable for trapping the collected volatile compounds and/or aerosols within the exhaled breath.

Figure 2A:
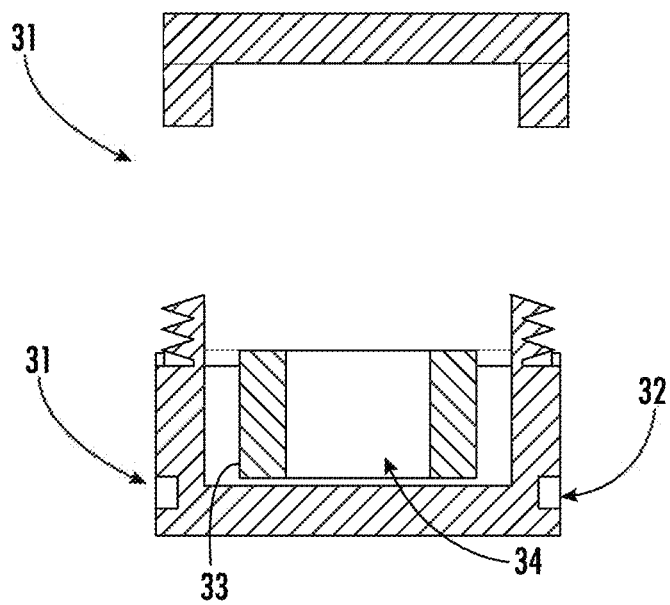
FIG. 2a schematically illustrates an exemplary membrane according to an embodiment.
Figure 2B:
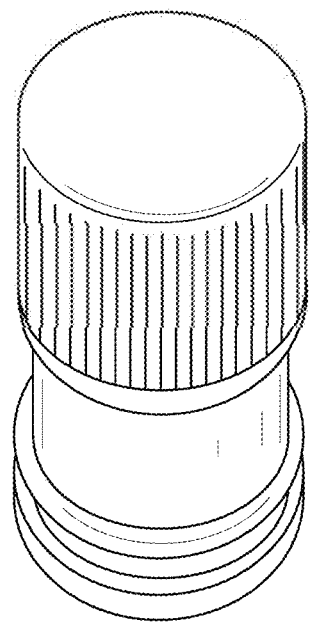
FIG. 2b schematically illustrates a membrane according to an exemplary embodiment.

According to at least one embodiment of the present invention, the metamaterial membrane absorber 30 is enclosed within a membrane housing 33 (see FIGS. 2a-b).

According to another embodiment of the present invention, the sampler is polyoxymethylene-based (aka Delrin™)

According to another embodiment of the present invention the metamaterial membrane 34 is made of open-cell foam-based melamine.

According to another embodiment of the present invention the membrane housing 33 is made of PTFE (Polytetrafluoroethylene, aka Teflon).

Reference is now made to FIGS. 2a-2b providing a closer view of the membrane 34 and the membrane housing 30.

The membrane housing comprising a body 33 made of PTEE.

After the tested subject exhale breath into the sampler, the membrane 34 (enclosed within the membrane housing 33) is extracted from the sampler and place in a dedicated capsule 31. The dedicated capsule 31 (shown in FIG. 2) comprises a scanner holder alignment slot 32 (that ensures the correct alignment of the capsule 31 in the scanning system).

According to another embodiment of the present invention the capsule 31 is made of PTFE (Polytetrafluoroethylene, aka Teflon).

According to another embodiment, the capsule has sealing means to seal the capsule once the membrane (and the membrane housing) is inserted therein.

According to at least one embodiment, the sealing member is an o-ring.

Figure 3A:
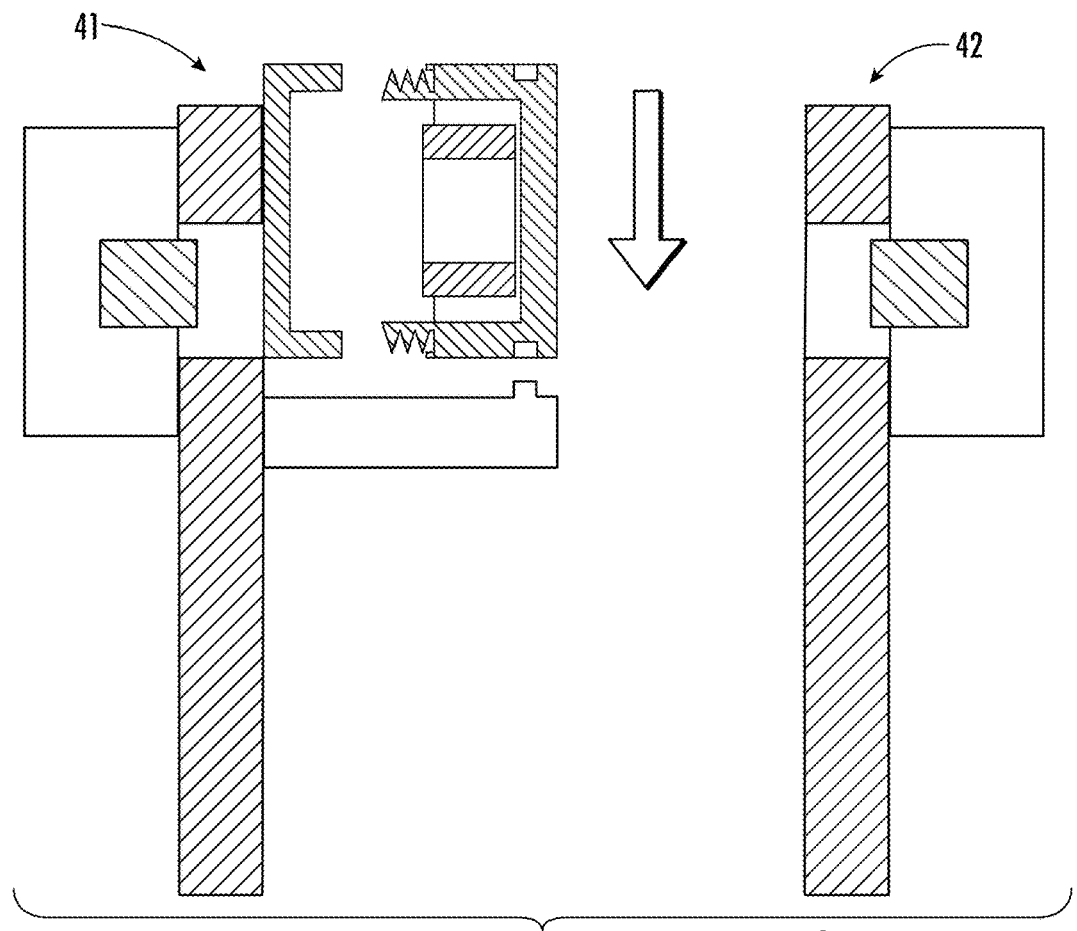
FIG. 3a schematically illustrates an electromagnetic testing unit (tester) according to an exemplary embodiment.
Figures 3B, 3C, 3D, 3E:
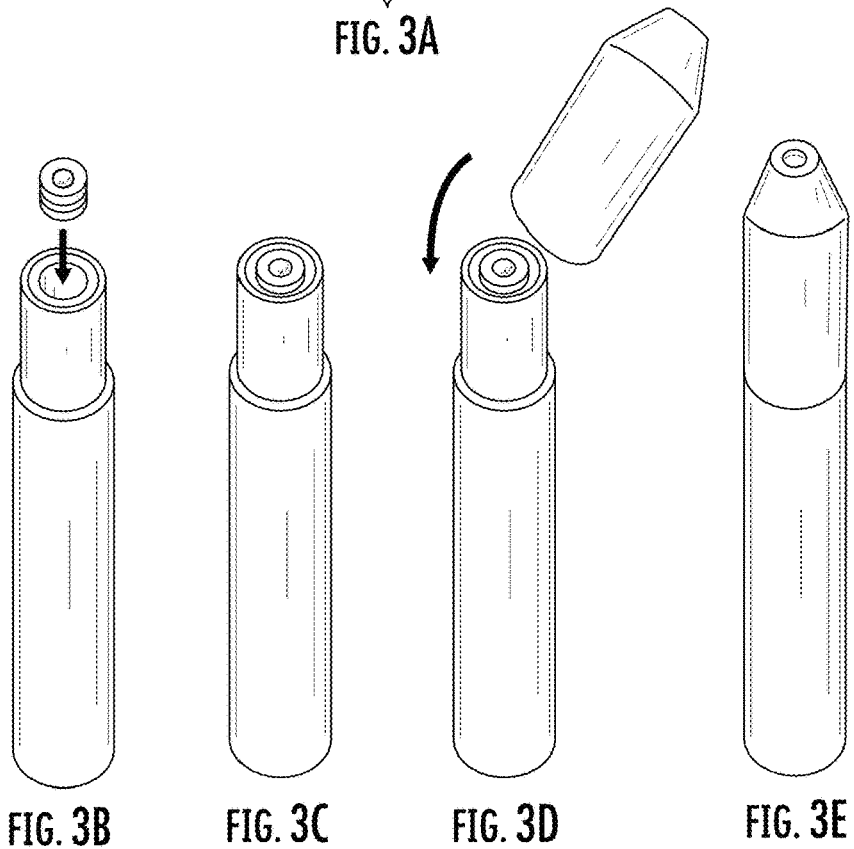
FIG. 3b depicts a process according to an exemplary embodiment.
FIG. 3c depicts a process according to an exemplary embodiment.
FIG. 3d depicts a process according to an exemplary embodiment.
FIG. 3e depicts a process according to an exemplary embodiment.
Figure 3F:
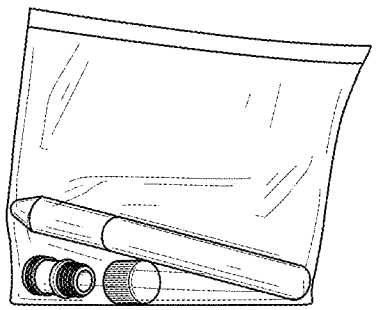
FIG. 3f depicts a process according to an exemplary embodiment.
Figure 3G:
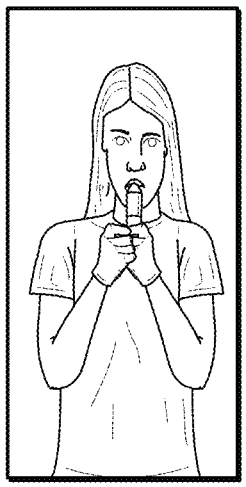
FIG. 3g depicts a process according to an exemplary embodiment.
Figure 3H:
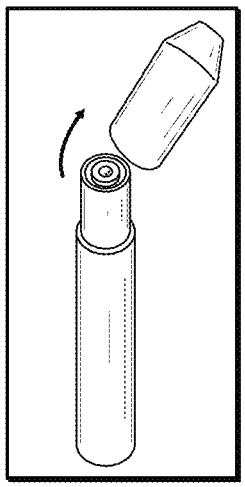
FIG. 3h depicts a process according to an exemplary embodiment.
Figure 3I:
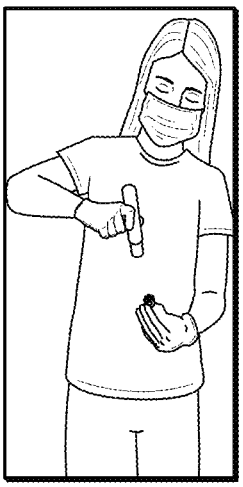
FIG. 3i depicts a process according to an exemplary embodiment.
Figure 3J:
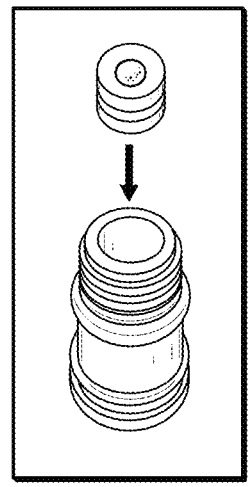
FIG. 3j depicts a process according to an exemplary embodiment.
Figure 3K:
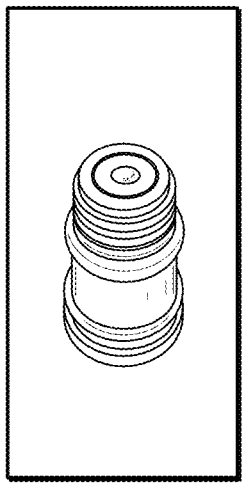
FIG. 3k depicts a process according to an exemplary embodiment.
Figure 3L:
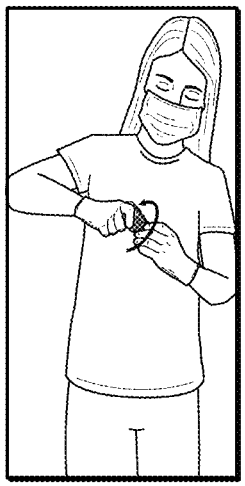
FIG. 3l depicts a process according to an exemplary embodiment.
Figure 3M:
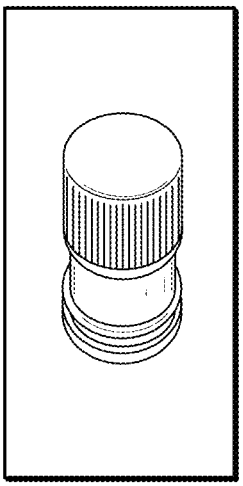
FIG. 3m depicts a process according to an exemplary embodiment.
Figure 3N:
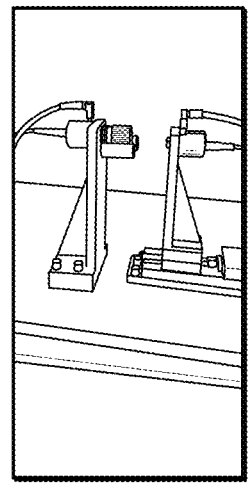
FIG. 3n depicts a process according to an exemplary embodiment.

Reference is now made to FIG. 3a, illustrating the integration of the capsule in the THz scanning system.

As described in FIG. 2, the scanner holder alignment slot 32 is aligned with a protrusion in the scanner, 43 to ensure the proper alignment.

The scanning system comprises at least one Tx (transmitter) photomixer 41 and at least one Rx (receiver) photomixer 42 to transmit and received THz signal, respectively.

Reference is now made to FIGS. 3b-3n which illustrates the method of using the sampler to test individuals for SARS-CoV-2, according to the following exemplary process.

1. The sampler is opened;
2. The membrane in inserted into the membrane holder and both are inserted into the sample (the hand-held polyoxymethylene-based tube), (see FIGS. 3b-3d);
3. The sampler is closed and ready to be used (see FIG. 3e);
4. A tested subject receives a disposable testing kit which comprises (a) a disposable, hand-held polyoxymethylene-based (aka Delrin) tube (the sampler); (b) a disposable membrane (e.g., an open-cell foam-based melamine membrane) placed in a PTFE (Polytetrafluoroethylene, aka. Teflon) disposable holder (both the membrane and the membrane holder a pre-placed in the tube); and, (c) a disposable, sterile PTFE (Polytetrafluoroethylene, aka. Teflon) capsule. The disposable testing kit is identifiable with a QR/barcode assigned to each tested subject, see FIG. 3f 5. Exclusively assigning the disposable testing kit is to said subject being tested.
6. The tested subject blows into the disposable, hand-held tube (the sampler) 3-5 prolonged breaths. See FIG. 3g;
7. The breath aerosols are absorbed onto the membrane.
8. The sampler (hand-held polyoxymethylene-based tube) is opened to enable the extraction of the membrane and its holder, see FIG. 3h;
9. The membrane (with its holder) is extracted from the sampler, see FIG. 3i;
10. The membrane (with its holder) is inserted into the capsule, see FIGS. 3j-3k. Once the membrane (and the membrane holder) is in the capsule, the capsule is closed (thus, sealed), see FIGS. 3l-3m.
11. Next, the capsule is placed inside the THz scanner and then scanned, see FIG. 3n.

Following the 20-60 second scan, results are received.

Upon completion of the sample scanning, the used capsules, containing the biologically contaminated membrane (i.e., with the tested subject's biological breath sample), will be thrown into the biological waste collection bin within the designated testing site.

According to at least one embodiment of the present invention, the THz scanner virus is a THz sensing spectrometer, in the range of 0.3 THz to 30 THz operated as a diagnostic molecular radar.

The THz scanner main parts are 2 Distributed Feedback Laser, DFB lasers, temperature electric control units, control unit, power unit and photo mixers. The laser beam is used to modulate a photocurrent at a tuned THz frequency by illuminating the TX photo mixer, the THz beam travel through the Sample Under Test (SUT) and received at the RX photo mixer.

Figure 4A:
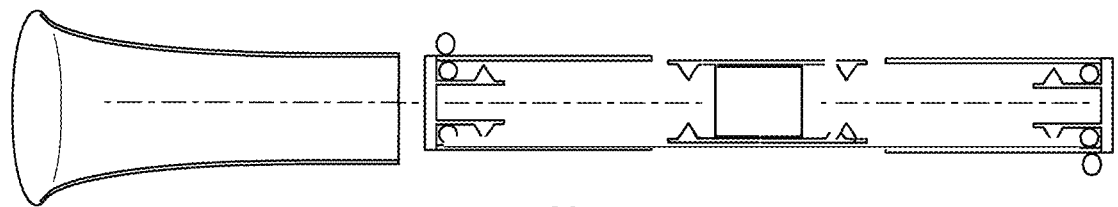
FIG. 4a schematically illustrates another exemplary embodiment of the sampler.
Figure 4B:
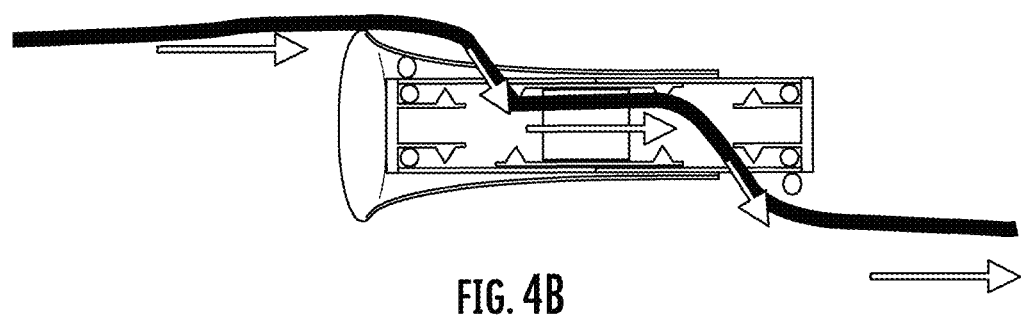
FIG. 4b schematically illustrates another exemplary embodiment of the sampler.
Figure 4C:
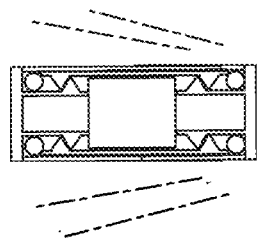
FIG. 4c schematically illustrates another exemplary embodiment of the sampler.

Reference is now made to FIGS. 4a-4d which illustrates another embodiment of the sampler. In this embodiment the sampler is composed of 2 parts as seen in FIGS. 4a-4b.

The tested individual exhales air (the arrows in FIG. 4b denotes the air movement). Thereafter, the two parts are assembled together (by approaching one to the other), see FIG. 4c and taken by a dedicated tool (illustrated in FIG. 4d) to be scanned by the THz scanner.

Reference is now made to FIGS. 5-6, illustrating alternative embodiments of the sampler device. In those embodiments, the use of a capsule is redundant.

Figure 5A:
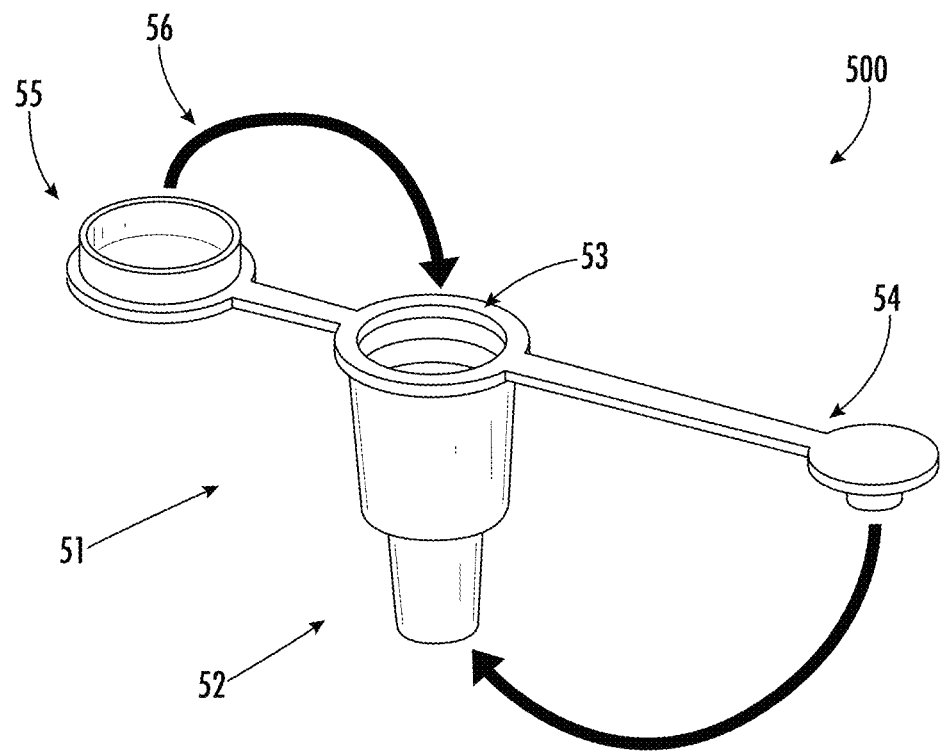
FIG. 5a schematically illustrates another exemplary embodiment of the sampler and/or method of sampling with the same.
Figure 5B:
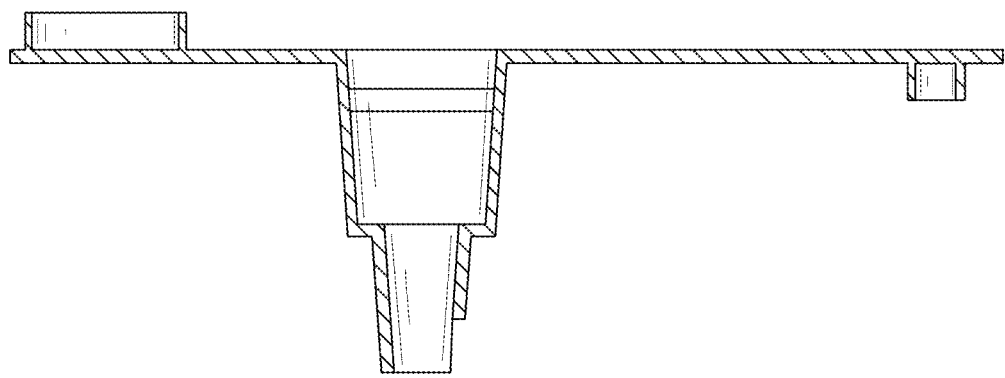
FIG. 5b schematically illustrates another exemplary embodiment of the sampler and/or method of sampling with the same.

Reference is now made to FIGS. 5a-5b, showing a sampler in which the membrane and the membrane housing are already integrated therewithin. The sampler is then closed and sealed and then scanned in the THz domain. Thus, no need for extraction of the membrane from the sampler to the capsule.

As seen in FIG. 5a, the sampler has a body 51, an upper portion 52 insertable into the tested subject's mouth (for exhale breath) and a lower portion 53. After the subject exhale breath the sampler is sealed by means of 54 and 55 closures closing the upper and lower portions (see arrows 56 and 57).

Closures 54, 55 both close the sampler and seal the same.

FIG. 5b illustrates a cross sectional view of the sampler. The membrane (and the membrane housing) are placed in location 58.

Figure 5C:
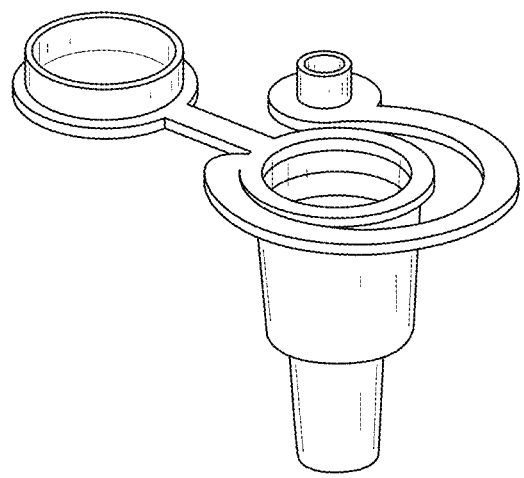
FIG. 5c schematically illustrates another exemplary embodiment of the sampler and/or method of sampling with the same.

FIG. 5c illustrates another embodiment of the sampler, in which at least one of the closures is spiral-like coupled to the body of the sampler.

Figure 5D:
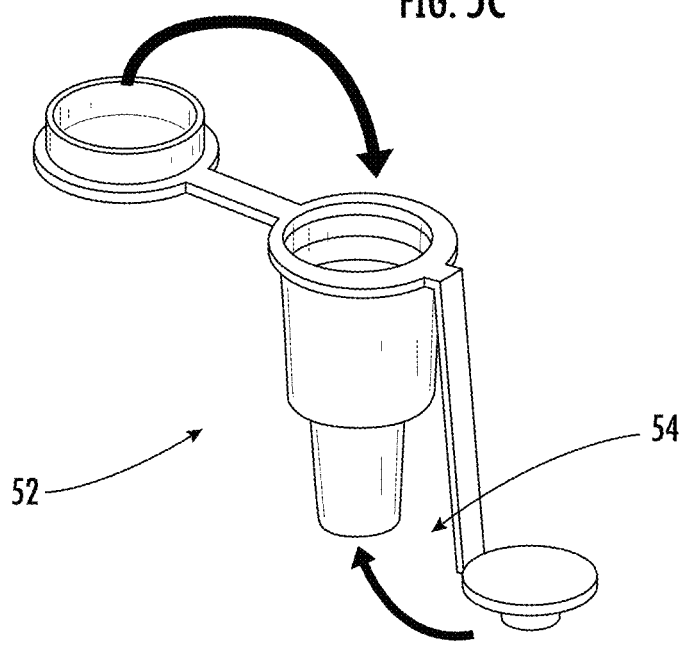
FIG. 5d schematically illustrates another exemplary embodiment of the sampler and/or method of sampling with the same.
Figure 5E:
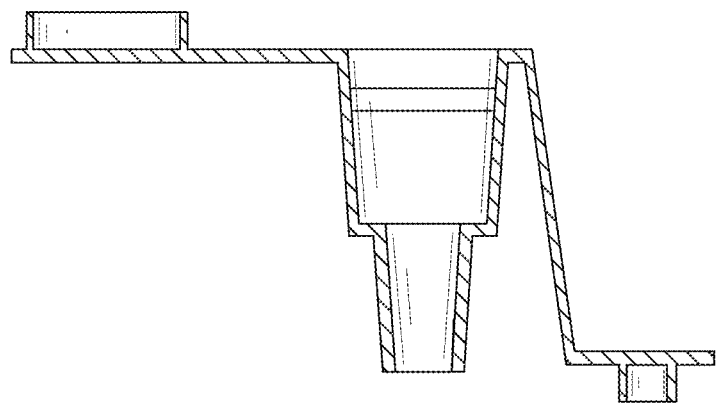
FIG. 5e schematically illustrates another exemplary embodiment of the sampler and/or method of sampling with the same.

Reference is now made to FIGS. 5d-5e, in which closure 54 faces the upper portion 52. FIG. 5e illustrates a cross sectional view of FIG. 5d.

Reference is now made to FIG. 5f, illustrating another embodiment of the sampler, in which handles 58 are provided.

Reference is now made to FIGS. 5g-5h illustrating another embodiment of the sampler. In this embodiment, the sampler is made of 2 parts 61 and 62. Each part is composed of a body and a closure 63 and 64, respectively.

Prior to coupling the two parts, the membrane 66 (or membrane housing) is placed. Once the membrane is positioned at its location (see FIG. 5h), the sampler is ready for use.

Figure 5I:
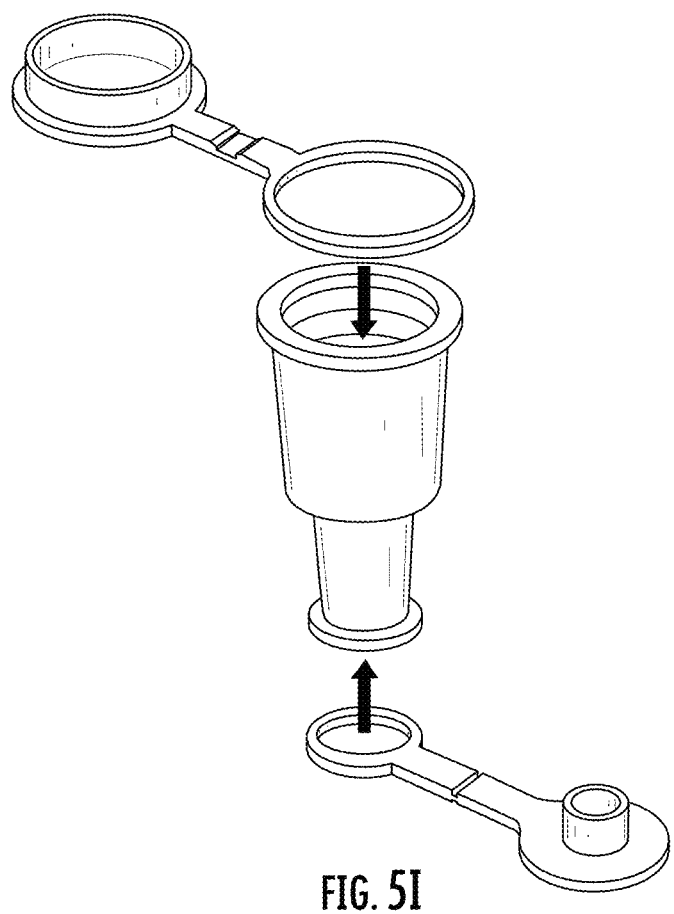
FIG. 5i schematically illustrates another exemplary embodiment of the sampler and/or method of sampling with the same.

Reference is now made to FIG. 5i illustrating another embodiment of the present invention, in which the closures 54 and 55 are provided as separate parts and not as integral part of the sampler.

Reference is now made to FIGS. 6a-6f illustrating another embodiment of the present invention, in which the sampler 500 additionally comprising Lego-like connection(s) (71 and 72) are provided so as to enable stack like connection between the sampler prior to insertion into the THz scanner (as discussed below).

According to at least one embodiment of the present invention, the THz scanner virus is a THz sensing spectrometer, in the range of 0.3 THz to 30 THz operated as a diagnostic molecular radar.

The THz scanner main parts are 2 Distributed Feedback Laser, DFB lasers, temperature electric control units (temperature controllers), a control unit (controller), power unit and photo mixers. The laser beam is used to modulate a photocurrent at a tuned THz frequency by illuminating the TX photo mixer, the THz beam travel through the Sample Under Test (SUT) and received at the RX photo mixer.

Figure 6A:
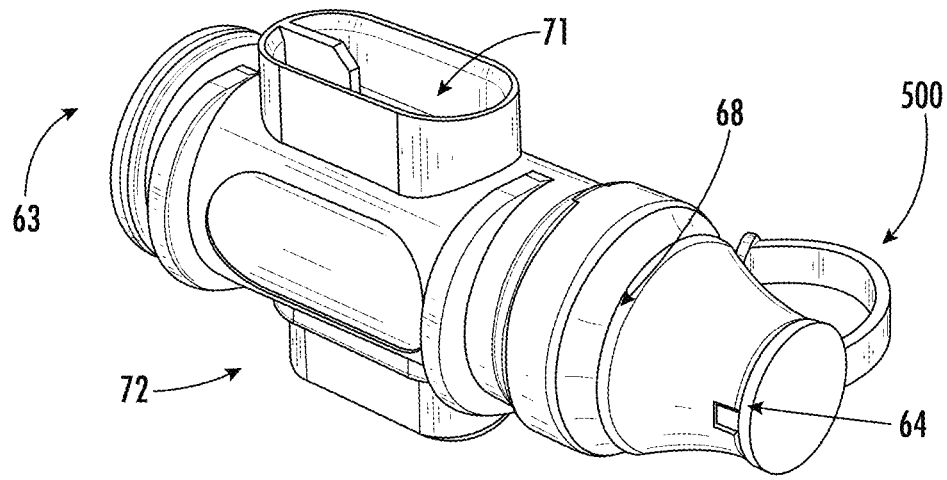
FIG. 6a schematically illustrates another exemplary embodiment of the sampler and/or method of sampling with the same.
Figure 6B:
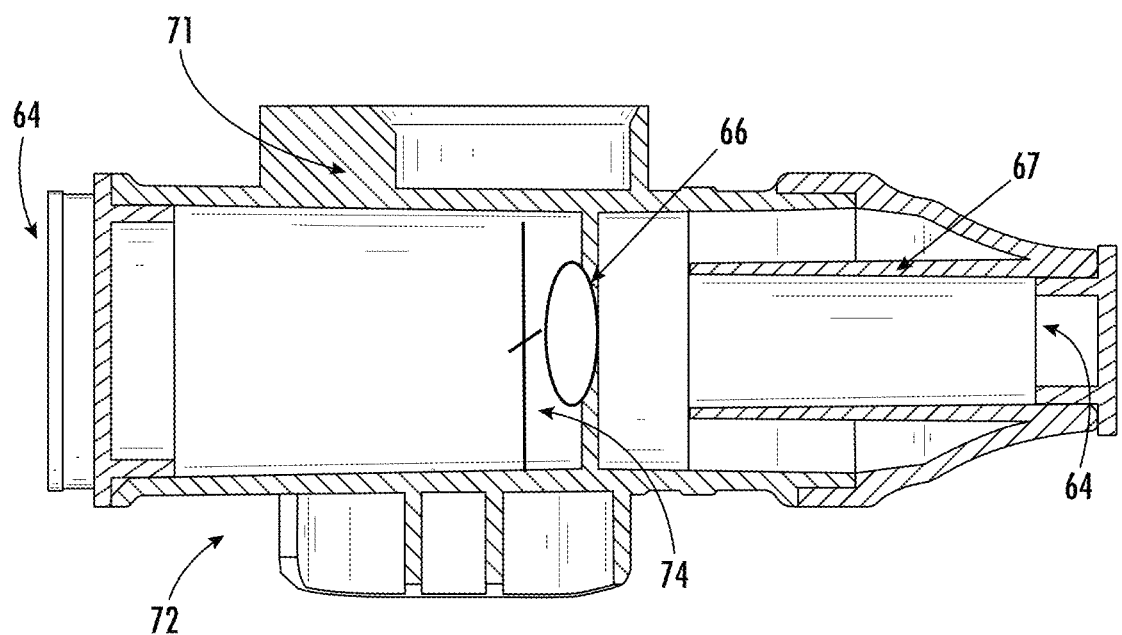
FIG. 6b schematically illustrates another exemplary embodiment of the sampler and/or method of sampling with the same.
Figure 6C:
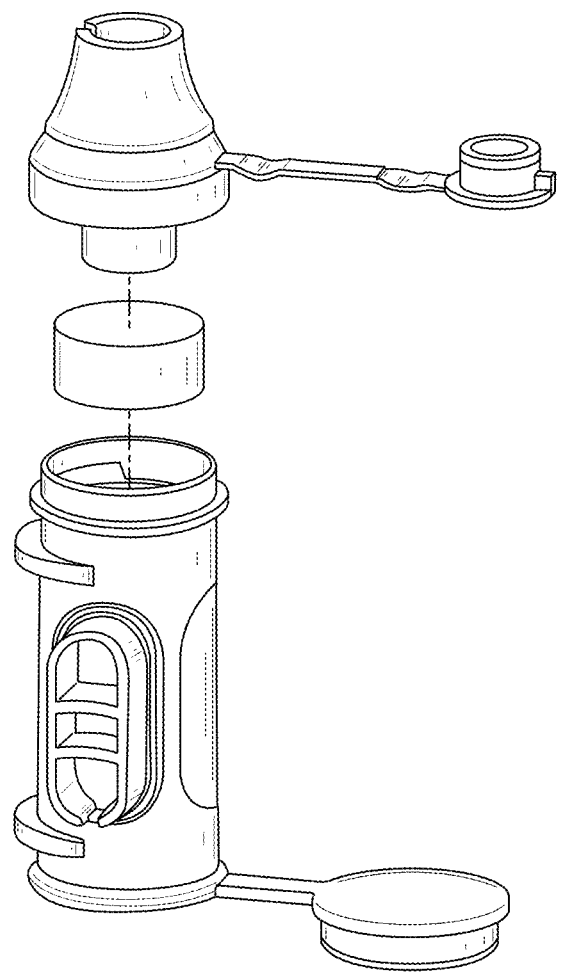
FIG. 6c schematically illustrates another exemplary embodiment of the sampler and/or method of sampling with the same.
Figure 6D:
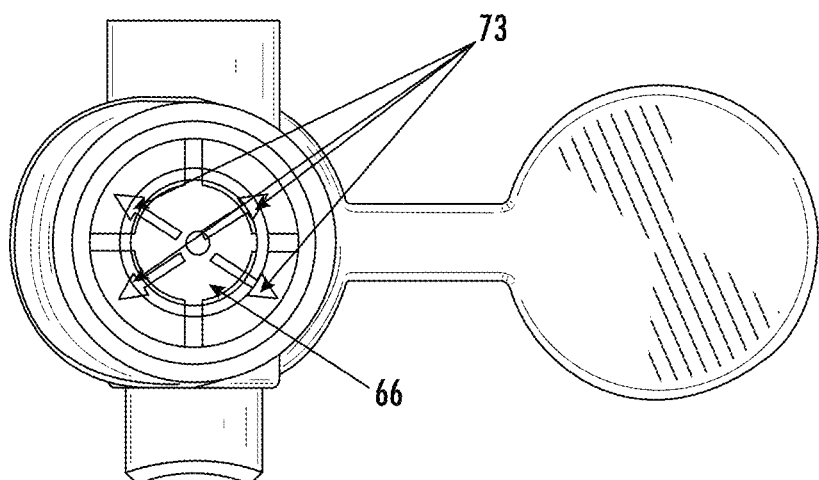
FIG. 6d schematically illustrates another exemplary embodiment of the sampler and/or method of sampling with the same.
Figure 6E:
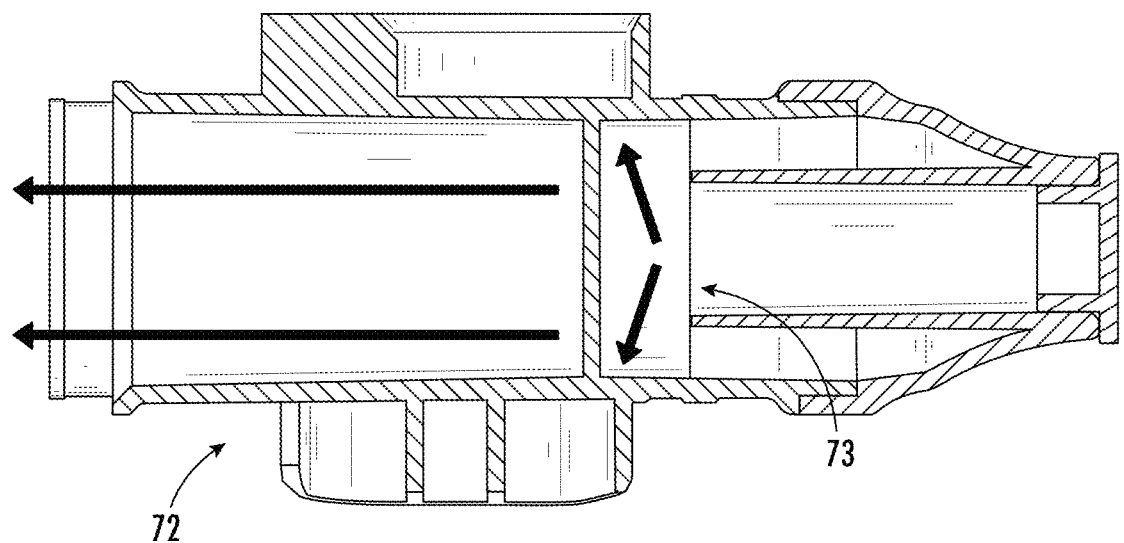
FIG. 6e schematically illustrates another exemplary embodiment of the sampler and/or method of sampling with the same.
Figure 6F:
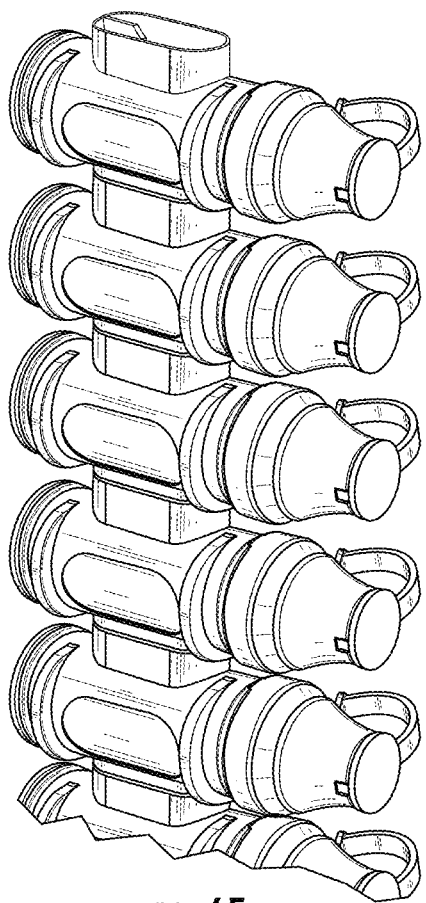
FIG. 6f schematically illustrates another exemplary embodiment of the sampler and/or method of sampling with the same.
Figure 6G:
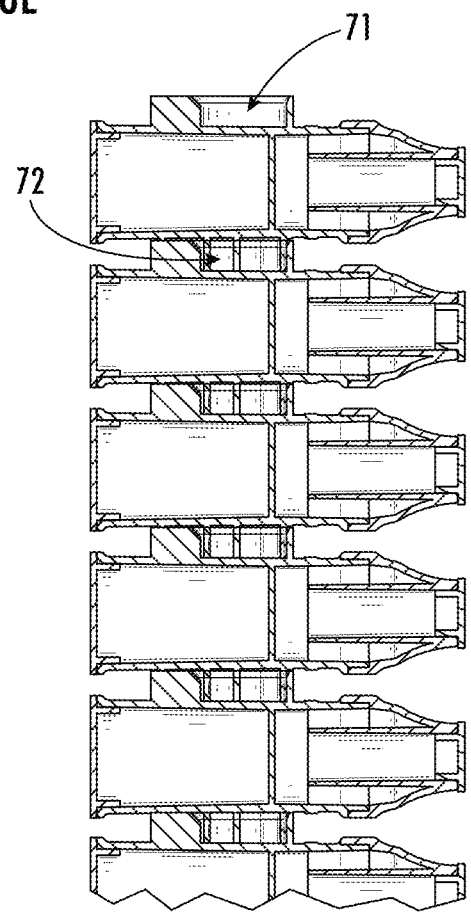
FIG. 6g schematically illustrates another exemplary embodiment of the sampler and/or method of sampling with the same.
Figure 6H:
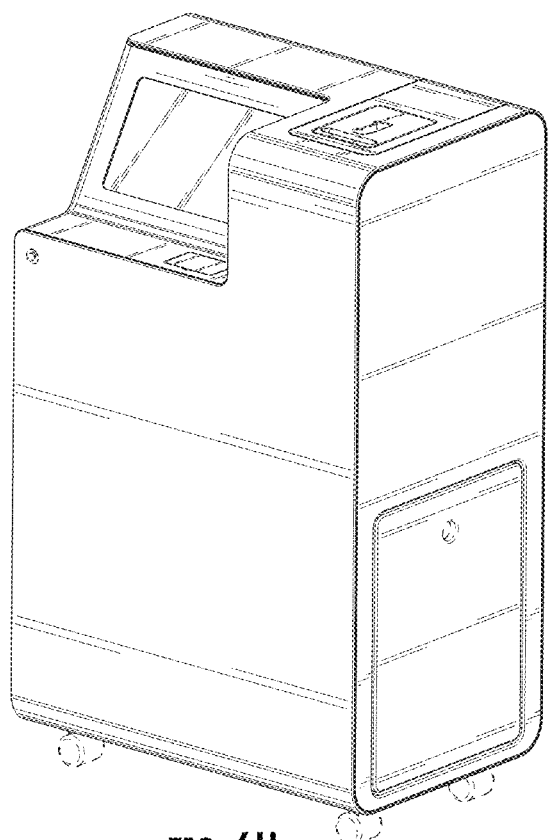
FIG. 6h schematically illustrates another exemplary embodiment of the sampler and/or method of sampling with the same.
Figure 6I:
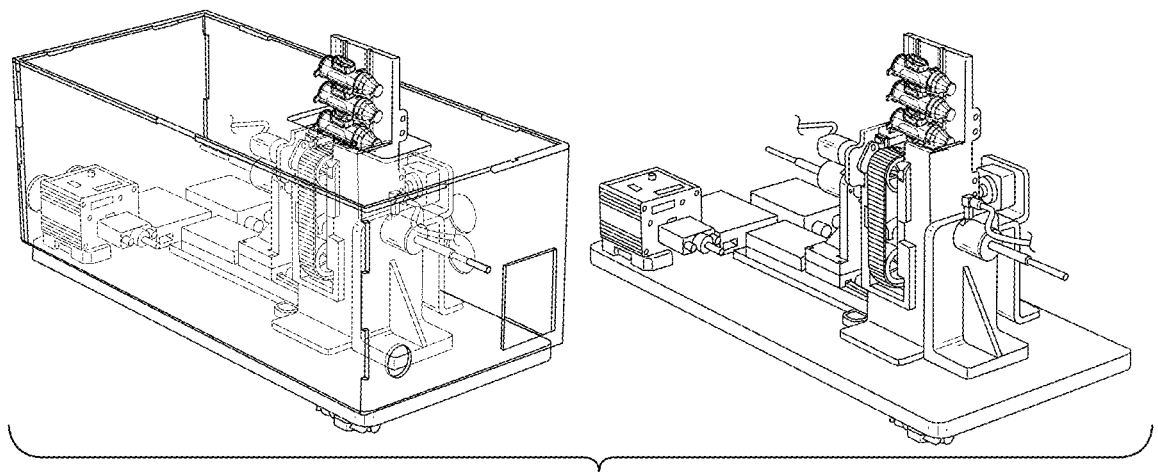
FIG. 6i schematically illustrates another exemplary embodiment of the sampler and/or method of sampling with the same.
Figure 6J:
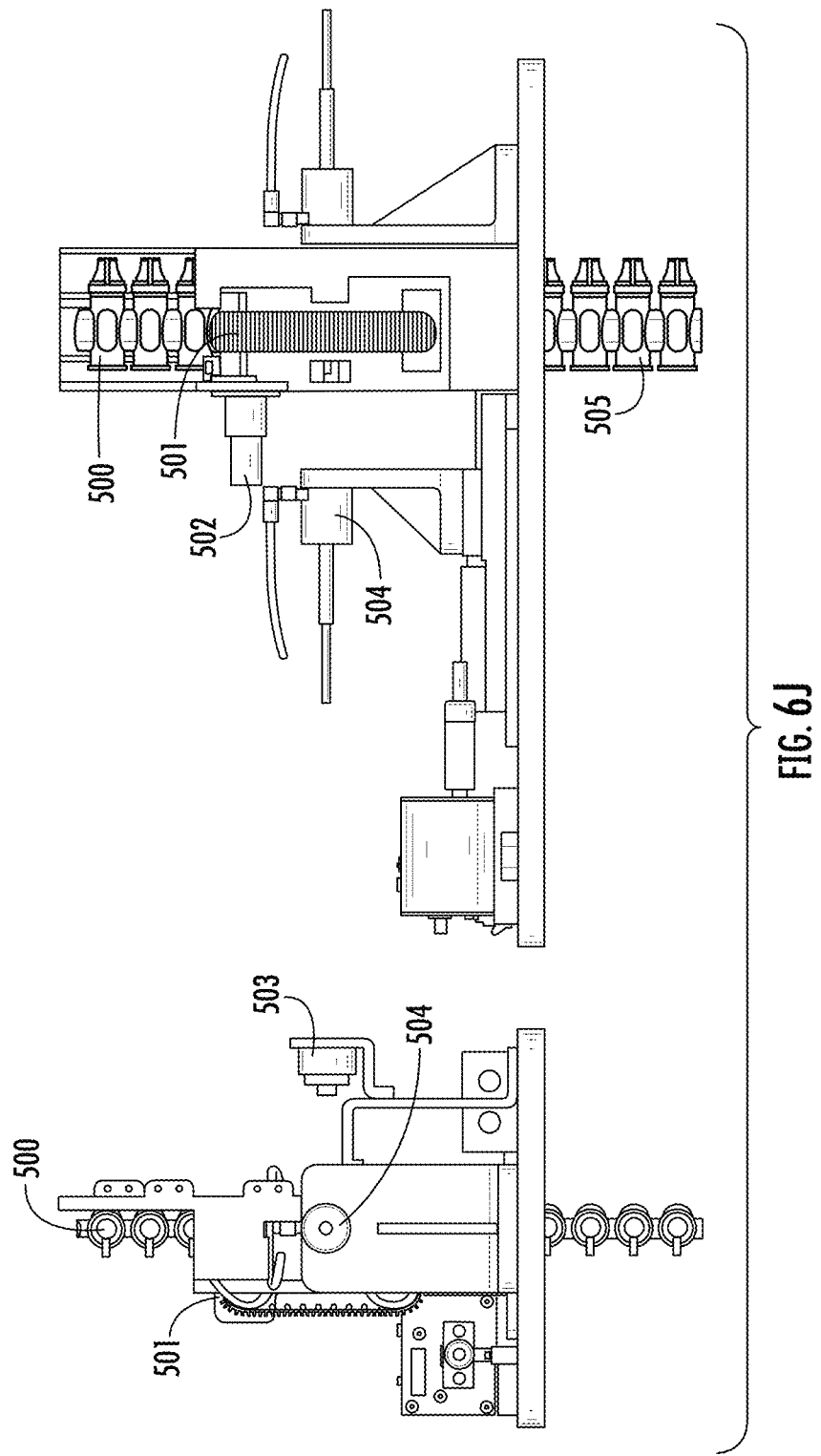
FIG. 6j schematically illustrates another exemplary embodiment of the sampler and/or method of sampling with the same.
Figure 6K:
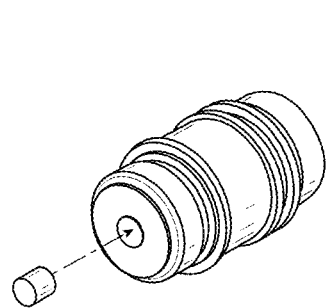
FIG. 6k schematically illustrates another exemplary embodiment of the sampler and/or method of sampling with the same.
Figure 6L:
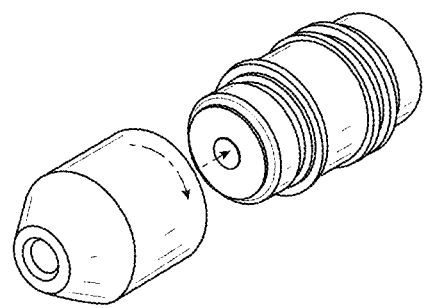
FIG. 6l schematically illustrates another exemplary embodiment of the sampler and/or method of sampling with the same.
Figure 6M:
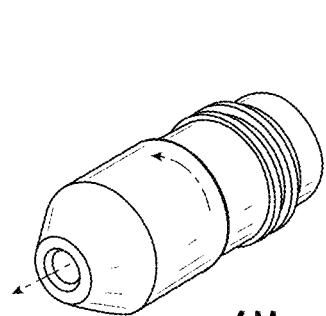
FIG. 6m schematically illustrates another exemplary embodiment of the sampler and/or method of sampling with the same.
Figure 6N:
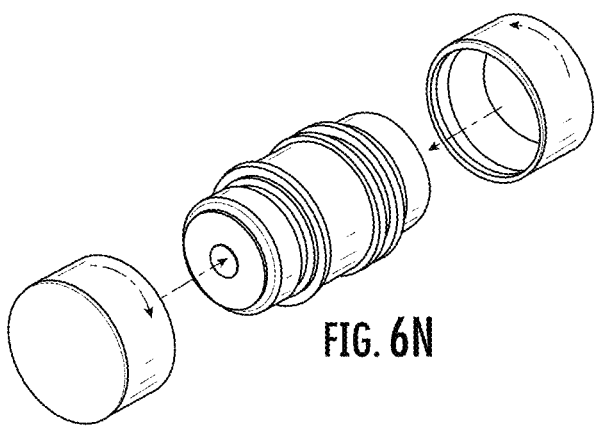
FIG. 6n schematically illustrates another exemplary embodiment of the sampler and/or method of sampling with the same.
Figure 6O:
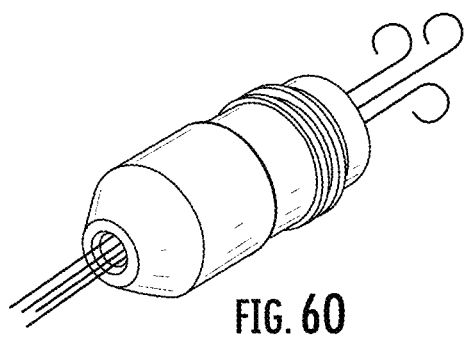
FIG. 6o schematically illustrates another exemplary embodiment of the sampler and/or method of sampling with the same.
Figure 6P:
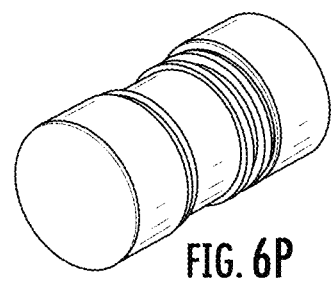
FIG. 6p schematically illustrates another exemplary embodiment of the sampler and/or method of sampling with the same.
Figure 6Q:
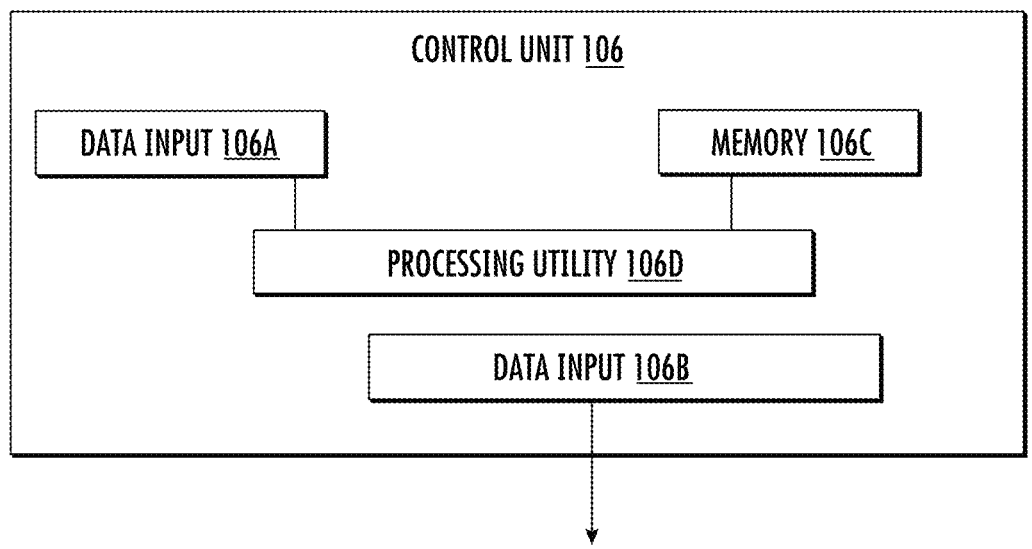
FIG. 6q depicts a representative control arrangement according to an embodiment.

As shown in FIG. 6q, a controller 106 of at least one embodiment is configured to receive and process signals from a sample and identify spectral special features indicative of the sample. For example, the THz signature may include information on the virus status of the individual. In some embodiments, the controller 106 is configured and operable for performing a pattern recognition of the THz signature. The control unit 106 is configured generally as a computing/electronic device including inter alia such utilities as data input and output utilities 106A, 106B, memory (e.g., non-volatile memory) 106C, and data processing utility (e.g. data processor) 106D. The utilities of the control unit 106 may thus be implemented by suitable circuitry and/or by software and/or hardware components including computer readable code configured for implementing the operations of methods and systems described herein.

Figure 4D:
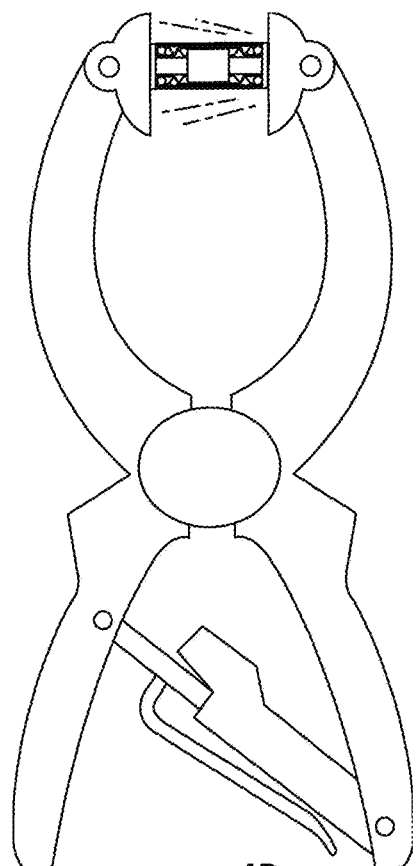
FIG. 4d schematically illustrates another exemplary embodiment of the sampler and/or method of sampling with the same.

Reference is now made to FIGS. 4-4d which illustrates another embodiment of the sampler. In this embodiment the sampler is composed of 2 parts.

The tested individual exhales air (the arrows in FIG. 4b denotes the air movement). Thereafter, the two parts are assembled together (by approaching one to the other), see FIG. 4c and taken by a dedicated tool (illustrated in FIG. 4d) to be scanned by the THz scanner.

Reference is now made to FIGS. 5-6, illustrating alternative embodiments of the sampler device. In those embodiments, the use of a capsule is redundant.

Reference is now made to FIGS. 5a-5b, showing a sampler 500 in which the membrane and the membrane housing are already integrated therewithin. The sampler is then closed and sealed and then scanned in the THz domain. Thus, there is no need for extraction of the membrane from the sampler to the capsule.

As seen in FIG. 5a, the sampler has a body 51, an upper portion 52 insertable into the tested subject's mouth (for exhale breath) and a lower portion 53. After the subject exhale breath the sampler is sealed by means of 54 and 55 closures closing the upper and lower portions (see arrows 56 and 57).

Closures 54, 55 both close the sampler and seal the same.

FIG. 5b illustrates a cross sectional view of the sampler. The membrane (and the membrane housing) are placed in location 58.

FIG. 5c illustrates another embodiment of the sampler, in which at least one of the closures is spiral-like coupled to the body of the sampler.

Reference is now made to FIGS. 5d-5e, in which closure 54 faces the upper portion 52. FIG. 5e illustrates a cross sectional view of FIG. 5d.

Reference is now made to FIG. 5f, illustrating another embodiment of the sampler, in which handles 58 are provided.

Reference is now made to FIGS. 5g-5h illustrating another embodiment of the sampler. In this embodiment, the sampler is made of 2 parts 61 and 62. Each part is composed of a body and a closure 63 and 64, respectively.

Prior to coupling the two parts, the membrane 66 (or membrane housing) is placed. Once the membrane is positioned at its location (see FIG. 5h), the sampler is ready for use.

Reference is now made to FIG. 5i illustrating another embodiment of the present invention, in which the closures 54 and 55 are provided as separate parts and not as integral part of the sampler.

Reference is now made to FIGS. 6a-6f illustrating another embodiment of the present invention, in which the sampler 500 additionally comprising Lego-like connection (71 and 72) are provided so as to enable stack like connection between the sampler prior to insertion into the THz scanner (will be illustrated herein below).

According to this embodiment, the sampler 500 comprises closures 63 and 64 where closure 64 is provided to the mouthpiece part 68 (adapted to be inserted into the subject's mouth) and closure 63 is provided to the distal most part 69 (from which the exhaled breath exits). Both closures 63 and 64 when closing the sampler are adapted to seal the same.

According to another embodiment, the sampler comprises a narrower portion 67 within the mouthpiece part 68. Said narrower portion 67 is provided so as to focus the exhaled breath to the membrane 66.

According to another embodiment, the sampler comprises a cross-like portion 74 upon which the membrane 66 is placed on. The positioning of the membrane 66 on the cross-like portion 74 results in an air flow 73 (see FIG. 6c) of the exhaled breath to reach the membrane (and absorbed therewithin) and to exit the sampler, mostly from the sideways thereof (see FIG. 6d).

Reference is now made to FIGS. 6e-6f, illustrating the samplers in their stack mode, connected to one another utilizing the Lego-like connection 71, 72.

Reference is now made to FIGS. 6g-6i, illustrating the integrated system (the sampler and the THz scanner). According to this embodiment, the integrated system comprises a THz generator module (generator) and the THz scanner (into which the samplers 500 are entered to be scanned).

FIG. 6g illustrates the THz system and the stacked samplers entering therewithin. The integrated system will also enclose a waste container to enclose all the used samplers containing the biological sample.

FIGS. 6h-6i illustrate the THz scanner and the samplers 500 entering thereto. The samplers are placed on a conveyor 501 powered by an engine 502. A camera 503 is optionally disposed therewithin to ensure the movement of the samplers 500 on the conveyor to their correct portioning in between the THz transceiver and the THz receiver (photomixer 504).

Once the samplers 500 are scanned they are disposed into the waste container 505.

Reference is now made to FIGS. 6j-6o, which illustrates another embodiment of the sampler. In which embodiment, the membrane is inserted into the sampler, then (see FIG. 6k) the mouthpiece is placed.

Next, the subject exhaled breath through the mouthpiece (see FIG. 6l). Then, the mouthpiece is extracted (see FIG. 6m).

Next, 2 closures are placed. One where the mouthpiece was connected and the second on the other distal-most part thereof. FIG. 6o illustrates the closed sampler.

FIGS. 9a-9m illustrate performance of the sampler shown e.g., in FIG. 6a and described above.

FIG. 9a illustrates a direction of air flow in the sampler according to an exemplary embodiment.

In an exemplary embodiment, the pressure drop and centered VOC accumulation were simulated. The inlet flow simulation was intended to comport with the average adult exhalation, with an average exhalation air volume of 1.1 L. A membrane was used in the simulation having a density of 8-16 kg/m^3. The average velocity flow into the sampler was 9.75 m/s. The membrane density range in at least one simulation was 9 kg/m^3 and the foam diameter was 14 mm. The pressure out was 1 atm.

In flow was simulated in three different exhalation air volume: 1 [L], 1.1[L], 1.2 [L]. Boundary air volume was tested as well: 0.5 [L], 4.8[L]. The simulation parameters were as follows: V=1.1 L→0.0011 m^3, d_c=0.006 [m]→A=π[d_c/4]^2=2.82·[10]^(−5) m^2, V·_x=V/(A·t)= 0.0011/(2.82·[10]^(−5)·4)≈9.75 m/s where ρ—foam density, d_f—diameter of foam, d_c—diameter of inlet cross-section, t—Thickness of foam, V—average amount of air a human exhale, A—cross-section of capsule, t—time of exhalation, V·_x-inlet flow.

In simulating the average adult exhalation, the volume and air speeds tested are shown in the following Table.

TABLE 1

Tested volume and air speed

| V [L] | $v \left[\frac{m}{s}\right]$ |
|---|---|
| 0.5 | 5.9 |
| 1 | 8.85 |
| 1.1 | 9.75 |
| 1.2 | 10.65 |
| 4.8 | 28 |

The amount of volume of an average human exhalation was tested by inflating a balloon.

Figure 9B:
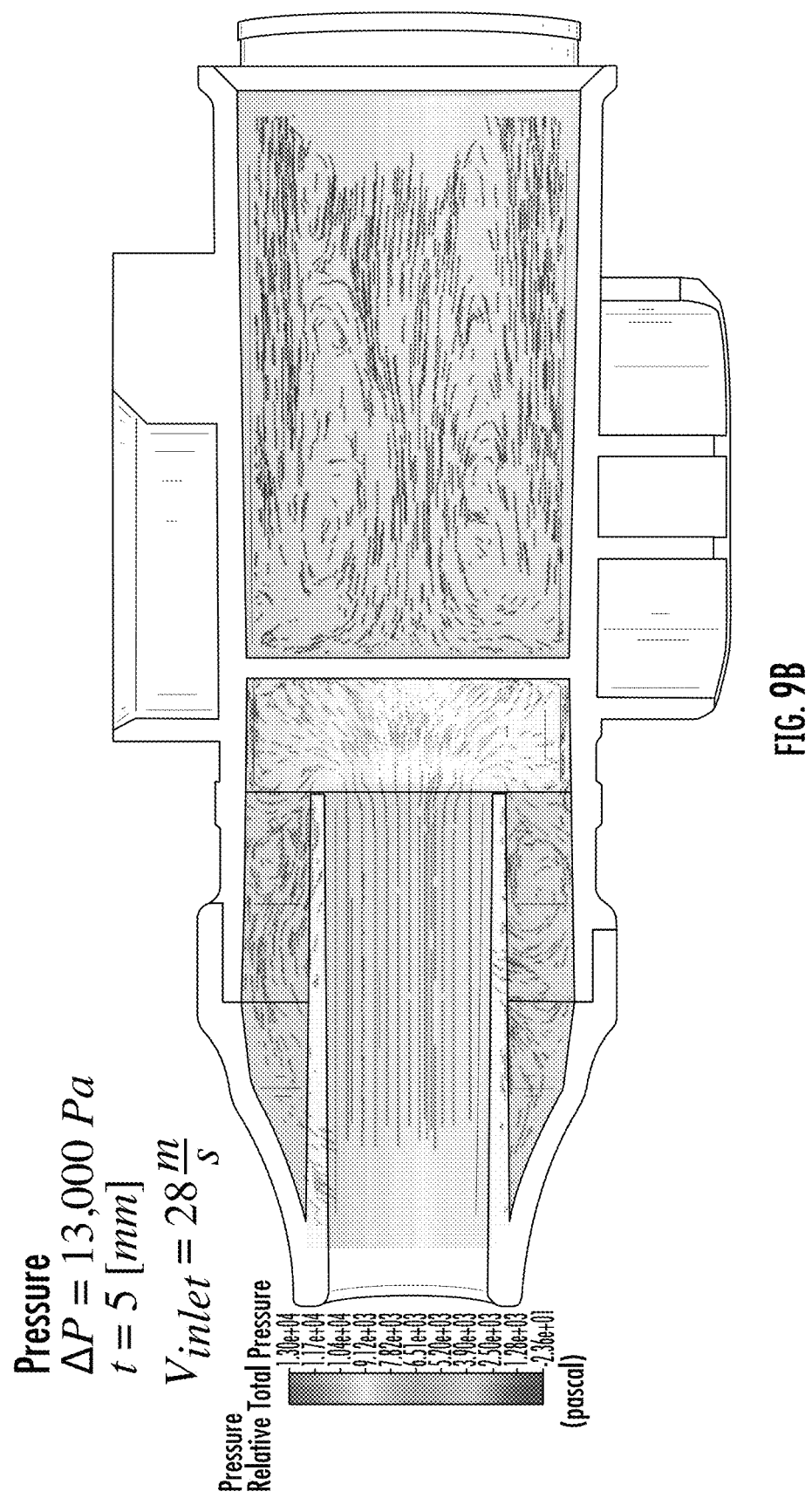
FIG. 9b illustrates performance of the sampler.
Figure 9C:
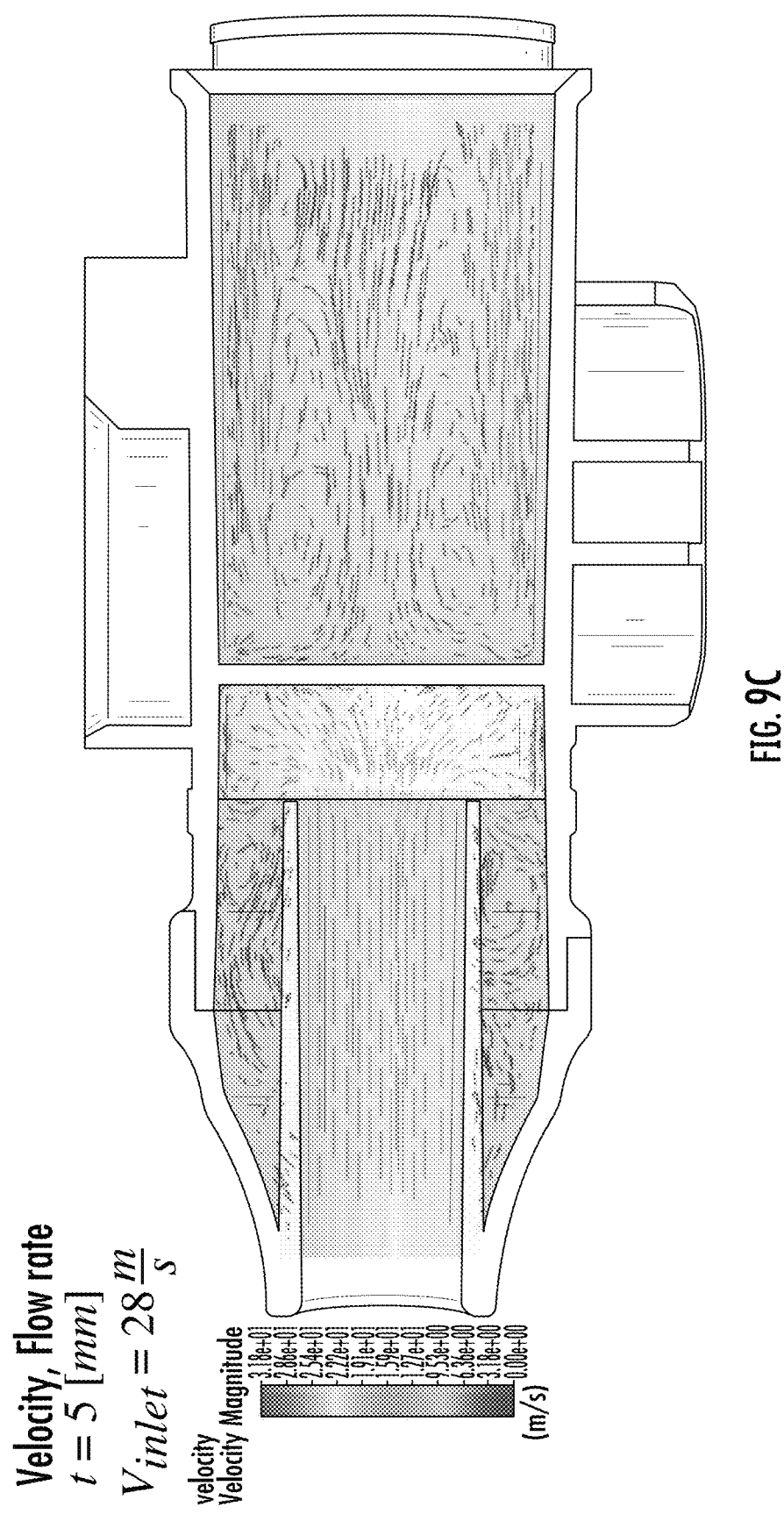
FIG. 9c illustrates performance of the sampler.

FIG. 9b depicts a simulation utilizing the sampler (the breathalyzer) of the at least one embodiment where the thickness of the foam tested was 5 mm, and the velocity of the inlet air (i.e., the exhaled air) was about 28 m/s. The figure illustrates pressure differences at different locations within the sampler. The maximum resultant pressure change is at the impact of the exhaled air and the membrane and is calculated to be ΔP=13,000 Pa. FIG. 9c depicts a velocity simulation of the inlet air (i.e., the exhaled air) at different locations within the sample. The maximum velocity was calculated to be at =28 m/s where the thickness of the foam tested was 5 mm. FIG. 9n depicts contour plots for the simulation in FIG. 9b with respect to cross-sections z1, z2, z3 and z4 (discussed in more detail with respect to FIG. 9i).

Figure 9D:
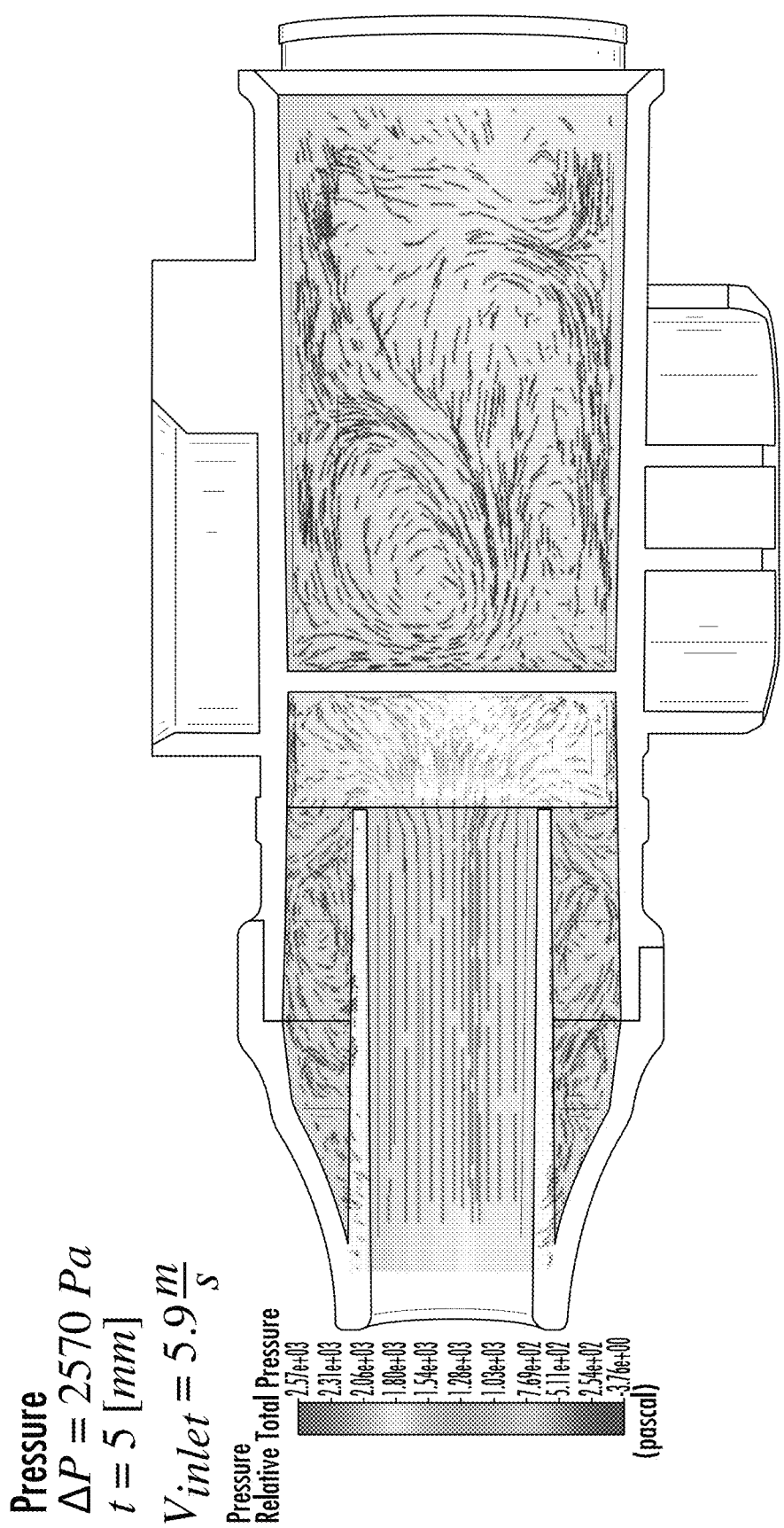
FIG. 9d illustrates performance of the sampler.
Figure 9E:
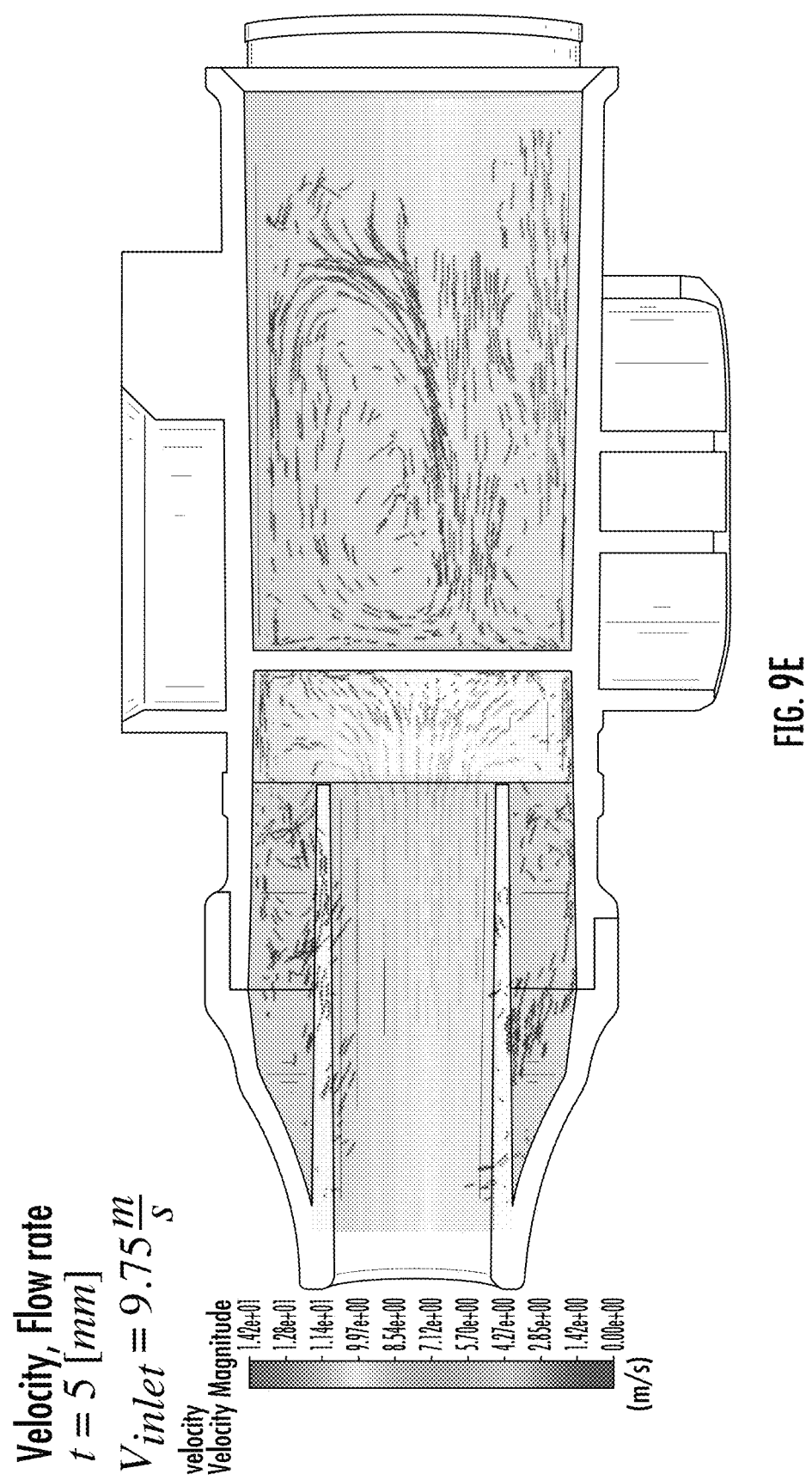
FIG. 9e illustrates performance of the sampler.
Figure 9F:
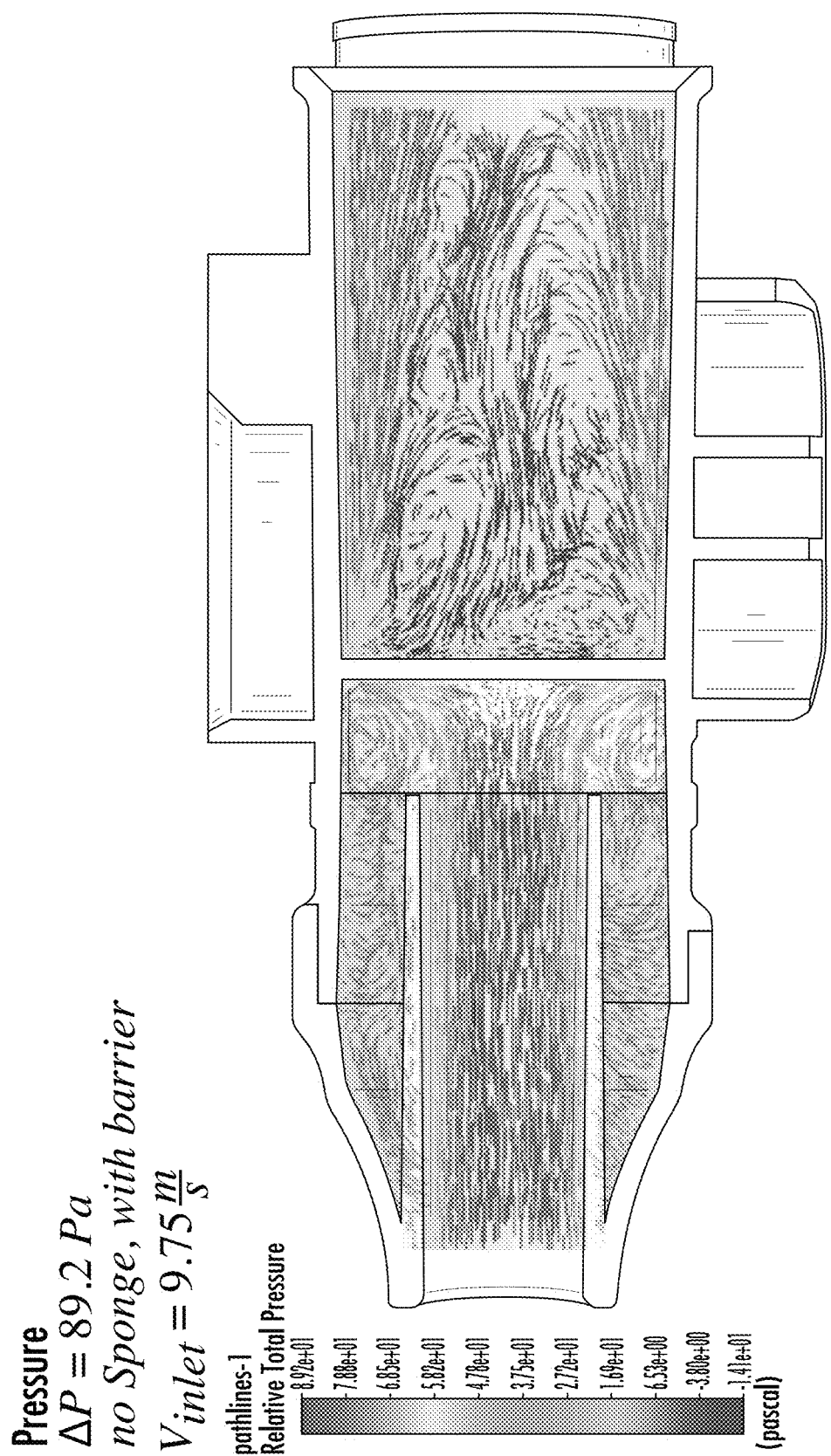
FIG. 9f illustrates performance of the sampler.
Figure 9G:
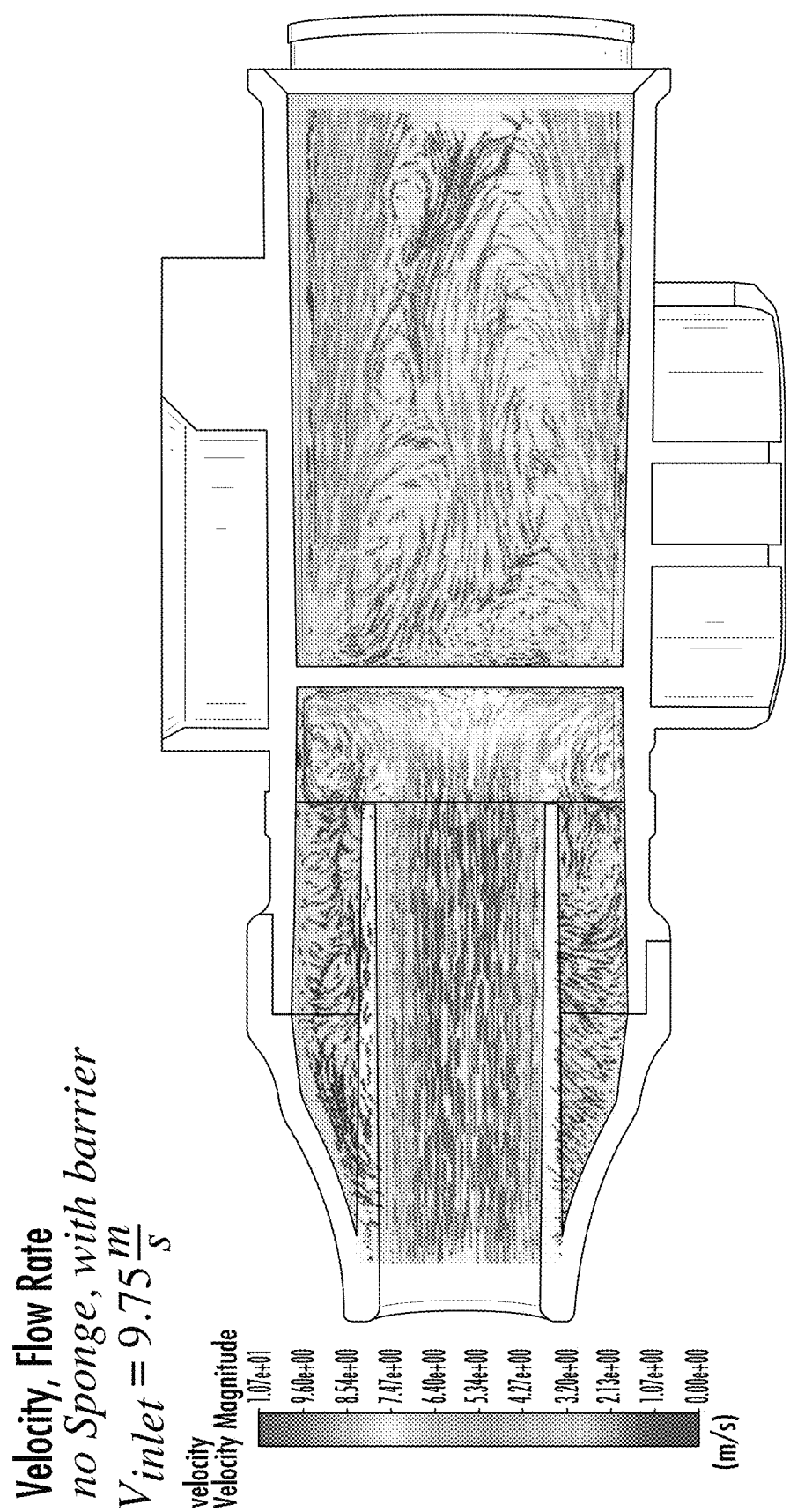
FIG. 9g illustrates performance of the sampler.

FIG. 9d depicts a pressure simulation, the same as in 9b, and the maximum resultant pressure was ΔP=2570 Pa (where the thickness of the foam tested was 5 mm and velocity of the inlet air (i.e., the exhaled air) at 9.75 m/s). FIG. 9e depicts a velocity simulation of the inlet air (i.e., the exhaled air), where the maximum velocity had reached 9.75 m/s, where the thickness of the foam tested was 5 mm. FIG. 9f depicts a pressure simulation where no membrane was utilized and a barrier (made substantially from the same material as the breathalyzer itself) was simulated, where the maximum pressure difference was calculated at ΔP=89.2 Pa. FIG. 9g depicts a velocity simulation for conditions the same as 9f of no membrane, but with a barrier present. The maximum velocity of the inlet air (i.e., the exhaled air) was calculated to be at 9.75 m/s.

FIG. 9o depicts a pressure simulation where a membrane was utilized only with a membrane (without any barrier) having thickness of 5 mm, was simulated, at ΔP=69.5 Pa. FIG. 9p depicts a velocity simulation for conditions the same as FIG. 9o, where the velocity of the inlet air (i.e., the exhaled air) was at 9.75 m/s. FIG. 9q depicts pressure contour plots for the pressure simulation of FIG. 9o. FIG. 9r depicts a pressure simulation where a membrane was utilized with a barrier having a plurality of holes therewithin was simulated, at ΔP=104 Pa. FIG. 9s depicts a velocity simulation for conditions the same as 9r, where the velocity of the inlet air (i.e., the exhaled air) was at 9.75 m/s. FIG. 9t depicts pressure contour plots for the pressure simulation of FIG. 9r where a membrane was used with a barrier having holes therein, with a membrane thickness of 5 mm and $v_{inlet}$=9.75 m/s.

To conclude the above, it was observed that ΔP [Pa] for no membrane and only with a barrier present was 89 Pa, a membrane with a dotted barrier, 104 Pa; with no barrier (only a 5 mm membrane), 69.5 Pa; with a 5 mm membrane, 4350 Pa, and with a 6 mm membrane, 4460 Pa.

Figure 9H:
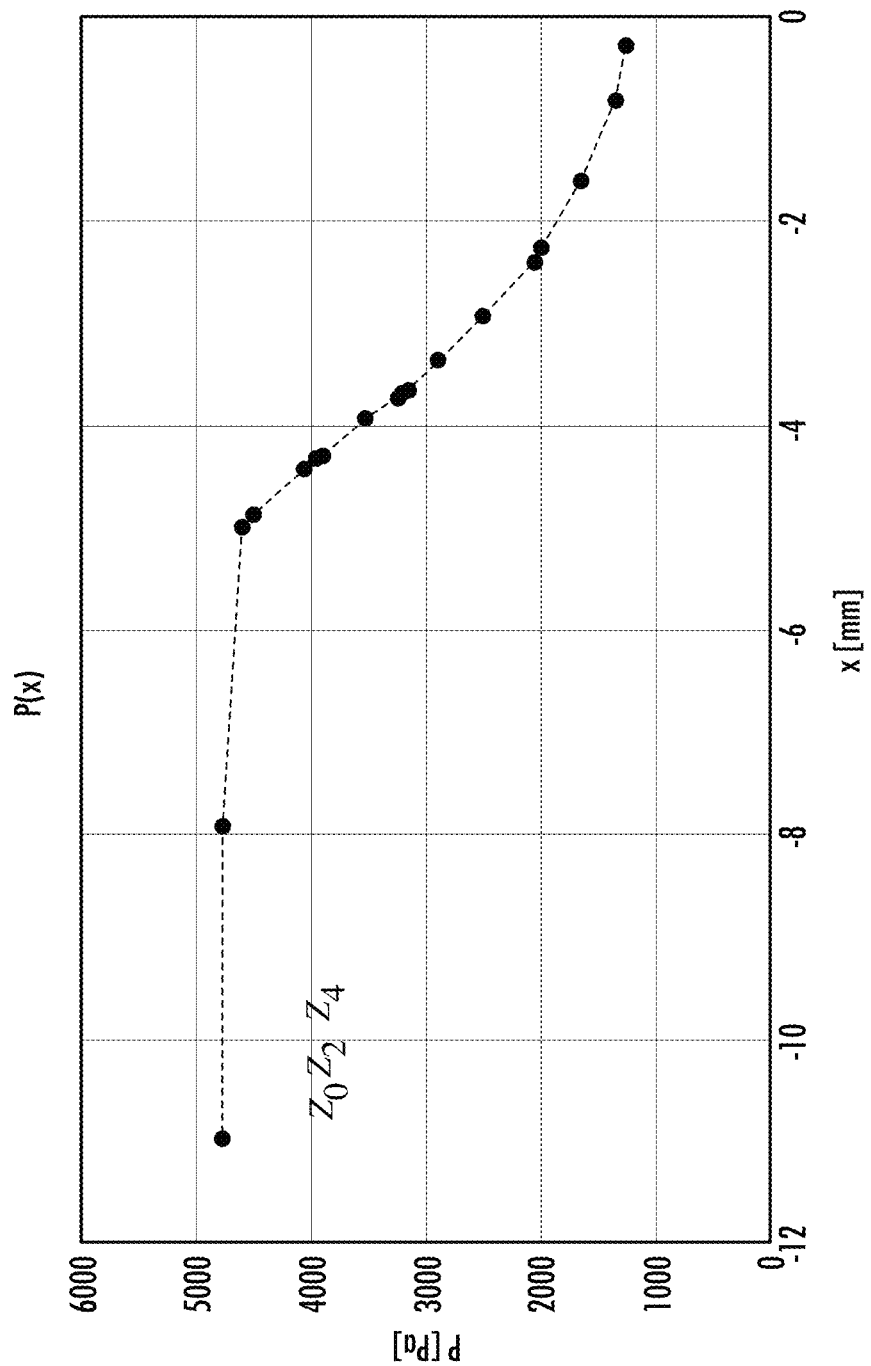
FIG. 9h illustrates performance of the sampler.
Figure 9N:
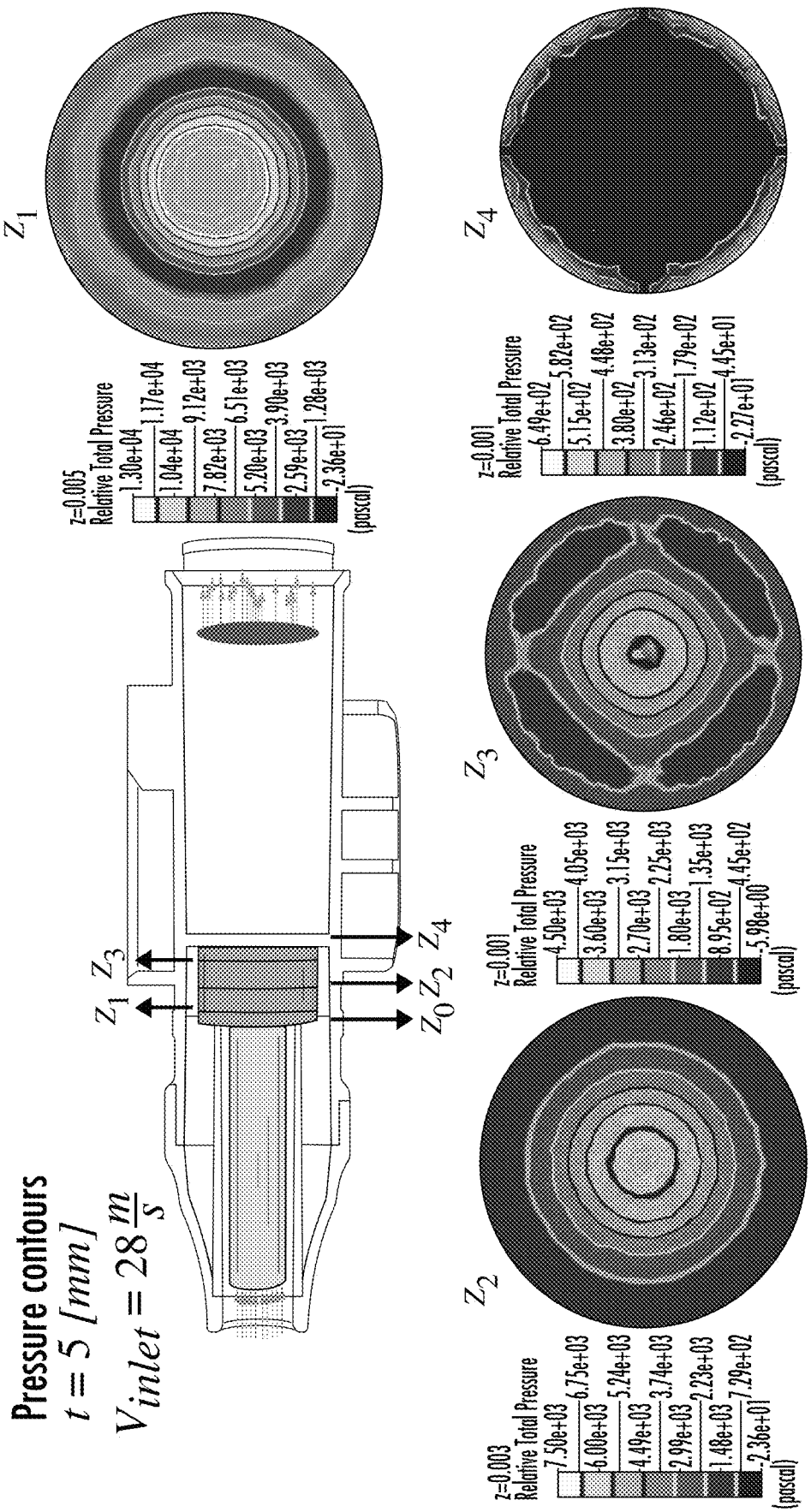
FIG. 9n illustrates contour plots of the sampler performance.
Figure 90:
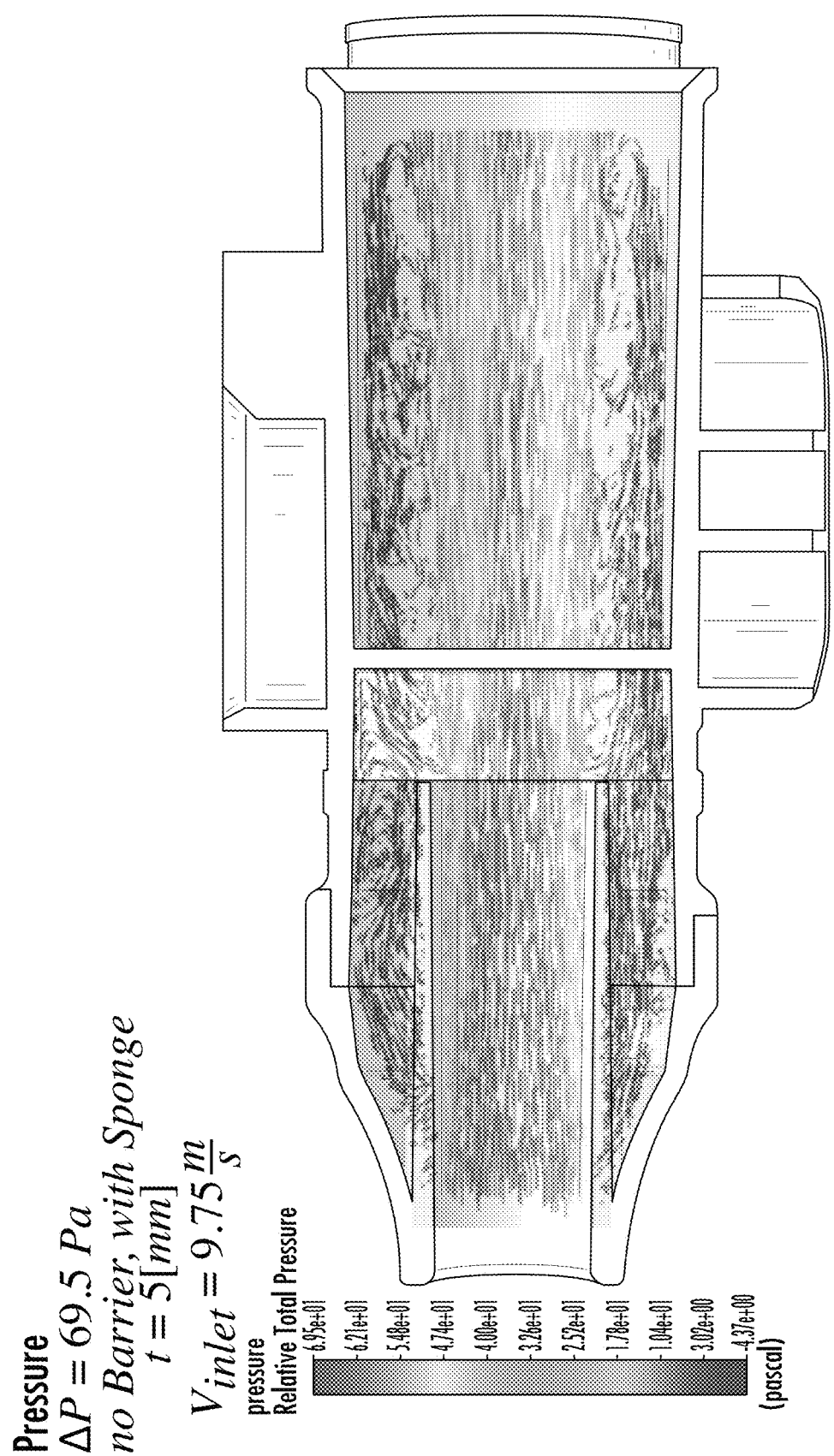
Figure 9P:
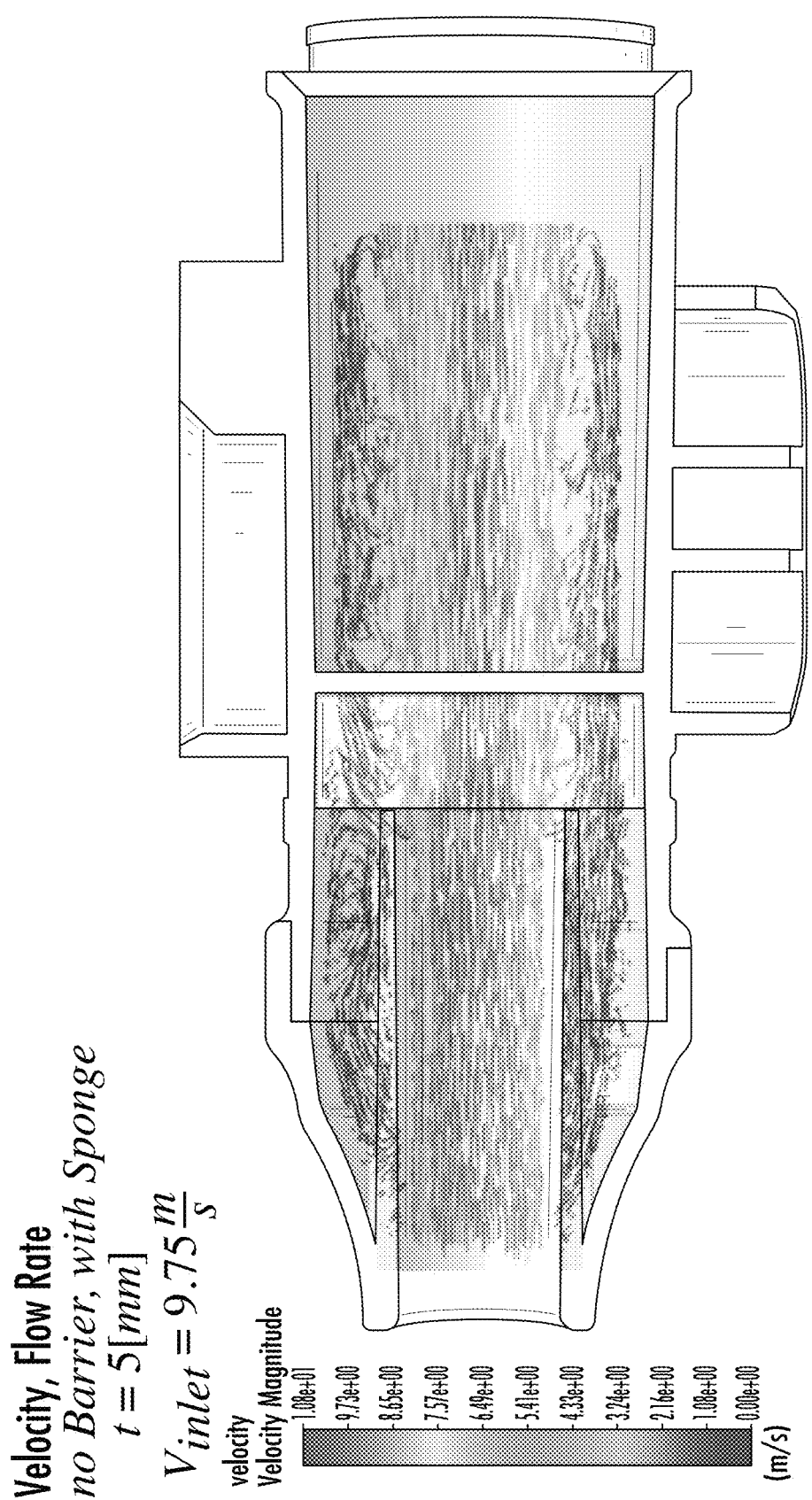
FIG. 9p illustrates performance of the sampler.
Figure 9Q:
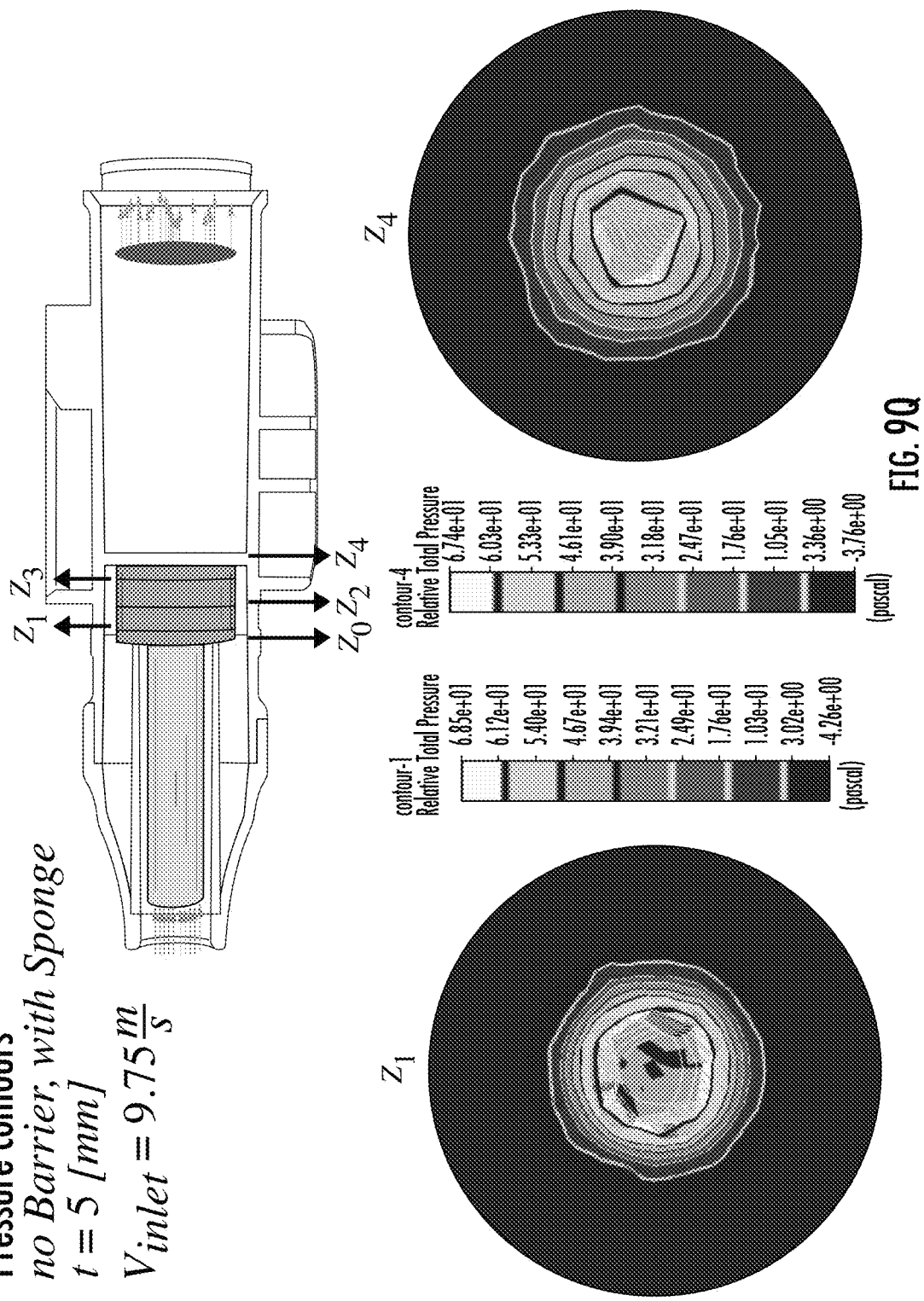
FIG. 9q illustrates contour plots of the sampler performance.
Figure 9R:
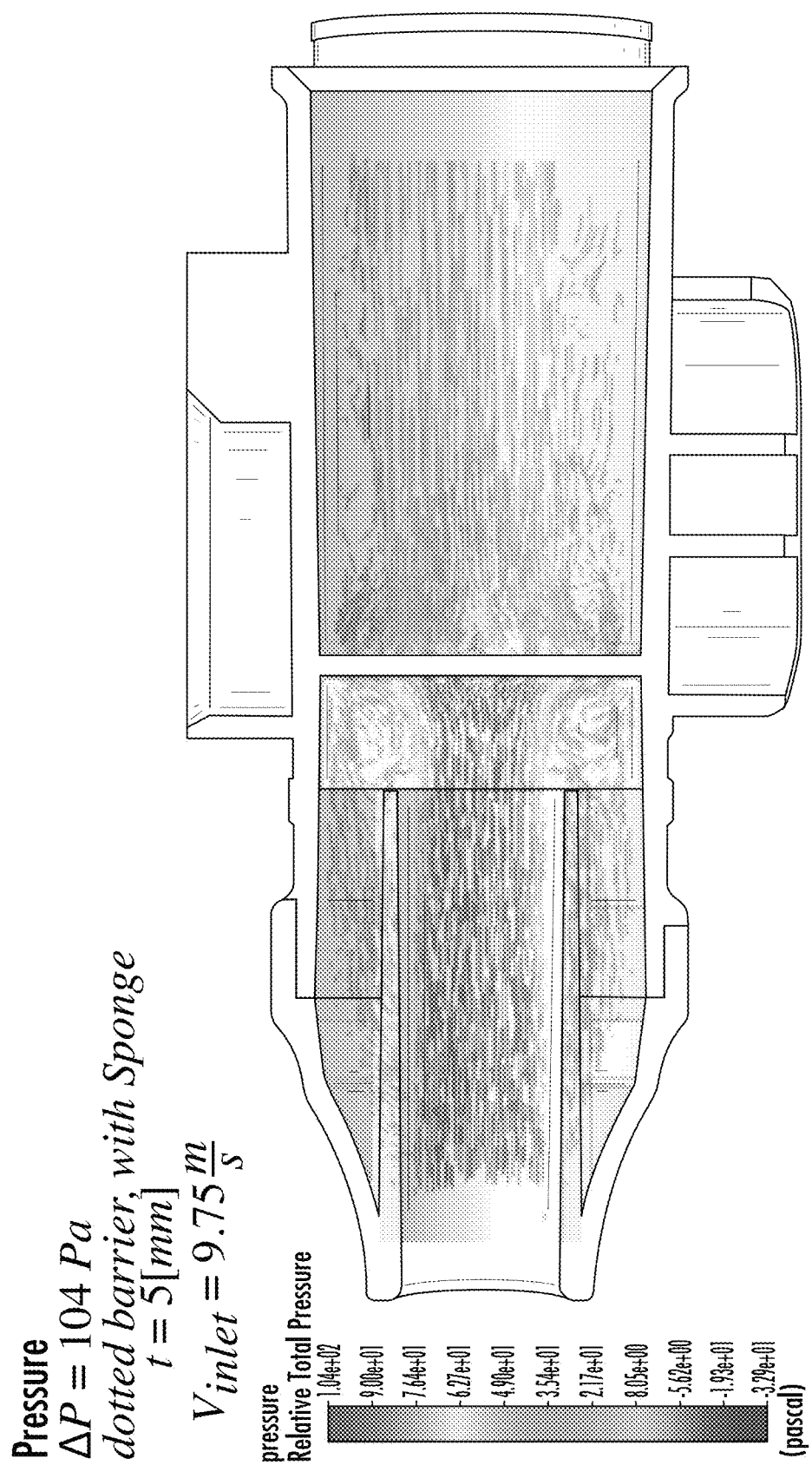
FIG. 9r illustrates performance of the sampler.
Figure 9S:
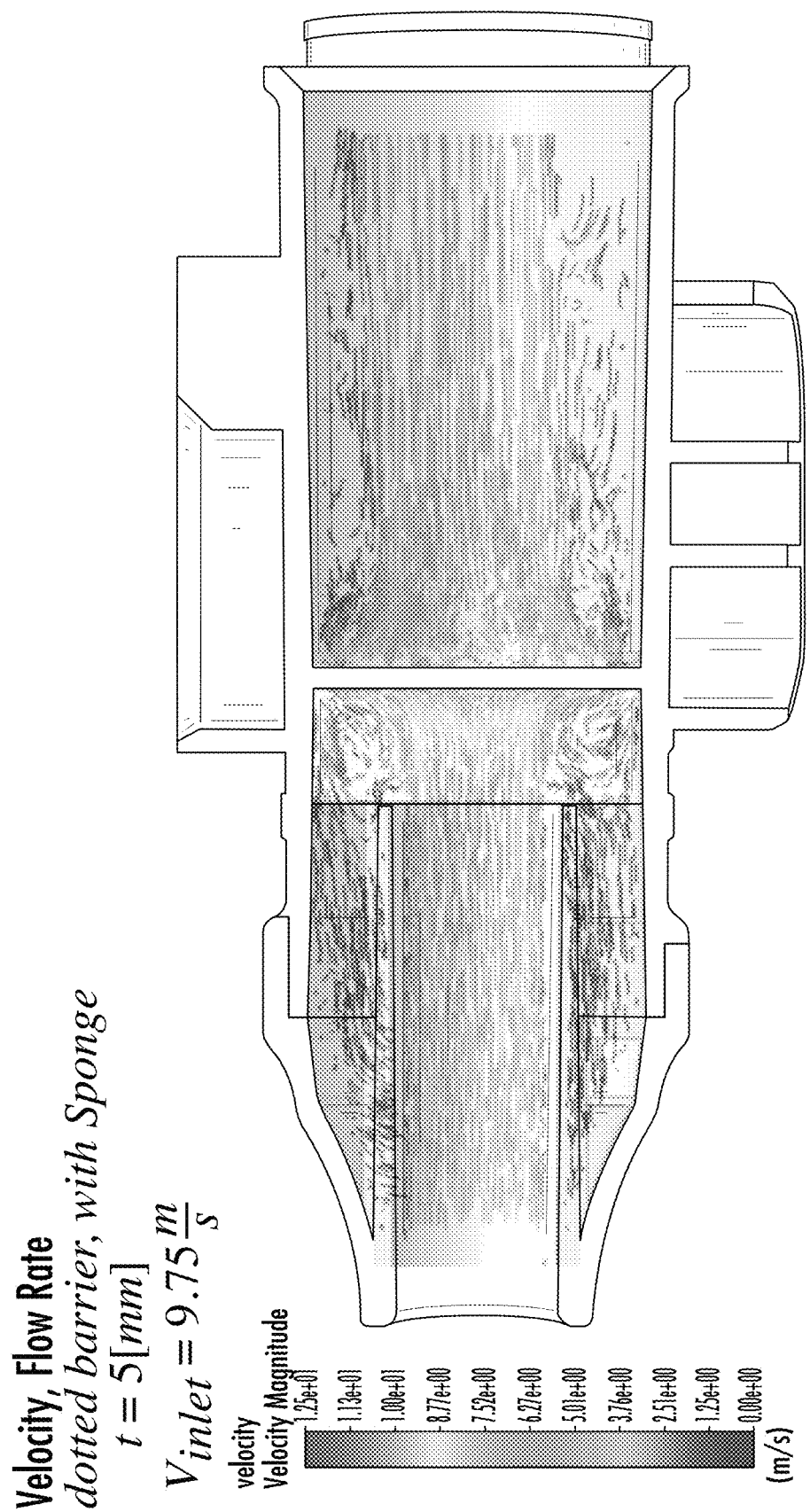
FIG. 9s illustrates performance of the sampler.

FIG. 9h depicts the pressure Pa as a function of distance (x mm) in the axial direction of the sampler. As can be seen, the maximum pressure change is at the membrane, gradually decreasing to the exit side of the sampler (the breathalyzer).

FIG. 9i depicts representative cross-sections (z0-z4) of the membrane at different 'depth' within the same; and shows the radius of the inner cross section of the sampler from a center thereof. FIG. 9j depicts pressure Pa as a function of different locations along the radius of the sampler at cross section z1 of the membrane. FIG. 9k depicts pressure as a function of different locations along the radius at cross section z2 of the membrane. FIG. 9l depicts pressure as a function of different locations along the radius at cross section z3 of the membrane. FIG. 9m depicts pressure as a function of different locations along the radius at cross section z4 of the membrane. As can be seen, other than z4 (which is a position at the distal most end of the membrane) the pressure decreases along the radius, and thus the maximum pressure is in the middle section.

Figure 7:
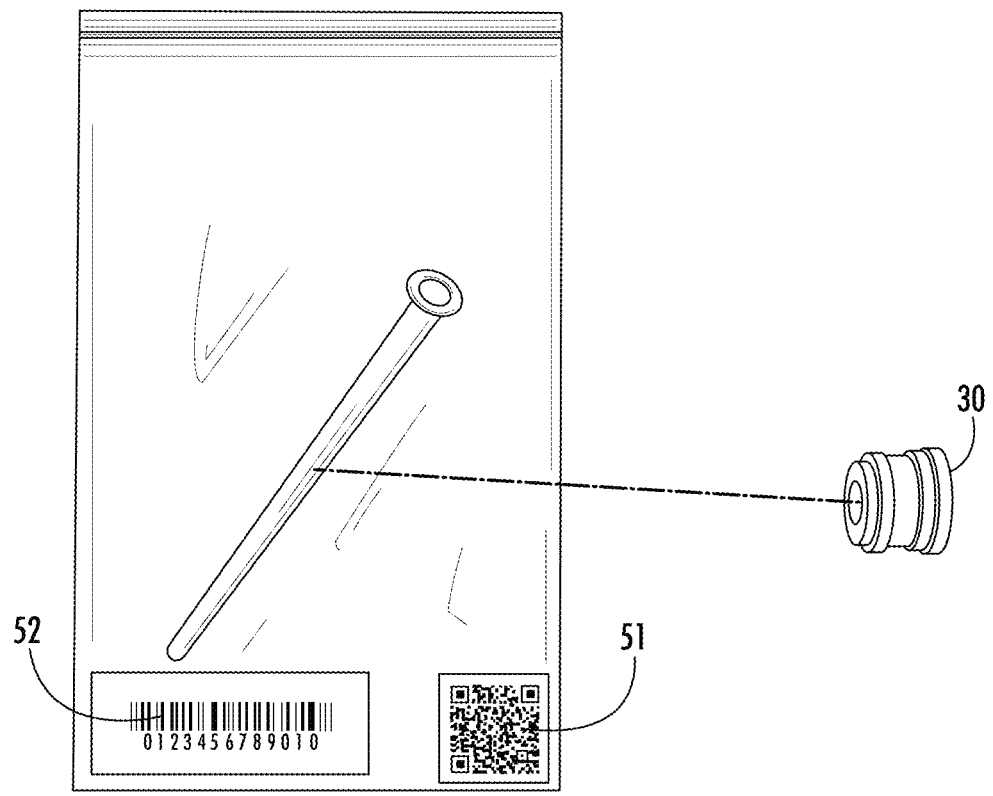
FIG. 7 depicts a component according to an embodiment.

Reference is now made to FIG. 7, illustrating an embodiment in which the membrane housing 30 is integrated in the sampler and provided as a kit with an RFID tag 51 or barcode 52. Said RFID tag 51 or barcode 52 are identifiable to each tested. Such that when the results are provided, only the tested individual the results pertain to can review the results. It also ensures no identity mistakes are made.

Thus, it is one object of the present invention to provide a high throughput system for label-free, noncontact, noninvasive, and nondestructive detection of at least one virus infected individual from at least one tested individual, the system comprising: at least one sampler comprising at least one metamaterial membrane absorber located at the propagation path of volatile compounds, VCs, and/or aerosols released by said at least one tested individual breath, said metamaterial membrane absorber being configured and operable for trapping the collected volatile compounds and/or aerosols; and a control unit configured and operable for receiving data indicative of the collected volatile compounds and/or aerosols being scanned with an electromagnetic radiation in the THz range and processing said data for identifying a signature being indicative of virus infected individuals to thereby provide detection of said virus infected individuals.

It is another object of the present invention to provide the system as defined above, wherein said THz range is between 200 GHz to 1200 GHz.

It is another object of the present invention to provide the system as defined above, wherein said tested individual is asymptomatic and has no symptom related to said virus.

It is another object of the present invention to provide the system as defined above, wherein said system distinguishes between a healthy individual, a virus recovered individual and an infected individual.

It is another object of the present invention to provide the system as defined above, wherein detection of said virus infected individuals provides clearance to healthy individuals and/or virus recovered individuals.

It is another object of the present invention to provide the system as defined above, wherein said signature is information indicative of said virus; said information being selected from a group consisting of cell unit of said virus, viral proteins, cellular debris, debris of said virus, hydrates of said virus, hydrates of debris of said virus, hydrates of the 3D structure of said virus and a cell, aggregates of said virus, cytokines, increased level of interleukin (IL)-2, interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the system as defined above, wherein said volatile compounds and/or aerosols create spoof surface plasmon polaritons (SSPPs) captured in said membrane.

It is another object of the present invention to provide the system as defined above, wherein said virus is selected from a group selected from COV viruses family, COVID-19, Influenza, Avian influenza and any combination thereof.

It is another object of the present invention to provide the system as defined above, wherein said sampler is at least one selected from a group consisting of a breathalyzer, a straw-like device, any handheld device, any IOT device into which human breath is exhaled.

It is another object of the present invention to provide the system as defined above, wherein said sampler comprises a proximal end and a distal end interconnected by a main longitudinal axis, along which said at least one metamaterial membrane is positioned; and into which said tested individual exhaled breath, such that the propagation path of said exhaled breath and volatile compounds and/or aerosols therewithin intersect said at least one metamaterial membrane and absorbed therewithin.

It is another object of the present invention to provide the system as defined above, wherein said at least one metamaterial membrane is extracted from said sampler and is placed in an electromagnetic testing unit; said electromagnetic testing unit adapted to (a) scan in the THz range said metamaterial membrane absorbed with said volatile compounds and/or aerosols in said exhale breath of said tested individual; and, (b) transmit data indicative of the collected volatile compounds and/or aerosols to said control unit.

It is another object of the present invention to provide the system as defined above, wherein said sampler comprises two parts reversibly coupled to each other along a main longitudinal axis, such that (a) said at least one metamaterial membrane is positioned therebetween along said main longitudinal axis; and, (b) into said sampler said tested individual exhale breath, such that the propagation path of said exhaled breath and volatile compounds and/or aerosols therewithin intersect said at least one metamaterial membrane and absorbed therewithin.

It is another object of the present invention to provide the system as defined above, wherein said sampler is airtight sealed such that said volatile compounds, VCs, and/or aerosols released by said at least one tested individuals breath are prevented from exiting said sampler.

It is another object of the present invention to provide the system as defined above, wherein said membrane is enclosed within at least one capsule; wherein said capsule is sealed.

It is another object of the present invention to provide the system as defined above, wherein said sampler is RFID tagged with each of said tested individual, such that detection of said virus infected individuals is traced back to each of said tested individual.

It is another object of the present invention to provide the system as defined above, wherein at least one of the following us being held true (a) said sampler is a disposable unit; (b) said sampler comprises at least one sealing element adapted to seal thereof.

It is another object of the present invention to provide the system as defined above, wherein said electromagnetic testing unit comprising at least one electromagnetic radiation transmitter and at least one electromagnetic radiation detector.

It is another object of the present invention to provide the system as defined above, wherein the membrane is positionable within the electromagnetic radiation emitted by the transmitter.

It is another object of the present invention to provide the system as defined above, wherein said data being processed by said control unit is at least one absorption spectrum of said membrane.

It is another object of the present invention to provide the system as defined above, wherein processing of said at least one absorption spectrum of said membrane additionally comprising pattern recognition of said at least one absorption spectrum.

It is another object of the present invention to provide the system as defined above, wherein said pattern recognition comprising at least one selected from a group consisting identification of special features of the pattern, identification of main and side peaks, the number of main and side peaks, the width of the peaks and the distance therebetween and any combination thereof.

It is another object of the present invention to provide the system as defined above, wherein said membrane is in communication with a vacuum source, a gas collection device coupled to the vacuum source, wherein the membrane is capable of capturing volatile compounds and/or aerosols.

It is another object of the present invention to provide the system as defined above, wherein said membrane is cleaned by applying at least one selected from a group consisting of positive/negative pressure or electricity to release said VCs and/or aerosols.

It is another object of the present invention to provide the system as defined above, wherein said membrane is coated with at least one material selected from a group consisting of Silicon, or Silicon Graphene, acting as a reflector, and any combination thereof.

It is another object of the present invention to provide the system as defined above, wherein said membrane is made of at least one material selected from a group consisting of Meta-Material Membrane, Semi Pressure Permeable Membrane, meta-material, PET, melamine open-cell foam-based and any combination thereof.

It is another object of the present invention to provide the system as defined above, wherein said control unit is configured and operable for performing a pattern recognition of said signature.

It is another object of the present invention to provide the system as defined above, wherein said system additionally comprising at one communicable and readable database; said database comprising collected volatile compounds and/or aerosols being scanned with an electromagnetic radiation in the THz range.

It is another object of the present invention to provide the system as defined above, wherein said system has 2 modes of operation: (a) a learning phase; and, (b) a detection phase.

It is another object of the present invention to provide the system as defined above, wherein, in said learning phase, said control unit trains a machine learning model to detect at least one parameter in the absorption spectrum of said membrane with said collected volatile compounds and/or aerosols being scanned with an electromagnetic radiation in the THz range of a plurality of membrane stored in said communicable and readable database in order to generate information data being indicative of said virus infected individuals.

It is another object of the present invention to provide the system as defined above, wherein said parameter selected from a group consisting of, trends in said database of said at least one tested individuals, eigenvector of said database of said at least one tested individuals, eigenvalues of said database of said at least one tested individuals, feature extraction step being configured to estimate the most relevant vectors defining the data using a principal component analysis, a pattern classification using a combined linear and nonlinear pattern recognition approach, known symptoms of said virus, known healthy individuals, healthy individual vital signs selected from fever, sweat, body temperature, blood pressure, pulse (heart rate), and breathing rate (respiratory rate) and any combination thereof, virus infected individual vital signs selected from fever, sweat, body temperature, blood pressure, pulse (heart rate), and breathing rate (respiratory rate) and any combination thereof, medicaments being administered to said tested individual, and any combination thereof.

It is another object of the present invention to provide the system as defined above, wherein, in said learning phase, said data is either supervised or unsupervised data; and, said training by said control unit is performed by at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds and/or aerosols being scanned with an electromagnetic radiation in the THz range stored in said communicable and readable database in order to generate information data being indicative of at least one said virus infected individuals.

It is another object of the present invention to provide the system as defined above, wherein, in said detection phase, said data is either supervised or unsupervised data; and, said control unit performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds and/or aerosols being scanned with an electromagnetic radiation in the THz range stored in said communicable and readable database in order to generate information data being indicative of at least one said virus infected individuals.

It is another object of the present invention to provide the system as defined above, wherein, in said detection phase, said control unit detects said signature the absorption spectrum of said membrane with said VCs and/or aerosols being indicative of at least one said virus infected individuals by means of said trained machine learning model.

It is another object of the present invention to provide the system as defined above, wherein said system additionally comprising at least one communicable and readable database storing instructions which, when executed by the at least one data processor, result in operations comprising:

training a machine learning model to detect at least one parameter of said collected volatile compounds and/or aerosols being scanned with an electromagnetic radiation in the THz range of at least one tested individuals stored in said communicable and readable database in order to generate information data being indicative of said virus infected individuals; and, after said step of training, real time detecting said parameter by means of said trained machine learning model.

It is another object of the present invention to provide the system as defined above, wherein said data is either supervised or unsupervised data; and, said control unit performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof in order to generate information data being indicative of said virus infected individuals.

It is another object of the present invention to provide the system as defined above, wherein said control unit additionally performs Fast Fourier Transformation in order to generate information data being indicative of said virus infected individuals.

It is another object of the present invention to provide the system as defined above, wherein said membrane is made of hardened extruded plastic.

It is another object of the present invention to provide the system as defined above, wherein said membrane is able to trap at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl tri sulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, $NO_2$ and any combination thereof.

It is another object of the present invention to provide the system as defined above, wherein said membrane is single-use, disposable membrane.

It is another object of the present invention to provide the system as defined above, wherein said membrane is reusable.

It is another object of the present invention to provide the system as defined above, wherein said volatile compounds and/or aerosols comprising at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, $NO_2$ and any combination thereof.

It is another object of the present invention to provide the system as defined above, wherein said membrane is removable from the sampling apparatus.

It is another object of the present invention to provide the system as defined above, wherein said detection is completed within a period of time being less than 40 seconds.

It is another object of the present invention to provide the system as defined above, further comprising a spectroscopic assembly including a radiation transmitter unit being configured and operable to scan said permeable membrane holding the collected volatile compounds and/or aerosols by generating an electromagnetic radiation in the range of THz within a scanning window of about 100 GHz and a detection unit being configured and operable to detect an electromagnetic radiation emitted by said collected volatile compounds and/or aerosols.

It is another object of the present invention to provide the system as defined above, wherein said system additionally comprising signaling means adapted to signal the user that sufficient enough of VCs and/or aerosols have been captured in said membrane or that said detection has been completed.

It is another object of the present invention to provide the system as defined above, wherein said signaling means are either optical or vocal means.

It is another object of the present invention to provide a high throughput system for label-free, noncontact, noninvasive, and nondestructive detection of at least one virus infected individuals from at least one tested individual, the system comprising: at least one sampler comprising at least one metamaterial membrane absorber located at the propagation path of volatile compounds, VCs, and/or aerosols released by said at least one tested individuals breath, said metamaterial membrane absorber being configured and operable for trapping the collected volatile compounds and/or aerosols;

at least one electromagnetic testing unit comprising at least one electromagnetic radiation transmitter and at least one electromagnetic radiation detector; said membrane, after absorbing said volatile compounds and/or aerosols, being positionable within the electromagnetic radiation emitted by said at least one transmitter; such that said electromagnetic testing unit adapted to (a) scan in the THz range said metamaterial membrane absorbed with said volatile compounds and/or aerosols in said exhaled breath of said tested individual; and, (b) transmit data indicative of the collected volatile compounds and/or aerosols to said control unit;

a control unit configured and operable for receiving data indicative of the collected volatile compounds and/or aerosols from said electromagnetic testing unit and processing said data for identifying a signature being indicative of virus infected individuals to thereby provide detection of said virus infected individuals.

It is another object of the present invention to provide the system as defined above, wherein said THz range is between 200 GHz to 1200 GHz.

It is another object of the present invention to provide the system as defined above, wherein said tested individual is asymptomatic and has no symptom related to said virus.

It is another object of the present invention to provide the system as defined above, wherein said system distinguishes between a healthy individual, a virus recovered individual and an infected individual.

It is another object of the present invention to provide the system as defined above, wherein detection of said virus infected individuals provides clearance to healthy individuals and/or virus recovered individuals.

It is another object of the present invention to provide the system as defined above, wherein said signature is information indicative of said virus; said information being selected from a group consisting of cell unit of said virus, viral proteins, cellular debris, debris of said virus, hydrates of said virus, hydrates of debris of said virus, hydrates of the 3D structure of said virus and a cell, aggregates of said virus, cytokines, increased level of interleukin (IL)-2, interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the system as defined above, wherein said volatile compounds and/or aerosols create spoof surface plasmon polaritons (SSPPs) captured in said membrane.

It is another object of the present invention to provide the system as defined above, wherein said virus is selected from a group selected from COV viruses family, COVID-19, Influenza, Avian influenza and any combination thereof.

It is another object of the present invention to provide the system as defined above, wherein said sampler is at least one selected from a group consisting of a breathalyzer, a straw-like device, any handheld device, any IOT device into which human breath is exhaled.

It is another object of the present invention to provide the system as defined above, wherein said sampler comprises a proximal end and a distal end interconnected by a main longitudinal axis, along which said at least one metamaterial membrane is positioned; and into which said tested individual exhale breath, such that the propagation path of said exhaled breath and volatile compounds and/or aerosols therewithin intersect said at least one metamaterial membrane and absorbed therewithin.

It is another object of the present invention to provide the system as defined above, wherein said sampler is airtight sealed such that said volatile compounds, VCs, and/or aerosols released by said at least one tested individuals breath are prevented from exiting said sampler.

It is another object of the present invention to provide the system as defined above, wherein said membrane is enclosed within at least one capsule; wherein said capsule is sealed.

It is another object of the present invention to provide the system as defined above, wherein said sampler is RFID tagged with each of said tested individual, such that detection of said virus infected individuals is traced back to each of said tested individual.

It is another object of the present invention to provide the system as defined above, wherein at least one of the following us being held true (a) said sampler is a disposable unit; (b) said sampler comprises at least one sealing element adapted to seal thereof.

It is another object of the present invention to provide the system as defined above, wherein said data being processed by said control unit is at least one absorption spectrum of said membrane.

It is another object of the present invention to provide the system as defined above, wherein processing of said at least one absorption spectrum of said membrane additionally comprising pattern recognition of said at least one absorption spectrum.

It is another object of the present invention to provide the system as defined above, wherein said pattern recognition comprising at least one selected from a group consisting identification of special features of the pattern, identification of main and side peaks, the number of main and side peaks, the width of the peaks and the distance therebetween and any combination thereof.

It is another object of the present invention to provide the system as defined above, wherein said membrane is in communication with a vacuum source, a gas collection device coupled to the vacuum source, wherein the membrane is capable of capturing volatile compounds and/or aerosols.

It is another object of the present invention to provide the system as defined above, wherein said membrane is cleaned by applying at least one selected from a group consisting of positive/negative pressure or electricity to release said VCs and/or aerosols.

It is another object of the present invention to provide the system as defined above, wherein said membrane is coated with at least one material selected from a group consisting of Silicon, or Silicon Graphene, acting as a reflector, and any combination thereof.

It is another object of the present invention to provide the system as defined above, wherein said membrane is made of at least one material selected from a group consisting of Meta-Material Membrane, Semi Pressure Permeable Membrane, meta-material, PET, melamine open-cell foam-based and any combination thereof.

It is another object of the present invention to provide the system as defined above, wherein said control unit is configured and operable for performing a pattern recognition of said signature.

It is another object of the present invention to provide the system as defined above, wherein said system additionally comprising at one communicable and readable database; said database comprising collected volatile compounds and/or aerosols being scanned with an electromagnetic radiation in the THz range.

It is another object of the present invention to provide the system as defined above, wherein said system has 2 modes of operation: (a) a learning phase; and, (b) a detection phase.

It is another object of the present invention to provide the system as defined above, wherein, in said learning phase, said control unit trains a machine learning model to detect at least one parameter in the absorption spectrum of said membrane with said collected volatile compounds and/or aerosols being scanned with an electromagnetic radiation in the THz range of a plurality of membrane stored in said communicable and readable database in order to generate information data being indicative of said virus infected individuals.

It is another object of the present invention to provide the system as defined above, wherein aid parameter selected from a group consisting of, trends in said database of said at least one tested individuals, eigenvector of said database of said at least one tested individuals, eigenvalues of said database of said at least one tested individuals, feature extraction step being configured to estimate the most relevant vectors defining the data using a principal component analysis, a pattern classification using a combined linear and nonlinear pattern recognition approach, known symptoms of said virus, known healthy individuals, healthy individual vital signs selected from fever, sweat, body temperature, blood pressure, pulse (heart rate), and breathing rate (respiratory rate) and any combination thereof, virus infected individual vital signs selected from fever, sweat, body temperature, blood pressure, pulse (heart rate), and breathing rate (respiratory rate) and any combination thereof, medicaments being administered to said tested individual, and any combination thereof.

It is another object of the present invention to provide the system as defined above, wherein, in said learning phase, said data is either supervised or unsupervised data; and, said training by said control unit is performed by at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds and/or aerosols being scanned with an electromagnetic radiation in the THz range stored in said communicable and readable database in order to generate information data being indicative of at least one said virus infected individuals.

It is another object of the present invention to provide the system as defined above, wherein, in said detection phase, said data is either supervised or unsupervised data; and, said control unit performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds and/or aerosols being scanned with an electromagnetic radiation in the THz range stored in said communicable and readable database in order to generate information data being indicative of at least one said virus infected individuals.

It is another object of the present invention to provide the system as defined above, wherein, in said detection phase, said control unit detects said signature the absorption spectrum of said membrane with said VCs and/or aerosols being indicative of at least one said virus infected individuals by means of said trained machine learning model.

It is another object of the present invention to provide the system as defined above, wherein said system additionally comprising at least one communicable and readable database storing instructions which, when executed by the at least one data processor, result in operations comprising:

training a machine learning model to detect at least one parameter of said collected volatile compounds and/or aerosols being scanned with an electromagnetic radiation in the THz range of at least one tested individuals stored in said communicable and readable database in order to generate information data being indicative of said virus infected individuals; and, After said step of training, real time detecting said parameter by means of said trained machine learning model.

It is another object of the present invention to provide the system as defined above, wherein said data is either supervised or unsupervised data; and, said control unit performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof in order to generate information data being indicative of said virus infected individuals.

It is another object of the present invention to provide the system as defined above, wherein said control unit additionally performs Fast Fourier Transformation in order to generate information data being indicative of said virus infected individuals.

It is another object of the present invention to provide the system as defined above, wherein said membrane is made of hardened extruded plastic.

It is another object of the present invention to provide the system as defined above, wherein said membrane is able to trap at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, $NO_2$, viral proteins, cellular debris, debris of said virus, hydrates of said virus, hydrates of debris of said virus, hydrates of the 3D structure of said virus and a cell, aggregates of said virus, cytokines, increased level of interleukin interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the system as defined above, wherein said membrane is single-use, disposable membrane.

It is another object of the present invention to provide the system as defined above, wherein said membrane is reusable.

It is another object of the present invention to provide the system as defined above, wherein said volatile compounds and/or aerosols comprising at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1 cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, $NO_2$, viral proteins, cellular debris, debris of said virus, hydrates of said virus, hydrates of debris of said virus, hydrates of the 3D structure of said virus and a cell, aggregates of said virus, cytokines, increased level of interleukin (IL)-2, interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the system as defined above, wherein said membrane is removable from the sampling apparatus.

It is another object of the present invention to provide the system as defined above, wherein said detection is completed within a period of time being less than 40 seconds.

It is another object of the present invention to provide the system as defined above, further comprising a spectroscopic assembly including a radiation transmitter unit being configured and operable to scan said permeable membrane holding the collected volatile compounds and/or aerosols by generating an electromagnetic radiation in the range of THz within a scanning window of about 100 GHz and a detection unit being configured and operable to detect an electromagnetic radiation emitted by said collected volatile compounds and/or aerosols.

It is another object of the present invention to provide the system as defined above, wherein said system additionally comprising signaling means adapted to signal the user that sufficient enough of VCs and/or aerosols have been captured in said membrane or that said detection has been completed.

It is another object of the present invention to provide the system as defined above, wherein said signaling means are either optical or vocal means.

It is another object of the present invention to provide a sampler to be integrated into a system for label-free, noncontact, noninvasive, and nondestructive detection of at least one virus infected individuals from at least one tested individual, the sampler comprising: a proximal end and a distal end interconnected by a main longitudinal axis, along which at least one metamaterial membrane absorber is positioned; and into which said tested individual exhale breath, such that the propagation path of said exhaled breath and volatile compounds, VCs, and/or aerosols therewithin intersect said at least one metamaterial membrane and absorbed therewithin; said metamaterial membrane absorber being configured and operable for trapping the collected volatile compounds and/or aerosols.

It is another object of the present invention to provide the sampler as defined above, wherein said system additionally comprising a control unit configured and operable for receiving data indicative of the collected volatile compounds and/or aerosols being scanned with an electromagnetic radiation in the THz range and processing said data for identifying a signature being indicative of virus infected individuals to thereby provide detection of said virus infected individuals.

It is another object of the present invention to provide the sampler as defined above, wherein said sampler is airtight sealed such that said volatile compounds, VCs, and/or aerosols released by said at least one tested individuals breath are prevented from exiting said sampler.

It is another object of the present invention to provide the sampler as defined above, wherein said membrane is enclosed within at least one capsule; wherein said capsule is sealed.

It is another object of the present invention to provide the sampler as defined above, wherein said sampler is RFID tagged with each of said tested individual, such that detection of said virus infected individuals is traced back to each of said tested individual.

It is another object of the present invention to provide the sampler as defined above, wherein at least one of the following us being held true (a) said sampler is a disposable unit; (b) said sampler comprises at least one sealing element adapted to seal thereof.

It is another object of the present invention to provide the sampler as defined above, wherein said THz range is between 200 GHz to 1200 GHz.

It is another object of the present invention to provide the sampler as defined above, wherein said tested individual is asymptomatic and has no symptom related to said virus.

It is another object of the present invention to provide the sampler as defined above, wherein said system distinguishes between a healthy individual, a virus recovered individual and an infected individual.

It is another object of the present invention to provide the sampler as defined above, wherein detection of said virus infected individuals provides clearance to healthy individuals and/or virus recovered individuals.

It is another object of the present invention to provide the sampler as defined above, wherein said signature is information indicative of said virus; said information being selected from a group consisting of cell unit of said virus, viral proteins, cellular debris, debris of said virus, hydrates of said virus, hydrates of debris of said virus, hydrates of the 3D structure of said virus and a cell, aggregates of said virus, cytokines, increased level of interleukin interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the sampler as defined above, wherein said volatile compounds and/or aerosols create spoof surface plasmon polaritons (SSPPs) captured in said membrane.

It is another object of the present invention to provide the sampler as defined above, wherein said virus is selected from a group selected from COV viruses family, COVID-19, Influenza, Avian influenza and any combination thereof.

It is another object of the present invention to provide the sampler as defined above, wherein said sampler is at least one selected from a group consisting of a breathalyzer, a straw-like device, any handheld device, any IOT device into which human breath is exhaled.

It is another object of the present invention to provide the sampler as defined above, wherein said at least one metamaterial membrane is extracted from said sampler and is placed in an electromagnetic testing unit; said electromagnetic testing unit adapted to (a) scan in the THz range said metamaterial membrane absorbed with said volatile compounds and/or aerosols in said exhaled breath of said tested individual; and, (b) transmit data indicative of the collected volatile compounds and/or aerosols to said control unit.

It is another object of the present invention to provide the sampler as defined above, wherein said sampler comprises two parts reversibly coupled to each other along a main longitudinal axis, such that (a) said at least one metamaterial membrane is positioned therebetween along said main longitudinal axis; and, (b) into said sampler said tested individual exhale breath, such that the propagation path of said exhaled breath and volatile compounds and/or aerosols therewithin intersect said at least one metamaterial membrane and absorbed therewithin.

It is another object of the present invention to provide the sampler as defined above, wherein said electromagnetic testing unit comprising at least one electromagnetic radiation transmitter and at least one electromagnetic radiation detector.

It is another object of the present invention to provide the sampler as defined above, wherein the membrane is positionable within the electromagnetic radiation emitted by the transmitter.

It is another object of the present invention to provide the sampler as defined above, wherein said data being processed by said control unit is at least one absorption spectrum of said membrane.

It is another object of the present invention to provide the sampler as defined above, wherein processing of said at least one absorption spectrum of said membrane additionally comprising pattern recognition of said at least one absorption spectrum.

It is another object of the present invention to provide the sampler as defined above, wherein said pattern recognition comprising at least one selected from a group consisting identification of special features of the pattern, identification of main and side peaks, the number of main and side peaks, the width of the peaks and the distance therebetween and any combination thereof.

It is another object of the present invention to provide the sampler as defined above, wherein said membrane is in communication with a vacuum source, a gas collection device coupled to the vacuum source, wherein the membrane is capable of capturing volatile compounds and/or aerosols.

It is another object of the present invention to provide the sampler as defined above, wherein said membrane is cleaned by applying at least one selected from a group consisting of positive/negative pressure or electricity to release said VCs and/or aerosols.

It is another object of the present invention to provide the sampler as defined above, wherein said membrane is coated with at least one material selected from a group consisting of Silicon, or Silicon Graphene, acting as a reflector, and any combination thereof.

It is another object of the present invention to provide the sampler as defined above, wherein said membrane is made of at least one material selected from a group consisting of Meta-Material Membrane, Semi Pressure Permeable Membrane, meta-material, PET, melamine open-cell foam-based and any combination thereof.

It is another object of the present invention to provide the sampler as defined above, wherein said control unit is configured and operable for performing a pattern recognition of said signature.

It is another object of the present invention to provide the sampler as defined above, wherein said system additionally comprising at one communicable and readable database; said database comprising collected volatile compounds and/or aerosols being scanned with an electromagnetic radiation in the THz range.

It is another object of the present invention to provide the sampler as defined above, wherein said system has 2 modes of operation: (a) a learning phase; and, (b) a detection phase.

It is another object of the present invention to provide the sampler as defined above, wherein, in said learning phase, said control unit trains a machine learning model to detect at least one parameter in the absorption spectrum of said membrane with said collected volatile compounds and/or aerosols being scanned with an electromagnetic radiation in the THz range of a plurality of membrane stored in said communicable and readable database in order to generate information data being indicative of said virus infected individuals.

It is another object of the present invention to provide the sampler as defined above, wherein aid parameter selected from a group consisting of, trends in said database of said at least one tested individuals, eigenvector of said database of said at least one tested individuals, eigenvalues of said database of said at least one tested individuals, feature extraction step being configured to estimate the most relevant vectors defining the data using a principal component analysis, a pattern classification using a combined linear and nonlinear pattern recognition approach, known symptoms of said virus, known healthy individuals, healthy individual vital signs selected from fever, sweat, body temperature, blood pressure, pulse (heart rate), and breathing rate (respiratory rate) and any combination thereof, virus infected individual vital signs selected from fever, sweat, body temperature, blood pressure, pulse (heart rate), and breathing rate (respiratory rate) and any combination thereof, medicaments being administered to said tested individual, and any combination thereof.

It is another object of the present invention to provide the sampler as defined above, wherein, in said learning phase, said data is either supervised or unsupervised data; and, said training by said control unit is performed by at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds and/or aerosols being scanned with an electromagnetic radiation in the THz range stored in said communicable and readable database in order to generate information data being indicative of at least one said virus infected individuals.

It is another object of the present invention to provide the sampler as defined above, wherein, in said detection phase, said data is either supervised or unsupervised data; and, said control unit performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds and/or aerosols being scanned with an electromagnetic radiation in the THz range stored in said communicable and readable database in order to generate information data being indicative of at least one said virus infected individuals.

It is another object of the present invention to provide the sampler as defined above, wherein, in said detection phase, said control unit detects said signature the absorption spectrum of said membrane with said VCs and/or aerosols being indicative of at least one said virus infected individuals by means of said trained machine learning model.

It is another object of the present invention to provide the sampler as defined above, wherein said system additionally comprising at least one communicable and readable database storing instructions which, when executed by the at least one data processor, result in operations comprising:

a. training a machine learning model to detect at least one parameter of said collected volatile compounds and/or aerosols being scanned with an electromagnetic radiation in the THz range of at least one tested individuals stored in said communicable and readable database in order to generate information data being indicative of said virus infected individuals; and,
b. after said step of training, real time detecting said parameter by means of said trained machine learning model.

It is another object of the present invention to provide the sampler as defined above, wherein said data is either supervised or unsupervised data; and, said control unit performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof in order to generate information data being indicative of said virus infected individuals.

It is another object of the present invention to provide the sampler as defined above, wherein said control unit additionally performs Fast Fourier Transformation in order to generate information data being indicative of said virus infected individuals.

It is another object of the present invention to provide the sampler as defined above, wherein said membrane is made of hardened extruded plastic.

It is another object of the present invention to provide the sampler as defined above, wherein said membrane is able to trap at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane (CH4), Carbon dioxide (CO2), Nitrous oxide (N2O), Ozone (O3), Chlorofluorocarbons (CFCs), Hydrofluorocarbons (includes HCFCs and HFCs), NO, NO2, viral proteins, cellular debris, debris of said virus, hydrates of said virus, hydrates of debris of said virus, hydrates of the 3D structure of said virus and a cell, aggregates of said virus, cytokines, increased level of interleukin interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the sampler as defined above, wherein said membrane is single-use, disposable membrane.

It is another object of the present invention to provide the sampler as defined above, wherein said membrane is reusable.

It is another object of the present invention to provide the sampler as defined above, wherein said volatile compounds and/or aerosols comprising at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane (CH4), Carbon dioxide (CO2), Nitrous oxide (N2O), Ozone (O3), Chlorofluorocarbons (CFCs), Hydrofluorocarbons (includes HCFCs and HFCs), NO, NO2, viral proteins, cellular debris, debris of said virus, hydrates of said virus, hydrates of debris of said virus, hydrates of the 3D structure of said virus and a cell, aggregates of said virus, cytokines, increased level of interleukin (IL)-2, interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the sampler as defined above, wherein said membrane is removable from the sampling apparatus.

It is another object of the present invention to provide the sampler as defined above, wherein said detection is completed within a period of time being less than 40 seconds.

It is another object of the present invention to provide the sampler as defined above, further comprising a spectroscopic assembly including a radiation transmitter unit being configured and operable to scan said permeable membrane holding the collected volatile compounds and/or aerosols by generating an electromagnetic radiation in the range of THz within a scanning window of about 100 GHz and a detection unit being configured and operable to detect an electromagnetic radiation emitted by said collected volatile compounds and/or aerosols.

It is another object of the present invention to provide the sampler as defined above, wherein said system additionally comprising signaling means adapted to signal the user that sufficient enough of VCs and/or aerosols have been captured in said membrane or that said detection has been completed.

It is another object of the present invention to provide the sampler as defined above, wherein said signaling means are either optical or vocal means.

It is another object of the present invention to provide a high throughput method for label-free, noncontact, noninvasive, and nondestructive detection of at least one virus infected individual from at least one tested individual, the method comprising: receiving data indicative of collected volatile compounds, VCs, and/or aerosols being scanned with electromagnetic radiation in the THz range; and processing said data for identifying a signature being indicative of said virus infected individuals.

It is another object of the present invention to provide the method as defined above, wherein said THz range is between 200 GHz to 1200 GHz.

It is another object of the present invention to provide the method as defined above, wherein said tested individual is asymptomatic and has no symptom related to said virus.

It is another object of the present invention to provide the method as defined above, wherein said system distinguishes between a healthy individual, a virus recovered individual and an infected individual.

It is another object of the present invention to provide the method as defined above, wherein detection of said virus infected individuals provides clearance to healthy individuals and/or virus recovered individuals.

It is another object of the present invention to provide the method as defined above, wherein said signature is information indicative of said virus; said information being selected from a group consisting of cell unit of said virus, viral proteins, cellular debris, debris of said virus, hydrates of said virus, hydrates of debris of said virus, hydrates of the 3D structure of said virus and a cell, aggregates of said virus, cytokines, increased level of interleukin interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the method as defined above, wherein said processing comprises performing a pattern recognition of said signature.

It is another object of the present invention to provide the method as defined above, further comprising scanning the collected volatile compounds and/or aerosols with electromagnetic radiation in the THz range within a scanning window of about 100 GHz.

It is another object of the present invention to provide the method as defined above, further comprising trapping collected volatile compounds and/or aerosols by suction, wherein said trapping is performed within a period of time being less than 40 seconds.

It is another object of the present invention to provide the method as defined above, additionally comprising the step of providing at one communicable and readable database; said database comprising absorption spectra of collected volatile compounds and/or aerosols captured in said membrane being scanned with an electromagnetic radiation in the THz range.

It is another object of the present invention to provide the method as defined above, wherein said volatile compounds and/or aerosols create spoof surface plasmon polaritons (SSPPs) captured in said membrane.

It is another object of the present invention to provide the method as defined above, wherein said virus is selected from a group selected from COV viruses family, COVID-19, Influenza, Avian influenza and any combination thereof.

It is another object of the present invention to provide the method as defined above, wherein said method is performed by a system being selected from a group consisting of a breathalyzer, any handheld device, any IOT device into which human breath is exhaled.

It is another object of the present invention to provide the method as defined above, wherein said data being processed by said control unit is at least one absorption spectrum of said membrane.

It is another object of the present invention to provide the method as defined above, wherein processing of said at least one absorption spectrum of said membrane additionally comprising pattern recognition of said at least one absorption spectrum.

It is another object of the present invention to provide the method as defined above, wherein said pattern recognition comprising at least one selected from a group consisting identification of special features of the pattern, identification of main and side peaks, the number of main and side peaks, the width of the peaks and the distance therebetween and any combination thereof.

It is another object of the present invention to provide the method as defined above, wherein said membrane is in communication with a vacuum source, a gas collection device coupled to the vacuum source, wherein the membrane is capable of capturing volatile compounds and/or aerosols.

It is another object of the present invention to provide the method as defined above, wherein said membrane is cleaned by applying at least one selected from a group consisting of positive/negative pressure or electricity to release said VCs and/or aerosols.

It is another object of the present invention to provide the method as defined above, wherein said membrane is coated with at least one material selected from a group consisting of Silicon, or Silicon Graphene, acting as a reflector, and any combination thereof.

It is another object of the present invention to provide the method as defined above, wherein said membrane is made of at least one material selected from a group consisting of Meta-Material Membrane, Semi Pressure Permeable Membrane, meta-material, PET, melamine open-cell foam-based and any combination thereof.

It is another object of the present invention to provide the method as defined above, additionally comprising an electromagnetic radiation transmitter and detector.

It is another object of the present invention to provide the method as defined above, wherein the membrane is positionable within the electromagnetic radiation emitted by the transmitter.

It is another object of the present invention to provide the method as defined above, additionally comprising at one communicable and readable database; said database comprising collected volatile compounds and/or aerosols being scanned with an electromagnetic radiation in the THz range.

It is another object of the present invention to provide the method as defined above, wherein said method has 2 modes of operation: (a) a learning phase; and, (b) a detection phase.

It is another object of the present invention to provide the method as defined above, wherein, in said learning phase, said control unit trains a machine learning model to detect at least one parameter in the absorption spectrum of said membrane with said collected volatile compounds and/or aerosols being scanned with an electromagnetic radiation in the THz range of a plurality of membrane stored in said communicable and readable database in order to generate information data being indicative of said virus infected individuals.

It is another object of the present invention to provide the method as defined above, wherein aid parameter selected from a group consisting of, trends in said database of said at least one tested individuals, eigenvector of said database of said at least one tested individuals, eigenvalues of said database of said at least one tested individuals, feature extraction step being configured to estimate the most relevant vectors defining the data using a principal component analysis, a pattern classification using a combined linear and nonlinear pattern recognition approach, known symptoms of said virus, known healthy individuals, healthy individual vital signs selected from fever, sweat, body temperature, blood pressure, pulse (heart rate), and breathing rate (respiratory rate) and any combination thereof, virus infected individual vital signs selected from fever, sweat, body temperature, blood pressure, pulse (heart rate), and breathing rate (respiratory rate) and any combination thereof, medicaments being administered to said tested individual, and any combination thereof.

It is another object of the present invention to provide the method as defined above, wherein, in said learning phase, said data is either supervised or unsupervised data; and, said training by said control unit is performed by at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds and/or aerosols being scanned with an electromagnetic radiation in the THz range stored in said communicable and readable database in order to generate information data being indicative of at least one said virus infected individuals.

It is another object of the present invention to provide the method as defined above, wherein, in said detection phase, said data is either supervised or unsupervised data; and, said control unit performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds and/or aerosols being scanned with an electromagnetic radiation in the THz range stored in said communicable and readable database in order to generate information data being indicative of at least one said virus infected individuals.

It is another object of the present invention to provide the method as defined above, wherein, in said detection phase, said control unit detects said signature the absorption spectrum of said membrane with said VCs and/or aerosols being indicative of at least one said virus infected individuals by means of said trained machine learning model.

It is another object of the present invention to provide the method as defined above, additionally comprising at least one communicable and readable database storing instructions which, when executed by the at least one data processor, result in operations comprising: training a machine learning model to detect at least one parameter of said collected volatile compounds and/or aerosols being scanned with an electromagnetic radiation in the THz range of at least one tested individuals stored in said communicable and readable database in order to generate information data being indicative of said virus infected individuals; and, after said step of training, real time detecting said parameter by means of said trained machine learning model.

It is another object of the present invention to provide the method as defined above, wherein said control unit additionally performs Fast Fourier Transformation in order to generate information data being indicative of said virus infected individuals.

It is another object of the present invention to provide the method as defined above, wherein said membrane is made of hardened extruded plastic.

It is another object of the present invention to provide the method as defined above, wherein said membrane is able to trap at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, $NO_2$, viral proteins, cellular debris, debris of said virus, hydrates of said virus, hydrates of debris of said virus, hydrates of the 3D structure of said virus and a cell, aggregates of said virus, cytokines, increased level of interleukin interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the method as defined above, wherein said membrane is single-use, disposable membrane.

It is another object of the present invention to provide the method as defined above, wherein said membrane is reusable.

It is another object of the present invention to provide the method as defined above, wherein said membrane is removable from the sampling apparatus.

It is another object of the present invention to provide the method as defined above, further comprising a spectroscopic assembly including a radiation transmitter unit being configured and operable to scan said permeable membrane holding the collected volatile compounds and/or aerosols by generating an electromagnetic radiation in the range of THz within a scanning window of about 100 GHz and a detection unit being configured and operable to detect an electromagnetic radiation emitted by said collected volatile compounds and/or aerosols.

It is another object of the present invention to provide the method as defined above, additionally comprising signaling means adapted to signal the user that sufficient enough of VCs and/or aerosols have been captured in said membrane or that said detection has been completed.

It is another object of the present invention to provide the method as defined above, wherein said signaling means are either optical or vocal means.

It is another object of the present invention to provide a high throughput method for label-free, noncontact, noninvasive, and nondestructive detection of at least one virus infected individual from at least one tested individual, the method comprising: providing at least one sampler comprising at least one metamaterial membrane absorber located at the propagation path of volatile compounds, VCs, and/or aerosols released by said at least one tested individual breath, said metamaterial membrane absorber being configured and operable for trapping the collected volatile compounds and/or aerosols; receiving data indicative of collected volatile compounds, VCs, and/or aerosols being scanned with electromagnetic radiation in the THz range;

and processing said data for identifying a signature being indicative of said virus infected individuals.

It is another object of the present invention to provide the method as defined above, wherein said THz range is between 200 GHz to 1200 GHz.

It is another object of the present invention to provide the method as defined above, wherein said tested individual is asymptomatic and has no symptom related to said virus.

It is another object of the present invention to provide the method as defined above, wherein said system distinguishes between a healthy individual, a virus recovered individual and an infected individual.

It is another object of the present invention to provide the method as defined above, wherein detection of said virus infected individuals provides clearance to healthy individuals and/or virus recovered individuals.

It is another object of the present invention to provide the method as defined above, wherein said signature is information indicative of said virus; said information being selected from a group consisting of cell unit of said virus, viral proteins, cellular debris, debris of said virus, hydrates of said virus, hydrates of debris of said virus, hydrates of the 3D structure of said virus and a cell, aggregates of said virus, cytokines, increased level of interleukin (IL)-2, interleukin IL-7, interleukin-2 receptor (IL-2R), interleukin-6 (IL-6), granulocytecolony, stimulating factor, interferon-γ, inducible protein 10, monocyte chemoattractant, protein 174, macrophage, inflammatory protein 1-α, and tumor necrosis factor-α, and any combination thereof.

It is another object of the present invention to provide the method as defined above, wherein said volatile compounds and/or aerosols create spoof surface plasmon polaritons (SSPPs) captured in said membrane.

It is another object of the present invention to provide the method as defined above, wherein said virus is selected from a group selected from COV viruses family, COVID-19, Influenza, Avian influenza and any combination thereof.

It is another object of the present invention to provide the method as defined above, wherein said sampler is at least one selected from a group consisting of a breathalyzer, a straw-like device, any handheld device, any IOT device into which human breath is exhaled.

It is another object of the present invention to provide the method as defined above, wherein said sampler comprises a proximal end and a distal end interconnected by a main longitudinal axis, along which said at least one metamaterial membrane is positioned; and into which said tested individual exhaled breath, such that the propagation path of said exhaled breath and volatile compounds and/or aerosols therewithin intersect said at least one metamaterial membrane and absorbed therewithin.

It is another object of the present invention to provide the method as defined above, wherein said sampler is airtight sealed such that said volatile compounds, VCs, and/or aerosols released by said at least one tested individuals breath are prevented from exiting said sampler.

It is another object of the present invention to provide the method as defined above, wherein said membrane is enclosed within at least one capsule; wherein said capsule is sealed.

It is another object of the present invention to provide the method as defined above, wherein said sampler is RFID tagged with each of said tested individual, such that detection of said virus infected individuals is traced back to each of said tested individual.

It is another object of the present invention to provide the method as defined above, wherein at least one of the following us being held true (a) said sampler is a disposable unit; (b) said sampler comprises at least one sealing element adapted to seal thereof.

It is another object of the present invention to provide the method as defined above, wherein said at least one metamaterial membrane is extracted from said sampler and is placed in an electromagnetic testing unit; said electromagnetic testing unit adapted to (a) scan in the THz range said metamaterial membrane absorbed with said volatile compounds and/or aerosols in said exhale breath of said tested individual; and, (b) transmit data indicative of the collected volatile compounds and/or aerosols to said control unit.

It is another object of the present invention to provide the method as defined above, wherein said sampler comprises two parts reversibly coupled to each other along a main longitudinal axis, such that (a) said at least one metamaterial membrane is positioned therebetween along said main longitudinal axis; and, (b) into said sampler said tested individual exhale breath, such that the propagation path of said exhaled breath and volatile compounds and/or aerosols therewithin intersect said at least one metamaterial membrane and absorbed therewithin.

It is another object of the present invention to provide the method as defined above, wherein said electromagnetic testing unit comprising at least one electromagnetic radiation transmitter and at least one electromagnetic radiation detector.

It is another object of the present invention to provide the method as defined above, wherein the membrane is positionable within the electromagnetic radiation emitted by the transmitter.

It is another object of the present invention to provide the method as defined above, wherein said data being processed by said control unit is at least one absorption spectrum of said membrane.

It is another object of the present invention to provide the method as defined above, wherein processing of said at least one absorption spectrum of said membrane additionally comprising pattern recognition of said at least one absorption spectrum.

It is another object of the present invention to provide the method as defined above, wherein said pattern recognition comprising at least one selected from a group consisting identification of special features of the pattern, identification of main and side peaks, the number of main and side peaks, the width of the peaks and the distance therebetween and any combination thereof.

It is another object of the present invention to provide the method as defined above, wherein said membrane is in communication with a vacuum source, a gas collection device coupled to the vacuum source, wherein the membrane is capable of capturing volatile compounds and/or aerosols.

It is another object of the present invention to provide the method as defined above, wherein said membrane is cleaned by applying at least one selected from a group consisting of positive/negative pressure or electricity to release said VCs and/or aerosols.

It is another object of the present invention to provide the method as defined above, wherein said membrane is coated with at least one material selected from a group consisting of Silicon, or Silicon Graphene, acting as a reflector, and any combination thereof.

It is another object of the present invention to provide the method as defined above, wherein said membrane is made of at least one material selected from a group consisting of Meta-Material Membrane, Semi Pressure Permeable Membrane, meta-material, PET, melamine open-cell foam-based and any combination thereof.

It is another object of the present invention to provide the method as defined above, wherein said control unit is configured and operable for performing a pattern recognition of said signature.

It is another object of the present invention to provide the method as defined above, wherein said system additionally comprising at one communicable and readable database; said database comprising collected volatile compounds and/or aerosols being scanned with an electromagnetic radiation in the THz range.

It is another object of the present invention to provide the method as defined above, wherein said data is either supervised or unsupervised data; and, said control unit performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof in order to generate information data being indicative of said virus infected individuals.

It is another object of the present invention to provide the method as defined above, wherein said control unit additionally performs Fast Fourier Transformation in order to generate information data being indicative of said virus infected individuals.

It is another object of the present invention to provide the method as defined above, wherein said membrane is made of hardened extruded plastic.

It is another object of the present invention to provide the method as defined above, wherein said membrane is able to trap at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, $NO_2$, viral proteins, cellular debris, debris of said virus, hydrates of said virus, hydrates of debris of said virus, hydrates of the 3D structure of said virus and a cell, aggregates of said virus, cytokines, increased level of interleukin interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the method as defined above, wherein said membrane is single-use, disposable membrane.

It is another object of the present invention to provide the method as defined above, wherein said membrane is reusable.

It is another object of the present invention to provide the method as defined above, wherein said volatile compounds and/or aerosols comprising at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, $NO_2$, viral proteins, cellular debris, debris of said virus, hydrates of said virus, hydrates of debris of said virus, hydrates of the 3D structure of said virus and a cell, aggregates of said virus, cytokines, increased level of interleukin (IL)-2, interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the method as defined above, wherein said membrane is removable from the sampling apparatus.

It is another object of the present invention to provide the method as defined above, wherein said detection is completed within a period of time being less than 40 seconds.

It is another object of the present invention to provide the method as defined above, further comprising a spectroscopic assembly including a radiation transmitter unit being configured and operable to scan said permeable membrane holding the collected volatile compounds and/or aerosols by generating an electromagnetic radiation in the range of THz within a scanning window of about 100 GHz and a detection unit being configured and operable to detect an electromagnetic radiation emitted by said collected volatile compounds and/or aerosols.

It is another object of the present invention to provide the method as defined above, wherein said system additionally comprising signaling means adapted to signal the user that sufficient enough of VCs and/or aerosols have been captured in said membrane or that said detection has been completed.

It is another object of the present invention to provide the method as defined above, wherein said signaling means are either optical or vocal means.

It is another object of the present invention to provide the method as defined above, wherein said processing comprises performing a pattern recognition of said signature.

It is another object of the present invention to provide the method as defined above, further comprising scanning the collected volatile compounds and/or aerosols with electromagnetic radiation in the THz range within a scanning window of about 100 GHz.

It is another object of the present invention to provide the method as defined above, further comprising trapping collected volatile compounds and/or aerosols by suction, wherein said trapping is performed within a period of time being less than 40 seconds.

It is another object of the present invention to provide the method as defined above, additionally comprising the step of providing at one communicable and readable database; said database comprising absorption spectra of collected volatile compounds and/or aerosols captured in said membrane being scanned with an electromagnetic radiation in the THz range.

It is another object of the present invention to provide the method as defined above, wherein said volatile compounds and/or aerosols create spoof surface plasmon polaritons (SSPPs) captured in said membrane.

T It is another object of the present invention to provide the method as defined above, wherein said virus is selected from a group selected from COV viruses family, COVID-19, Influenza, Avian influenza and any combination thereof.

It is another object of the present invention to provide the method as defined above, wherein said method is performed by a system being selected from a group consisting of a breathalyzer, any handheld device, any IOT device into which human breath is exhaled.

It is another object of the present invention to provide the method as defined above, wherein said data being processed by said control unit is at least one absorption spectrum of said membrane.

It is another object of the present invention to provide the method as defined above, wherein processing of said at least one absorption spectrum of said membrane additionally comprising pattern recognition of said at least one absorption spectrum.

It is another object of the present invention to provide the method as defined above, wherein said pattern recognition comprising at least one selected from a group consisting identification of special features of the pattern, identification of main and side peaks, the number of main and side peaks, the width of the peaks and the distance therebetween and any combination thereof.

It is another object of the present invention to provide the method as defined above, wherein said membrane is in communication with a vacuum source, a gas collection device coupled to the vacuum source, wherein the membrane is capable of capturing volatile compounds and/or aerosols.

It is another object of the present invention to provide the method as defined above, wherein said membrane is cleaned by applying at least one selected from a group consisting of positive/negative pressure or electricity to release said VCs and/or aerosols.

It is another object of the present invention to provide the method as defined above, wherein said membrane is coated with at least one material selected from a group consisting of Silicon, or Silicon Graphene, acting as a reflector, and any combination thereof.

It is another object of the present invention to provide the method as defined above, wherein said membrane is made of at least one material selected from a group consisting of Meta-Material Membrane, Semi Pressure Permeable Membrane, meta-material, PET, melamine open-cell foam-based and any combination thereof.

It is another object of the present invention to provide the method as defined above, additionally comprising an electromagnetic radiation transmitter and detector.

It is another object of the present invention to provide the method as defined above, wherein the membrane is positionable within the electromagnetic radiation emitted by the transmitter.

It is another object of the present invention to provide the method as defined above, additionally comprising at one communicable and readable database; said database comprising collected volatile compounds and/or aerosols being scanned with an electromagnetic radiation in the THz range.

It is another object of the present invention to provide the method as defined above, wherein said method has 2 modes of operation: (a) a learning phase; and, (b) a detection phase.

It is another object of the present invention to provide the method as defined above, wherein, in said learning phase, said control unit trains a machine learning model to detect at least one parameter in the absorption spectrum of said membrane with said collected volatile compounds and/or aerosols being scanned with an electromagnetic radiation in the THz range of a plurality of membrane stored in said communicable and readable database in order to generate information data being indicative of said virus infected individuals.

It is another object of the present invention to provide the method as defined above, wherein aid parameter selected from a group consisting of, trends in said database of said at least one tested individuals, eigenvector of said database of said at least one tested individuals, eigenvalues of said database of said at least one tested individuals, feature extraction step being configured to estimate the most relevant vectors defining the data using a principal component analysis, a pattern classification using a combined linear and nonlinear pattern recognition approach, known symptoms of said virus, known healthy individuals, healthy individual vital signs selected from fever, sweat, body temperature, blood pressure, pulse (heart rate), and breathing rate (respiratory rate) and any combination thereof, virus infected individual vital signs selected from fever, sweat, body temperature, blood pressure, pulse (heart rate), and breathing rate (respiratory rate) and any combination thereof, medicaments being administered to said tested individual, and any combination thereof.

It is another object of the present invention to provide the method as defined above, wherein, in said learning phase, said data is either supervised or unsupervised data; and, said training by said control unit is performed by at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds and/or aerosols being scanned with an electromagnetic radiation in the THz range stored in said communicable and readable database in order to generate information data being indicative of at least one said virus infected individuals.

It is another object of the present invention to provide the method as defined above, wherein, in said detection phase, said data is either supervised or unsupervised data; and, said control unit performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected volatile compounds and/or aerosols being scanned with an electromagnetic radiation in the THz range stored in said communicable and readable database in order to generate information data being indicative of at least one said virus infected individuals.

It is another object of the present invention to provide the method as defined above, wherein, in said detection phase, said control unit detects said signature the absorption spectrum of said membrane with said VCs and/or aerosols being indicative of at least one said virus infected individuals by means of said trained machine learning model.

It is another object of the present invention to provide the method as defined above, additionally comprising at least one communicable and readable database storing instructions which, when executed by the at least one data processor, result in operations comprising:

a. training a machine learning model to detect at least one parameter of said collected volatile compounds and/or aerosols being scanned with an electromagnetic radiation in the THz range of at least one tested individuals stored in said communicable and readable database in order to generate information data being indicative of said virus infected individuals; and, b. after said step of training, real time detecting said parameter by means of said trained machine learning model.

It is another object of the present invention to provide the method as defined above, wherein said control unit additionally performs Fast Fourier Transformation in order to generate information data being indicative of said virus infected individuals.

It is another object of the present invention to provide the method as defined above, wherein said membrane is made of hardened extruded plastic.

It is another object of the present invention to provide the method as defined above, wherein said membrane is able to trap at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane (CH4), Carbon dioxide (CO2), Nitrous oxide (N2O), Ozone (O3), Chlorofluorocarbons (CFCs), Hydrofluorocarbons (includes HCFCs and HFCs), NO, NO2, viral proteins, cellular debris, debris of said virus, hydrates of said virus, hydrates of debris of said virus, hydrates of the 3D structure of said virus and a cell, aggregates of said virus, cytokines, increased level of interleukin interleukin IL-7, interleukin-2 receptor (IL-2R), interleukin-6 (IL-6), granulocytecolony, stimulating factor, interferon-γ, inducible protein 10, monocyte chemoattractant, protein 1, macrophage, inflammatory protein 1-α, and tumor necrosis factor-α, and any combination thereof.

It is another object of the present invention to provide the method as defined above, wherein said membrane is single-use, disposable membrane.

It is another object of the present invention to provide the method as defined above, wherein said membrane is reusable.

It is another object of the present invention to provide the method as defined above, wherein said membrane is removable from the sampling apparatus.

It is another object of the present invention to provide the method as defined above, further comprising a spectroscopic assembly including a radiation transmitter unit being configured and operable to scan said permeable membrane holding the collected volatile compounds and/or aerosols by generating an electromagnetic radiation in the range of THz within a scanning window of about 100 GHz and a detection unit being configured and operable to detect an electromagnetic radiation emitted by said collected volatile compounds and/or aerosols.

It is another object of the present invention to provide the method as defined above, additionally comprising signaling means adapted to signal the user that sufficient enough of VCs and/or aerosols have been captured in said membrane or that said detection has been completed.

It is another object of the present invention to provide the method as defined above, wherein said signaling means are either optical or vocal means.

It is another object of the present invention to provide the system as defined above, utilized for homeland security applications.

It is another object of the present invention to provide the system as defined above, utilized in public places selected from airports, schools, public clinic, convention centers, parks, kindergartens, stadiums and any combination thereof.

It is another object of the present invention to provide the system as defined above, utilized for homeland security applications.

It is another object of the present invention to provide the system as defined above, utilized in public places selected from airports, schools, public clinic, convention centers, parks, kindergartens, stadiums and any combination thereof.

It is another object of the present invention to provide the sampler as defined above, utilized in a system for homeland security applications.

It is another object of the present invention to provide the sampler as defined above, utilized in a system for public places selected from airports, schools, public clinic, convention centers, parks, kindergartens, stadiums and any combination thereof.

It is another object of the present invention to provide the method as defined above, utilized for homeland security applications.

It is another object of the present invention to provide the method as defined above, utilized in public places selected from airports, schools, public clinic, convention centers, parks, kindergartens, stadiums and any combination thereof.

It is another object of the present invention to provide the method as defined above, utilized for homeland security applications.

It is another object of the present invention to provide the method as defined above, utilized in public places selected from airports, schools, public clinic, convention centers, parks, kindergartens, stadiums and any combination thereof.

It is another object of the present invention to provide the method or system or sampler as defined above, additionally comprising at least one filter disposed on said membrane.

It is another object of the present invention to provide the method or system or sampler as defined above, wherein said filter is adapted to affect the absorption signal detected in the absorption spectrum when said VCs and/or aerosols are absorbed on said membrane.

It is another object of the present invention to provide the method or system or sampler as defined above, wherein said filter is at least one selected from a group consisting of ring resonator, directional antenna, antenna, band-stop filter, notch filter and any combination thereof.

According to another embodiment of the present invention the THz spectrum collected from scanning the membraned with the tested subject's exhaled breath is calibrated or normalized with at least one parameter. The parameter can be any (or all) of the following PCR Ct, temperature at the location where the sample had been taken, humidity at the location where the sample had been taken, barometric pressure at the location where the sample had been taken, the relative position of one THz scanner to another one, the location at which said sample is taken, a THz scan of a predefined gold standard and any combination thereof.

The predefined gold standard could be a non-used membrane, a non Covid-19 infected subject (i.e., a healthy subject), a Covid-19 infected subject (i.e., a Covid-19 sick subject).

Such calibration alleviates the identification of Covid-19 infected subjects.

In the claims, the word 'comprising' does not exclude the presence of other elements or steps then those listed in a claim. Furthermore, the terms "a" or "an," as used herein, are defined as one as or more than one. Also, the use of introductory phrases such as "at least one" and "one or more" in the claims should not be construed to imply that the introduction of another claim element by the indefinite articles "a" or "an" limits any particular claim containing such an introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween. As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements. Various embodiments and aspects of the present invention as delineated hereinabove and as claimed in the claims section below find experimental support in the following examples.

Example 1

The following provides a non-limiting example as for the ability of the system and the sampler as described above to provide fast clearance detection for Coronavirus utilizing the proprietary system and the sampler and a proprietary breath testing tube (integrating a proprietary membrane) to distinguish between healthy (Covid-19 free) and infected subjects (positive to Covid-19, both symptomatic and asymptomatic).

First a feasibility test was performed to demonstrate a preliminary proof of concept. Next, clinical trials were (and still are) performed.

All data was analyzed using a proprietary analyzing protocol and algorithm which, inert alia, includes an unsupervised learning algorithm that seeks for undetected patterns in a data set with no pre-existing labels and with a minimum of human supervision.

Feasibility and Clinical Testing 245 subjects were tested, out of which 100 patients were tested positive and 145 patients tested negative, to Covid-19. This observation was validated using RT-PCR. The table below summarizes the existence of any related symptoms associated with Covid-19 the different groups, (i.e., healthy versus infected).

TABLE 2

Summary of recorded symptoms for the patients in the study

|          | Symptomatic | Asymptomatic | Symptoms Not reported | Total |
|----------|-------------|--------------|-----------------------|-------|
| Positive | 37          | 18           | 44                    | 100   |
| Negative | 37          | 4            | 105                   | 145   |

Preliminary Results and First In Vitro Feasibility Testing

First, an in vitro feasibility test was conducted using chicken IBV, (Infectious Bronchitis Virus, an avian corona virus), strain, IBVR233A.

Figure 8A:
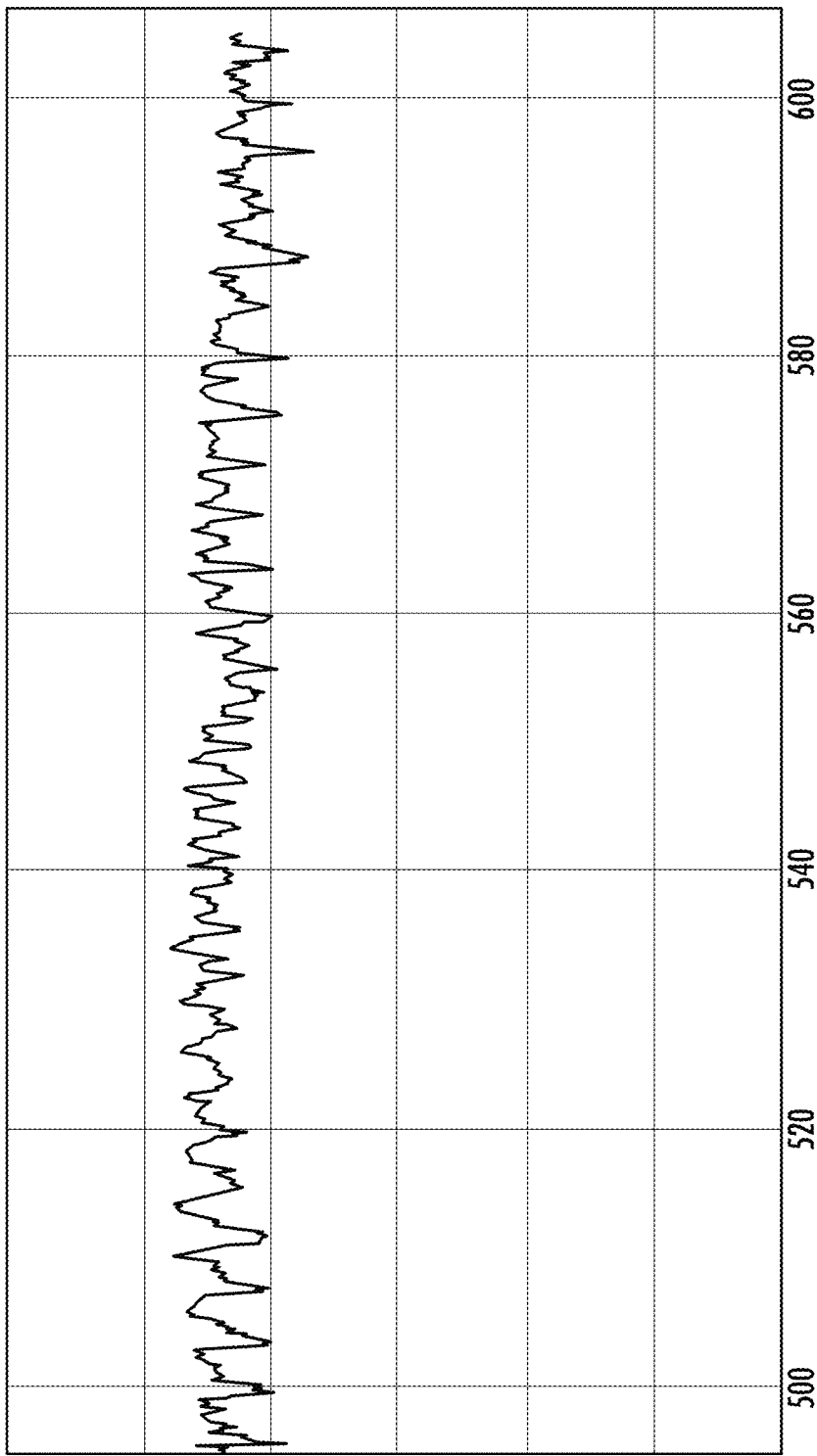
FIG. 8a illustrates the spectrum analysis received from the THz scan of the volatile compounds and/or aerosols captured in the membrane.
Figure 8B:
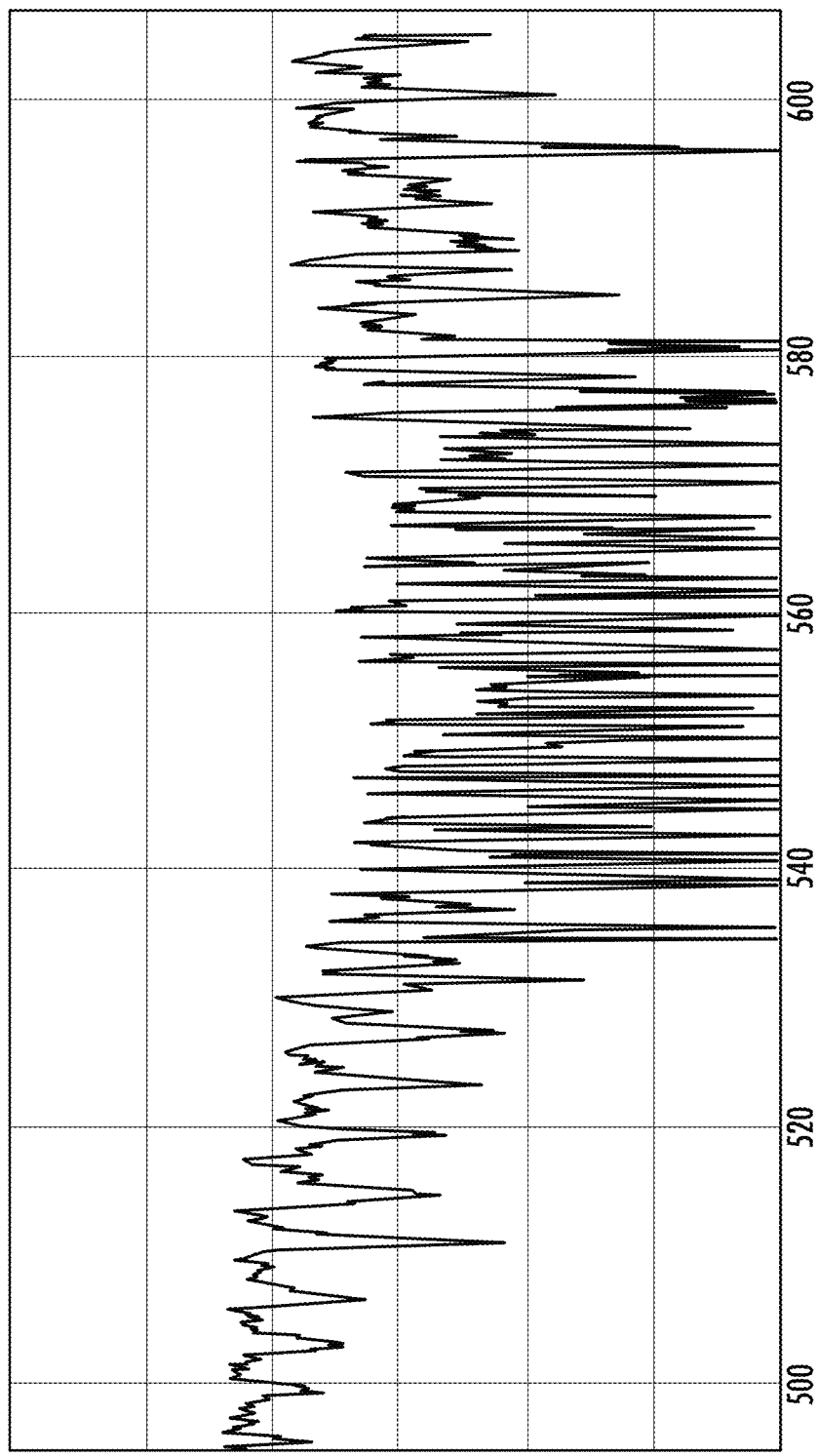
FIG. 8b illustrates the spectrum analysis received from the THz scan of the volatile compounds and/or aerosols captured in the membrane.

Briefly, IBV233A was diluted is double distilled water (DDW) as per manufacturer guidelines, (1 capsule dissolved in 30 mL DDW results in ~10^4 virions per mL, (i.e., stock solution, marked as triangles in FIGS. 8a-8b).

To mimic the clinical protocol, which utilizes a breath testing tube integrated with a proprietary membrane, a home inhalation device, (Life #7290108452877), was used. The diluted solution was transferred to the inhalator cup, each membrane was passed through the steams generated five times. Each concentration was repeated 5 times, and each membrane was scanned five times from 400 GHZ to 1200THz.

The stock solution was further diluted 1:10 in DDW to produce the following concentrations: ×1000, (~10^3 virions/mL), ×100, (~10^2 virions/mL), and ×10, (~10 virions/mL). Membrane (denoted in the Fig. as 'Ref') alone and vehicle control were tested as well, Ref (i.e., the membrane) and Ref soaked in water samples, all illustrated in FIGS. 8a-c.

Figure 8C:
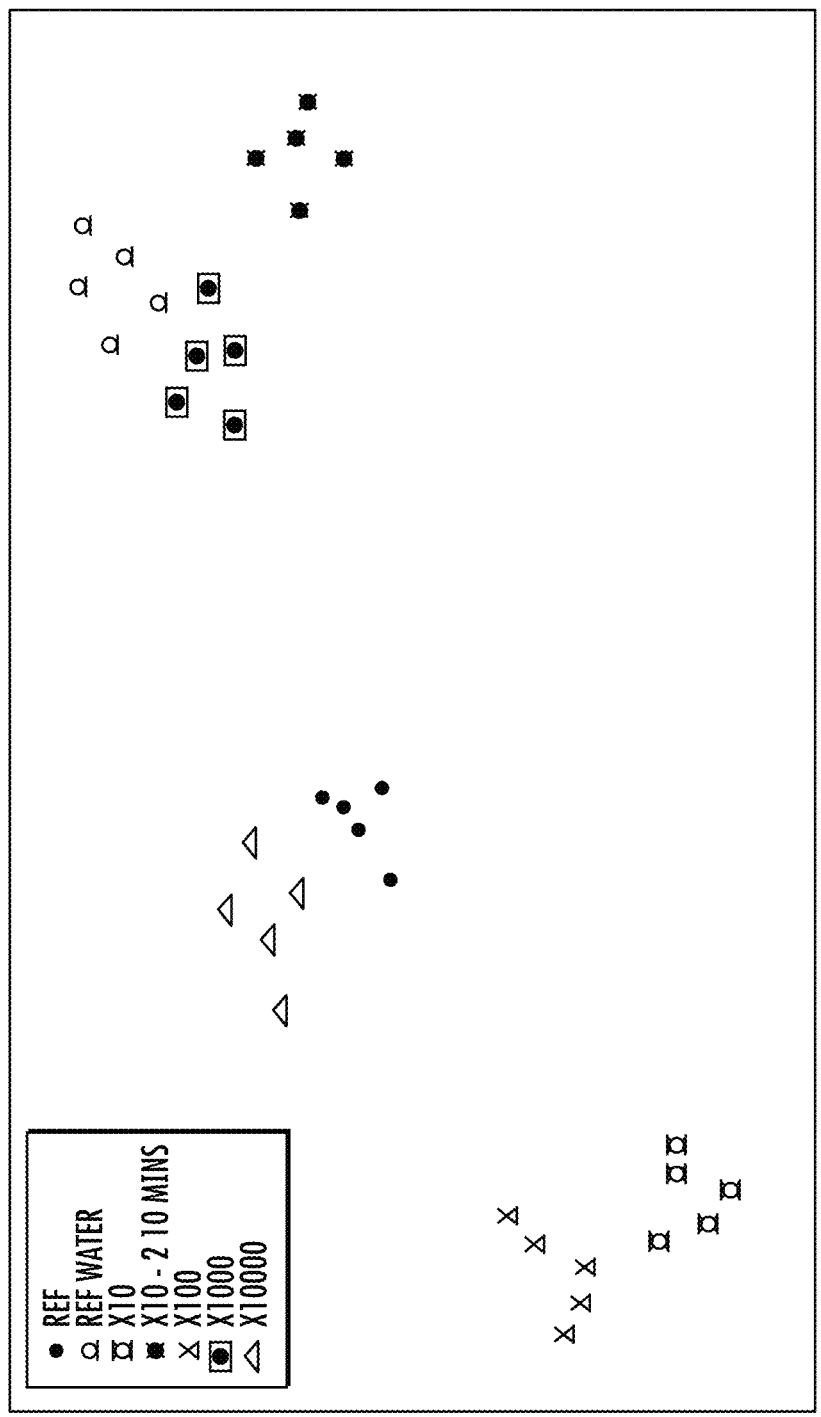
FIG. 8c illustrates the spectrum analysis received from the THz scan of the volatile compounds and/or aerosols captured in the membrane.

FIGS. 8a-c illustrate clustering analysis of the Avian Corona Virus results. As clearly illustrated in FIGS. 8a-b, the clustering yielded distinct groups, suggesting that each being characterized by different spectral signatures.

Second In Vitro Feasibility Test Using Different Avian Corona Strains, Namely (IBV) H120.

Further to the first feasibility test extended the in-vitro protocol to further test system's ability to differentiate between different avian corona strains. For this matter recombinant infectious bronchitis virus (IBV) H120, was examined as well. H120 was diluted in 30 mL of DDW as per manufacturer's guidelines.

The experimental protocol was the same as for IBV 233A, (described in details in section 1, above).

Figure 8D:
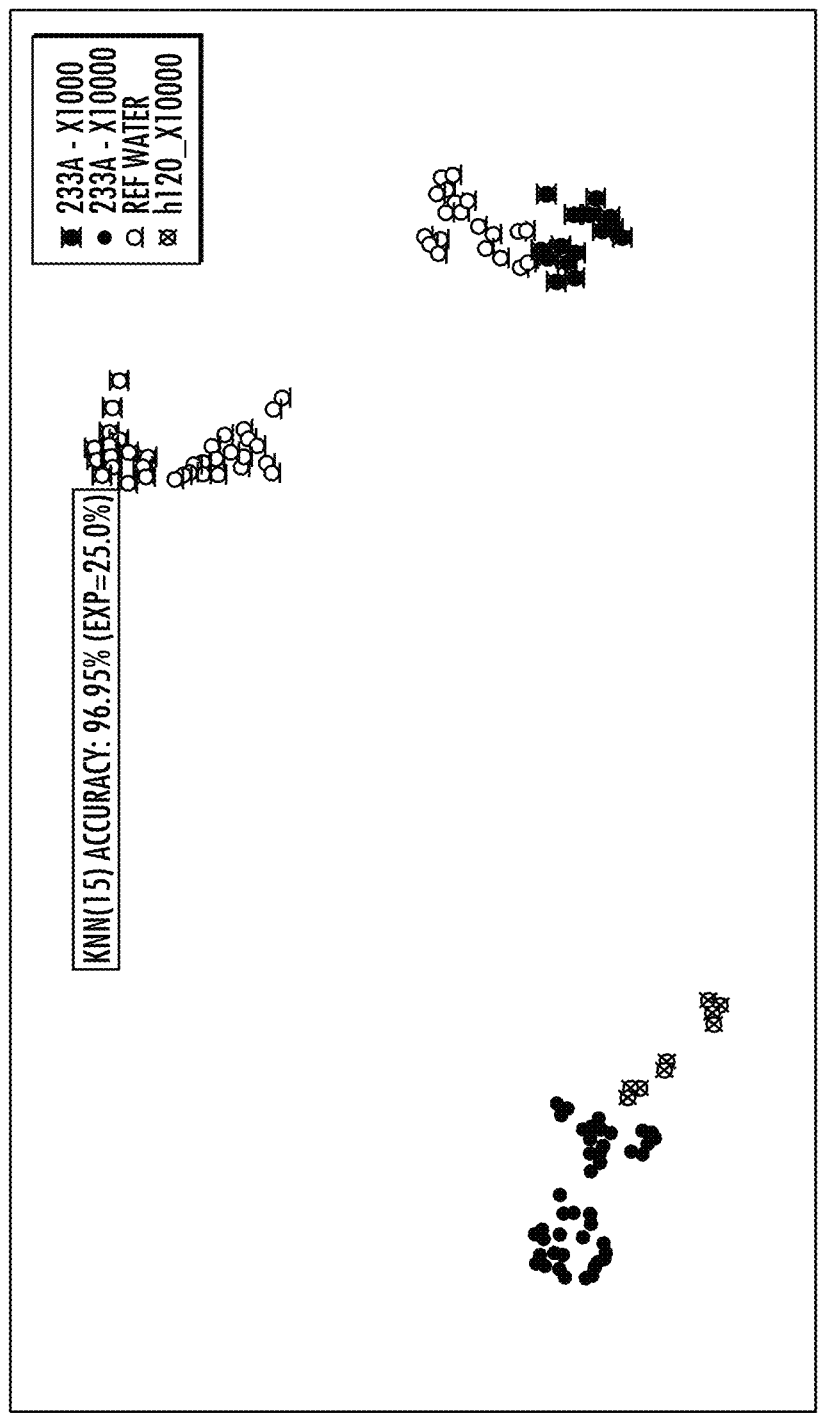
FIG. 8d illustrates the spectrum analysis received from the THz scan of the volatile compounds and/or aerosols captured in the membrane.

As illustrated in FIG. 8d, our clustering analysis for several avian corona strains resulted in a definite and obvious separation for each tested group. As mentioned, this distinct separation is indicative of a specific spectral pattern which characterizes each group.

Clinical Phase 245 subjects were included in this study. 68% of the subjects were male and the rest 32% were female.

The mean age is 50. Each subject was given the sampler of the present invention and was asked to exhale 3 long breaths (1.5 L of air). Next, the membrane (integrated within said sampler) was transferred into a sealed capsule scanned and analyzed by the system of the present invention and proprietary analyzing protocol (algorithm).

The clinical trial was approved by the Helsinki committee, and is currently ongoing in a few medical institutes (The Sheba Medical Institute, Ashkelon military Corona sanitarium, Maccabi Clinics sanitarium and others).

Reference is now made to FIGS. 8a-8b illustrating typical exhale spectrum of tested subjects. These spectra will be analyzed as described hereinbelow.

Figure 8E:
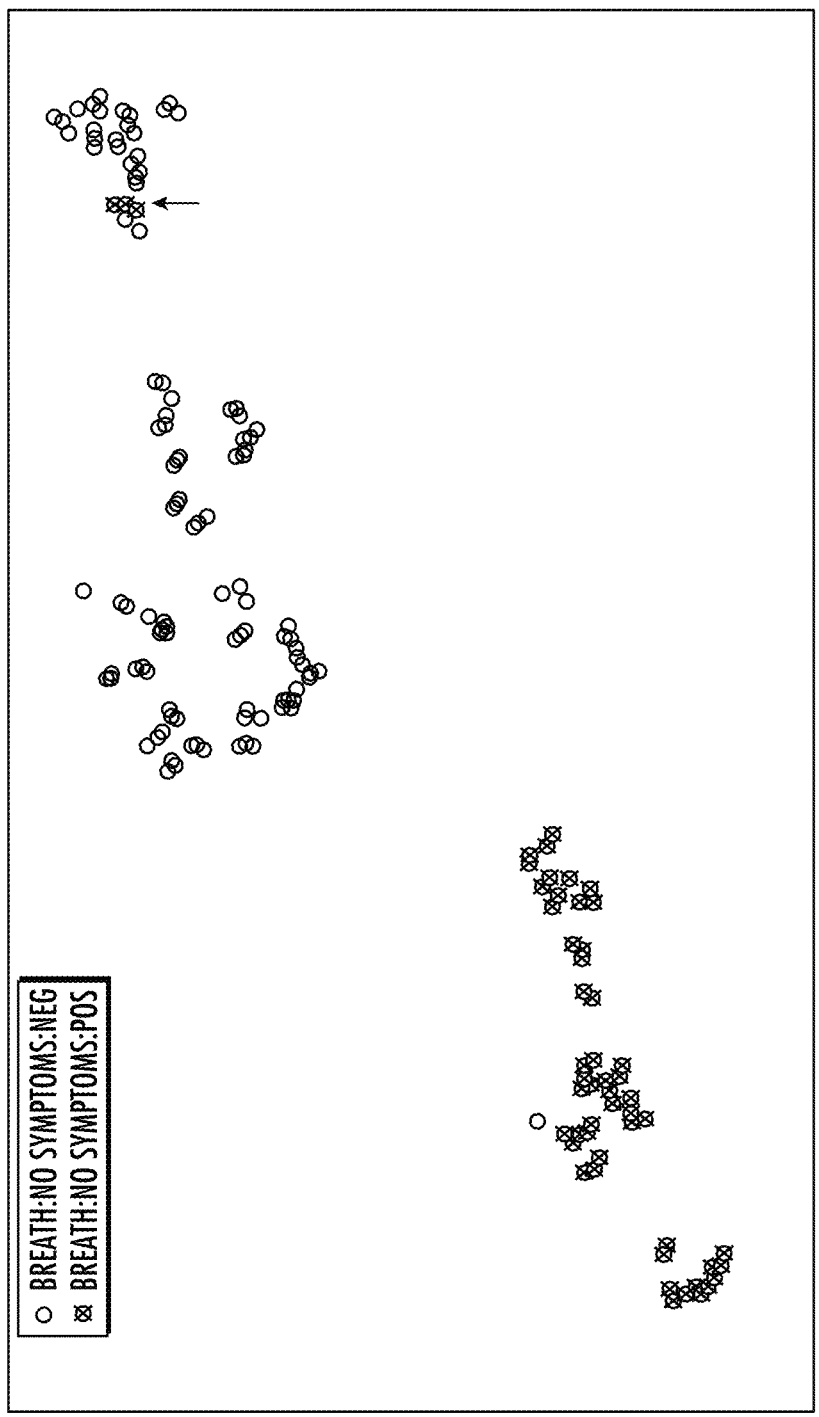
FIG. 8e illustrates the spectrum analysis received from the THz scan of the volatile compounds and/or aerosols captured in the membrane.

Results (a) Distinguishable Clustering of Covid-19 Free Subjects Out of Covid-19 Infected Subjects The first sample included healthy) Covid-19 free) subjects with no symptoms and confirmed (infected) Covid-19 patients from the Isolation Unit at The Sheba Medical Institute. As depicted in FIG. 8e, our clustering analysis resulted in a definite two group separation for Healthy versus Infected subjects, (circles refers to the Covid-19 free individuals, and circles with 'x' therewithin refers to the covid-19 infected individuals).

While the spectral signature of two subjects that were conventionally classified as covid-19 infected subjects (by means of RT-PCR); both were classified, according to the present embodiment, as healthy (covid-19-free) and were identified and entrained in the healthy group, (marked with arrow).

Importantly a second RT-PCR analysis of those subjects confirmed both to be healthy (covid-19-free); i.e., negative, (three more similar cases were attested to, illustrated in FIG. 8a). The latter suggest that the technology utilized according to the instant embodiment, with its proprietary identification technique, can identify a spectral signature that is encompass the ability to distinguish between healthy (namely, Covid-19 free) and infected subjects.

Figure 8F:
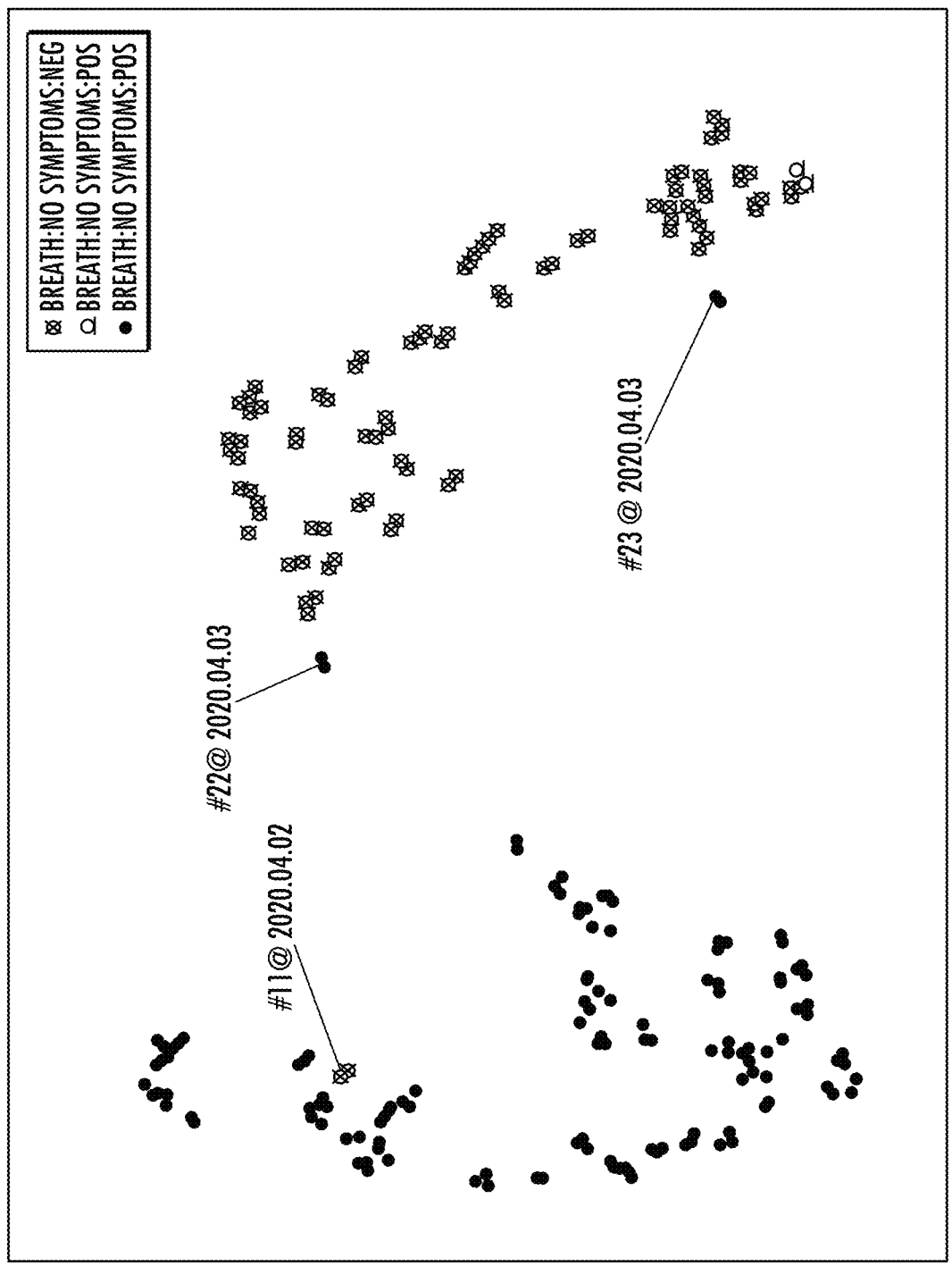
FIG. 8f illustrates the spectrum analysis received from the THz scan of the volatile compounds and/or aerosols captured in the membrane.

FIG. 8f illustrates healthy (Covid-19 free) subjects showing no symptoms, Covid-19 recovered subjects showing no symptoms and Covid19 infected subjects showing symptoms.

Note: Two different subjects were originally diagnosed as infected (#22 and 23, denoted in the fig.); however, as above, our proprietary technology classified them as healthy (Covid-19 free) in the healthy group (denoted in the Fig. as circles with 'x' therewithin). One subject was originally classified as healthy (#11, denoted in the fig.) by RT-PCR (first test), but was found by our technology as Covid-19 infected subject and is illustrated in the "infected group", (denoted in the Fig. as circles).

A second RT-PCR test performed to all 3 subjects (#11, 22 and 23) conformed our findings. Namely, that subjects #22 and 23 are Covid-19 free and #11 Covid-19 infected.

Distinguishable Clustering of Covid-19 Infected Subjects Vs. Other Virus Infected Subjects Distinguishable Clustering of Covid-19 Infected Subjects Vs. H120 Infected Subjects It is known that avian corona virus H120 shares 30% sequence homology with SARS-Cov-2.

Figure 8G:
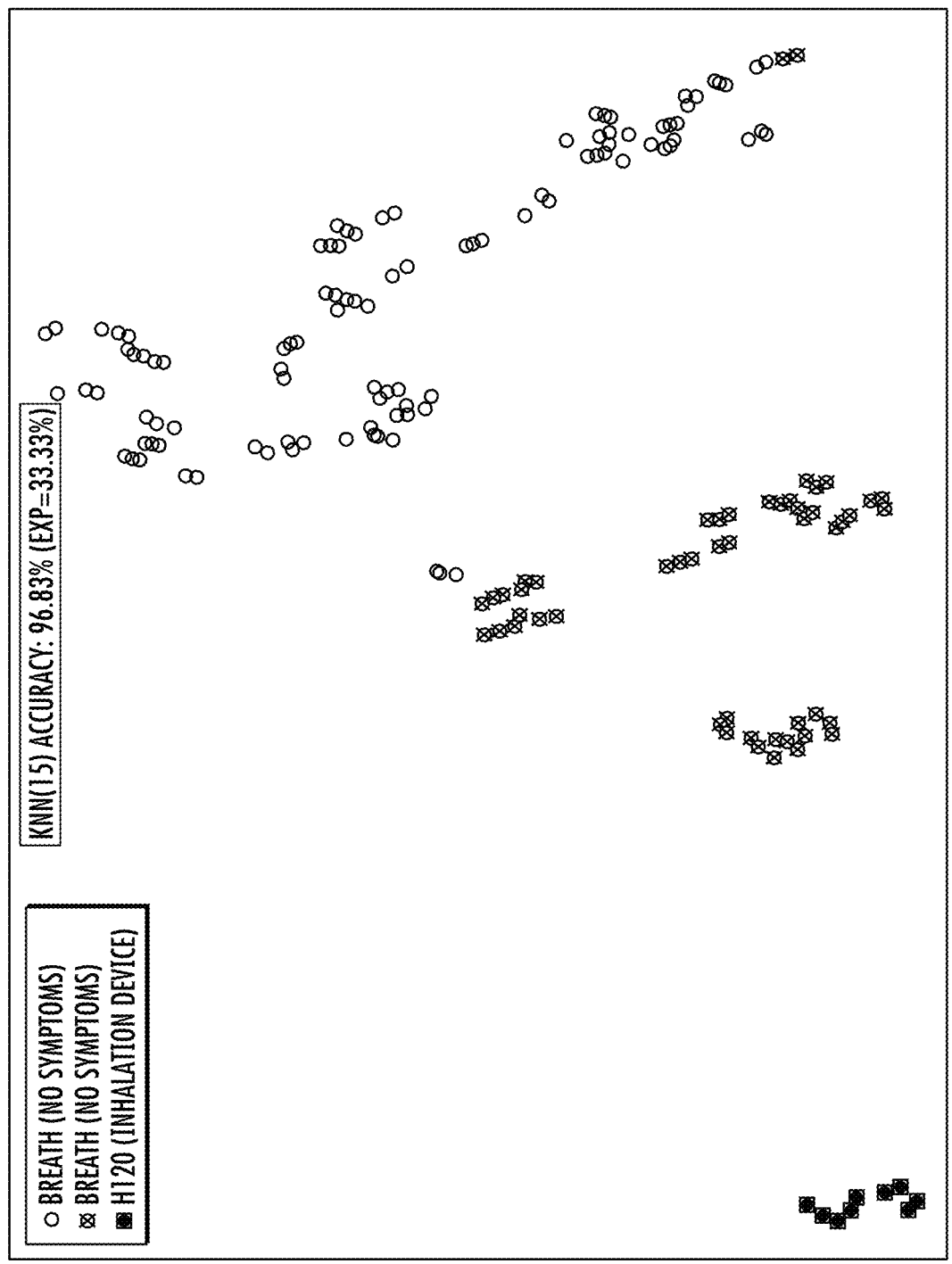
FIG. 8g illustrates the spectrum analysis received from the THz scan of the volatile compounds and/or aerosols captured in the membrane.

Thus, the clustering analysis was extended to validate its capabilities in differentiating H120 from Covid-19 infected subjects as depicted in FIG. 8g. Distinguish between three different groups was accomplished: Healthy versus infected subject clustering compared with avian virus, H120.

Cancellation of the Testing Time Effect on the Results

Annulment of any effect that may occur in-light of different time in which the testing was performed.

Figure 8H:
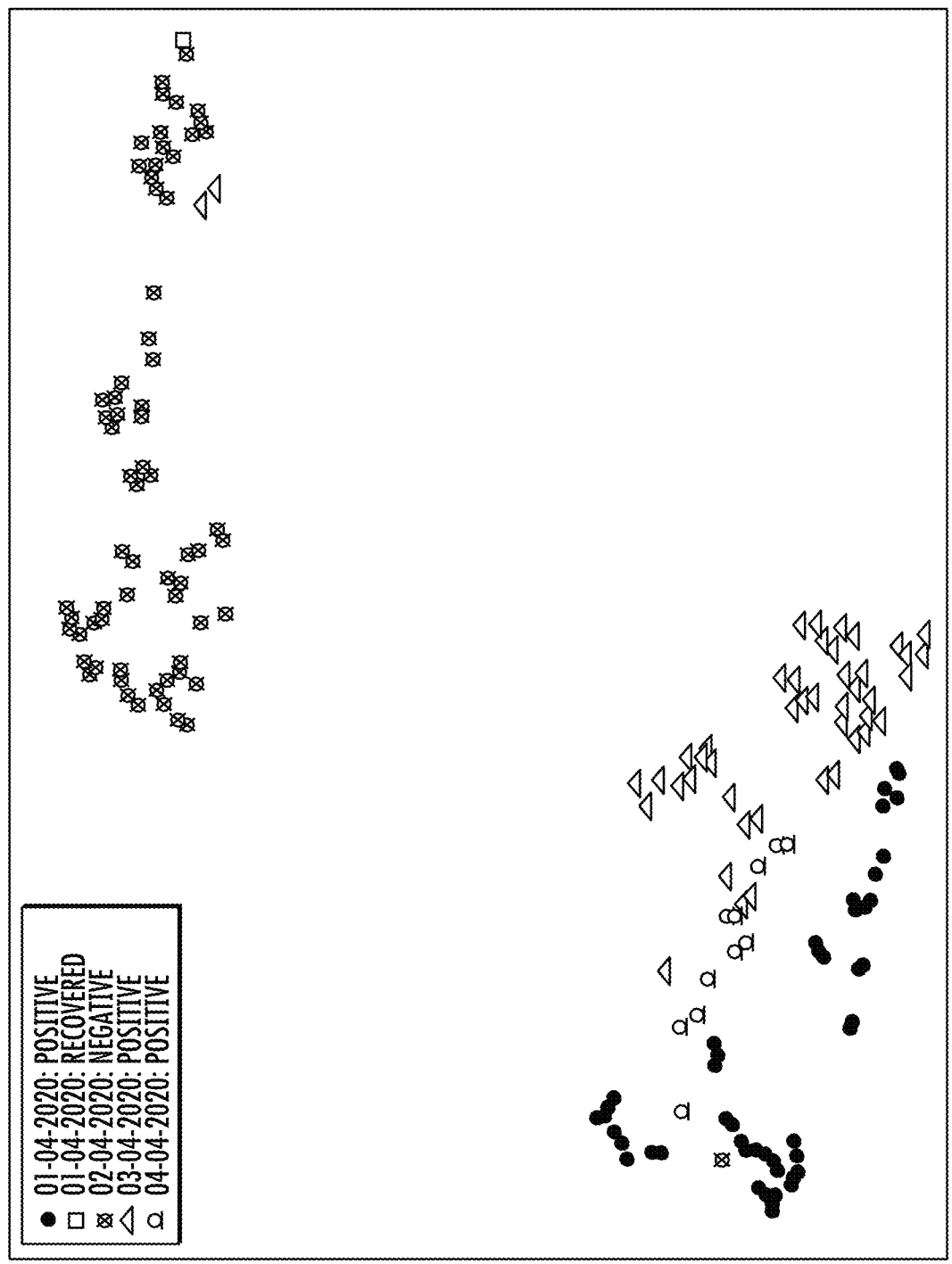
FIG. 8h illustrates the spectrum analysis received from the THz scan of the volatile compounds and/or aerosols captured in the membrane.

FIG. 8h illustrates clustering analysis of healthy (Covid-19 free) subjects and infected subjects, taken at different time frames at different locations. As is clearly shown in the figure, two distinct groups are identified by a proprietary analysis: denoted in the Figure as circles with 'x' therewithin, top of the Figure) which resembles healthy subjects, and Mixed shapes, (bottom of the Figure), which resembles covid-19 infected subjects, as taken at different time frames.

Figure 8I:
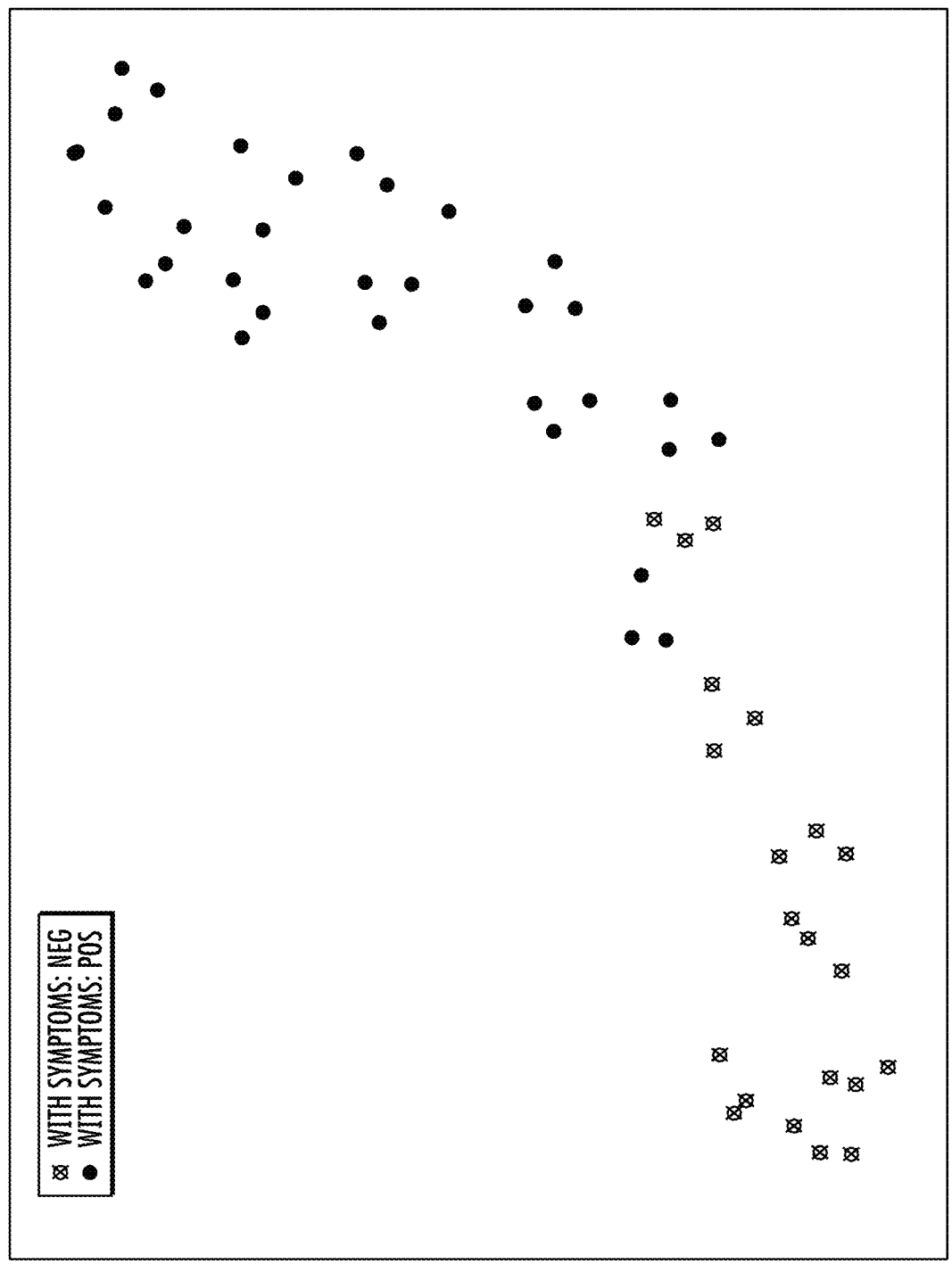
FIG. 8i illustrates the spectrum analysis received from the THz scan of the volatile compounds and/or aerosols captured in the membrane.

Clustering of Healthy (Covid-19 Free) and Infected Substance Each with Denoted Symptoms Different clustering among different subjects (healthy and infected) with symptoms was evaluated. Samples from patients infected with covid-19, (denoted as circles in the Figure) and healthy subjects with respiratory symptoms, (denoted as 'x' in the Figure) were examined. Clustering resulted in two distinct groups. The differences are illustrated in FIG. 8i.

Clearance of Healthy (Covid-19 Free) Subjects

The main objective of this clinical trial is clearance healthy (Covid-19) subjects. Such clearance could give rise to a new financial driven decision making to each subject being suspected of Covid-19.

Figure 8J:
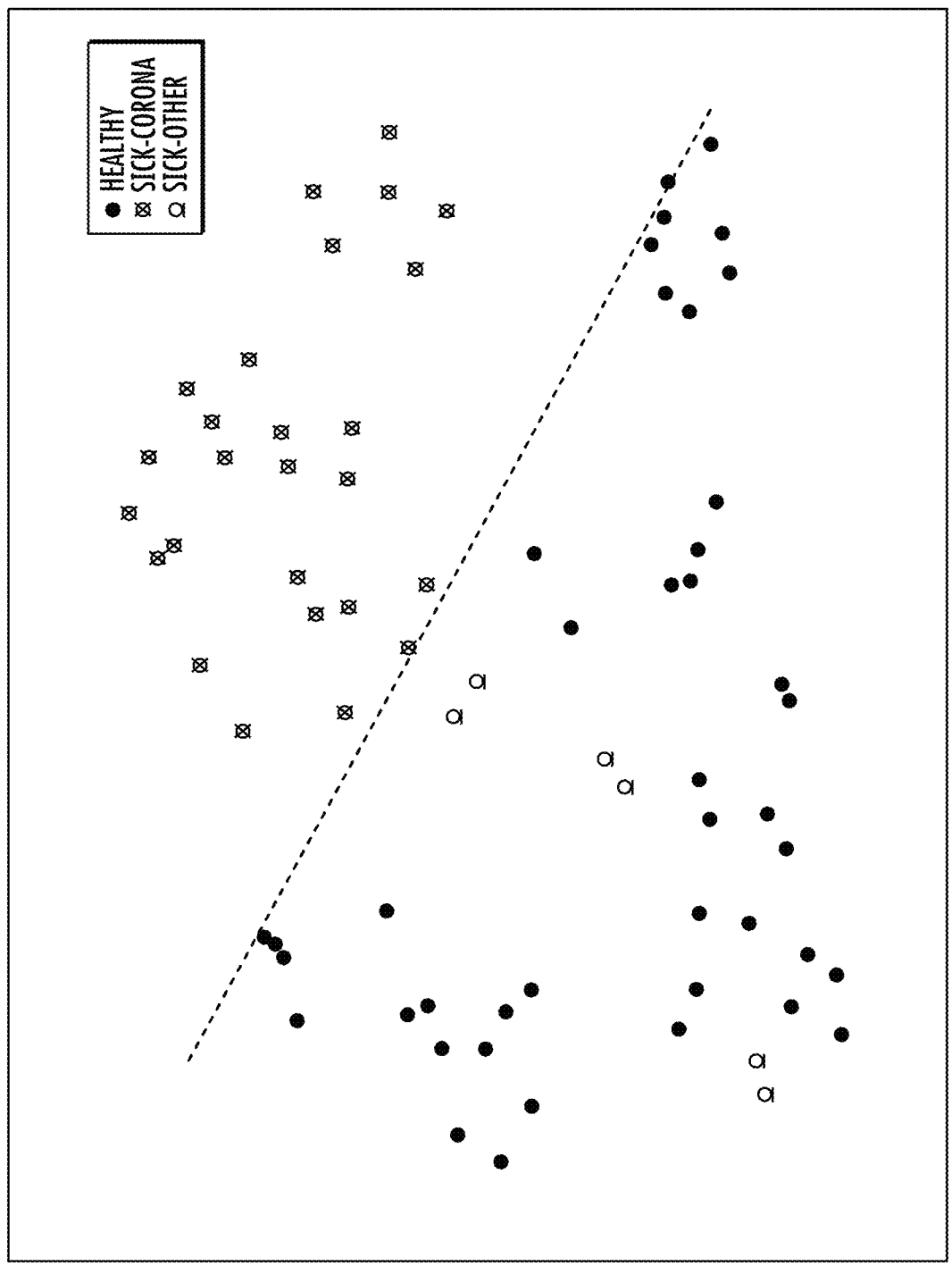
FIG. 8j illustrates the spectrum analysis received from the THz scan of the volatile compounds and/or aerosols captured in the membrane.

To test our proprietary technology's capabilities in differentiating healthy subjects, we extended our sample collection as follows, breath samples were collected from patients admitted to the ER for infection categorized other than covid-19, (denoted as circles in the above illustration, FIG. 8i) and infected ones. Notably the latter group fall into the "healthy group", (left of the border), using our clustering analysis, thus distinguishing health (Covid-19 free) subjects from infected ones. The results of this analysis are illustrated in FIG. 8j below. Thus, FIG. 8j illustrates classification of ER admissions versus know healthy patients and known Covid-19 patients.

Figure 8K:
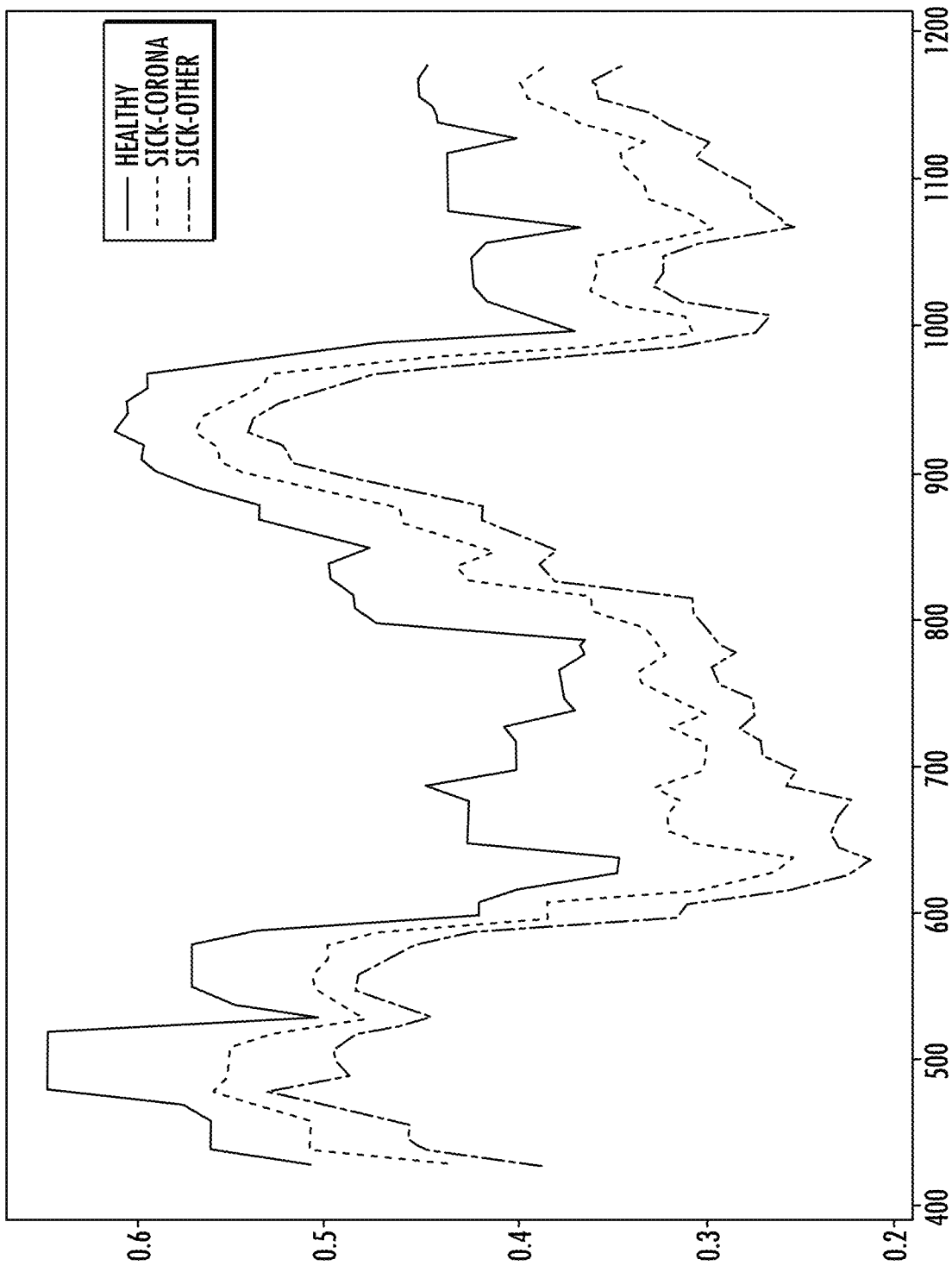
FIG. 8k illustrates the spectrum analysis received from the THz scan of the volatile compounds and/or aerosols captured in the membrane.

As anticipated, the former group fall into the healthy (Covid-19 free) group, (left of the border), using our clustering analysis, thus distinguishing Covid-19 free subjects that obviously are suspected of some illness from Covid-19 infected ones. The results of this analysis are illustrated in FIG. 8j below Spectral Signature As shown in the figures, the collected data demonstrates that healthy (Covid-19 free subjects) appear to have different spectral signature when compared with covid-19 subjects. FIG. 8k illustrates is a correlation analysis which reveals a unique spectral features to covid-19 patients. Note the peaks 450 and 920 GHz, which are unique to Covid-19 infected subjects.

Example 2

The following provides another non-limiting example as for the ability of the system and the sampler as described above to provide fast clearance detection for Coronavirus utilizing the proprietary system and the sampler and a proprietary breath testing tube (integrating a proprietary membrane) to distinguish between healthy (Covid-19 free) and infected subjects (positive to Covid-19, both symptomatic and asymptomatic).

The same test kit and equipment was used as for Example 1 described above.

A non-randomized controlled, parallel, double-blind, two-arm controlled study for validation of a breath analysis test using the analyzer discussed above was performed to detect the presence of SARS-CoV-2 VOCs in expired air samples from patients.

As a gold standard comparator method, rt-PCR was performed to identify SARS-CoV-2.

Testing was conducted at Curitiba, Parana, Brazil. Symptomatic tests were characterized based on the presence or absence of the following:

a. DATE OF THE FIRST DAY OF SIGNS OR SYMPTOMS
b. Fever
c. MAXIMUM TEMPERATURE
d. Cough
e. SORE THROAT
f. SHORTNESS OF BREATH
g. BODY PAIN
h. NASAL SECRETION
i. HEADACHE
j. NASAL OBSTRUCTION
k. Diarrhea
l. Vomit
m. LOSS OF SMELL
n. LOSS OF TASTE In addition, patient information was gathered including presence or absence of various comorbidities.

The RT-PCR sample was collected and the tube containing the collection swab was identified with the patient's unique ID label.

Next, the blow sample was collected by blowing five times in the disposable collection tube and the unique ID label of the disposable breath analyzer kit was applied to this kit and also to the tube containing the RT-PCR collection swab.

Possessing the RT-PCR collection tube, a trained health care team member scanned the barcode. Subsequently, the membrane was extracted from the disposable breathing analyzer kit and scanned for spectral analysis less than 6 hours after collection.

Sensitivity and specificity analysis was performed by the traditional 2×2 crosstable. The correlation of the two methods was evaluated through ROC analysis and determination of the correlation coefficient (r). The statistical analyses were realized with the SPSS version 17 program.

The analysis considered 2 groups of patients together or separated, with the presence or not of signs and symptoms. Thus, the patients were analyzed as:

Group 1.1—Positive, symptomatic PCR Group 1.2—Active, Negative, symptomatic PCR Group 2.1—Positive, asymptomatic PCR Group 2.2—Negative, asymptomatic PCR.

A total number of 39 patients were removed either for samples being contaminated (e.g. with saliva) or documentation impeding traceability.

The patient pool was as follows:

TABLE 3

Number of symptomatic and asymptomatic patients

|  | Patients | Positive | Negative | Total* |
|---|---|---|---|---|
| Total | N | 70 | 501 | 571 |
| % |  | 12.3% | 87.7% | 100% |
| Symptomatic | N | 53 | 183 | 236 |
| % |  | 22.5% | 77.5% | 100% |
| Asymptomatic | N | 17 | 304 | 321 |
| % |  | 5.3% | 94.7% | 100% |

*14 patients did not report whether they had or had no symptoms.

292 patients were female (51.1%), 263 males (46.1%) and 16 did not report gender (2.8%). The minimum age of the patients was 18 years and the maximum age was 89 years. The mean age was 37 years. The minimum age of symptomatic patients was 18 years and the maximum age was 78 years. The mean age was 37 years. The minimum age of asymptomatic patients was 18 years and the maximum age was 89 years. The mean age was 37 years.

From the cross tabulation between the two diagnostic methods (BAT*RT-PCR), the breath analysis test method was found to have a sensitivity of 92.86% and specificity of 96.01%. Furthermore, the positive predictive value was 76.47% and the negative predictive value was 98.97%.

TABLE 4

Results

| | | RT-PCR SARS-CoV-2 Result | | |
|---|---|---|---|---|
| | | Negative | Positive | Total |
| BAT Result | Negative | 481 | 5 | 486 |
| | Positive | 20 | 65 | 85 |
| | Total | 501 | 70 | 571 |

The area under the ROC curve was 0.944 (standard error 0.19), demonstrating the performance of the breath analysis test in detecting the presence or absence of SARS-CoV-2 in the blow samples analyzed.

Further, The samples collected for RT-PCR for SARS-CoV-2 were tested together with the viral panel of 15 other spiral viruses circulating in the Brazilian population, i.e.: Influenza A, Influenza B, Coronavirus 229E, Coronavirus NL63, Coronavirus HKU1, Coronavirus OC43, Adenovirus, Respiratory sincicial virus, Metapneumovirus, Rhinovirus, Bocavirus, Enterovirus, Parainfluenza type 1, Parainfluenza type 2, Parainfluenza type 3.

The following respiratory viruses were identified by RT-PCR: Adenovirus, Bocavirus, Other Coronavirus (Coronavirus NL63 and Coronavirus HKU1) and Rhinovirus

TABLE 5

Other Respiratory Viruses

| Virus | Frequency | % | % cumulative |
|---|---|---|---|
|  | 539 | 94.4 | 94.4 |
| Adenovirus | 1 | 0.2 | 94.6 |
| Bocavirus | 2 | 0.4 | 94.9 |
| Other coronavirus | 6 | 1.1 | 96.0 |
| Rhinovirus | 23 | 4.0 | 100.0 |
| Total | 571 | 100.0 |  |

For all cases in which RT-PCR was positive for Adenovirus, Bocavirus Coronavirus NL63 and Coronavirus HKU1, BAT showed a negative result for SARS-CoV-2.

Only in one case of RRT-PCR positive for Rhinovirus, the breath analysis tested positive for SARS-CoV-2.

The results indicate a general accuracy of 94.4% (99% CI: 89.7 to 99.2%) symptomatic and asymptomatic patients. In this population, the sensitivity and specificity of the method were 92.86% and 96.01%, respectively. With 12.3% positivity of the samples, the negative predictive value of the method was 98.97% and the positive predictive value was 76.47%.

While certain embodiments have been described, these embodiments have been presented by way of example only, and are not intended to limit the scope of the inventions. Indeed, the novel embodiments described herein may be embodied in a variety of other forms. Furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A high throughput system for label-free, noncontact, noninvasive, and nondestructive detection of at least one virus infected or virus free individual from at least one tested individual, the system comprising:
at least one sampler comprising at least one metamaterial membrane absorber located at a propagation path of collected media being selected from a group consisting of an aerosol, any airborne compound, a volatile compound, and any combination thereof, released by the breath of said at least one tested individual, said metamaterial membrane absorber being configured to trap the collected media; and
a controller configured to receive data indicative of the collected media being scanned with electromagnetic radiation in the THz range and processing said data for identifying a signature being indicative of virus infected or virus free individuals to thereby provide detection of said virus infected or virus free individuals.

2. The system of claim 1, wherein said sampler comprises a proximal end and a distal end interconnected by a main longitudinal axis, along which said at least one metamaterial membrane is positioned; and into which the breath of said tested individual is exhaled, such that the propagation paths of said exhaled breath and said collected media therewithin intersect said at least one metamaterial membrane and is absorbed therewithin.

3. The system of claim 1, wherein said system is configured to distinguish between a healthy individual, a virus recovered individual and an infected individual.

4. The system of claim 1, wherein said virus is selected from a group consisting of: a family of coronaviruses, COVID-19, influenza, avian influenza or any combination thereof.

5. The system of claim 1, wherein said at least one metamaterial membrane and/or said sampler is placed in an electromagnetic tester, said electromagnetic tester configured to be in communication with (a) a THz generator adapted to generate THz frequencies, and (b) a THz scanner comprising at least two photomixers.

6. The system of claim 5, wherein among the at least two photomixers comprising a first photomixer is configured to transmit a THz signal and a second photomixer is configured to receive the transmitted THz signal.

7. The system of claim 5, wherein the tester is configured to (a) scan in the THz range said metamaterial membrane absorbed with said media in said exhaled breath of said tested individual and (b) transmit data indicative of the collected media to said controller.

8. The system of claim 1, wherein said sampler is RFID tagged with each of said tested individual, such that detection of said virus infected or virus free individuals is traced back to each of said tested individual.

9. The system of claim 1, wherein the controller is configured to perform pattern recognition on at least one absorption spectrum of said membrane.

10. The system of claim 1, wherein said controller is configured to perform a learning phase using a machine learning model to detect at least one parameter in an absorption spectrum of said membrane, with said collected media being scanned with the electromagnetic radiation in the THz range.

11. The system of claim 1, wherein the membrane absorber is made of at least one material selected from the group consisting of a meta-material membrane, a semi pressure permeable membrane, a meta-material, PET, open-cell foam-based melamine or any combination thereof.

12. The system of claim 1, wherein the at least one sampler is made of polyoxymethylene-based material.

13. The system of claim 1, wherein the system is configured to be utilized in at least one public place selected from the group consisting of airports, schools, public clinics, convention centers, parks, kindergartens, stadiums or any combination thereof.

14. The system of claim 1, wherein the THz range is between 200 GHz to 1200 GHz.

15. The system of claim 1, wherein the signature comprises information indicative of said virus; said information being selected from a group consisting of cell unit of said virus, viral proteins, cellular debris, debris of said virus, hydrates of said virus, hydrates of debris of said virus, hydrates of the 3D structure of said virus and a cell, aggregates of said virus, cytokines, increased level of interleukin interleukin IL-7, interleukin-2 receptor (IL-2R), interleukin-6 (IL-6), granulocytecolony, stimulating factor, interferon-y, inducible protein 10, monocyte chemoattractant, protein 1, macrophage, inflammatory protein 1-a, and tumor necrosis factor-a, and any combination thereof.

16. The system of claim 1, wherein the membrane is coated with at least one material selected from a group consisting of silicon, silicon graphene or any combination thereof.

17. The system of claim 1, wherein the controller is configured to operate in modes including (a) a learning phase and (b) a detection phase, wherein:
  (a) in said learning phase, said controller trains a machine learning model to detect at least one parameter in the absorption spectrum of said membrane with said collected media being scanned with an electromagnetic radiation in the THz range of a plurality of membrane stored in said communicable and readable database in order to generate information data being indicative of said virus infected individuals, wherein
    (i) said parameter is selected from a group consisting of, trends in said database of said at least one tested individuals, eigenvector of said database of said at least one tested individuals, eigenvalues of said database of said at least one tested individuals, feature extraction step being configured to estimate the most relevant vectors defining the data using a principal component analysis, a pattern classification using a combined linear and nonlinear pattern recognition approach, known symptoms of said virus, known healthy individuals, healthy individual vital signs selected from fever, sweat, body temperature, blood pressure, pulse (heart rate), and breathing rate (respiratory rate) and any combination thereof, infected individual vital signs selected from fever, sweat, body temperature, blood pressure, pulse (heart rate), and breathing rate (respiratory rate) and any combination thereof, medicaments being administered to said tested individual, and any combination thereof,
    (ii) in said learning phase, said data is either supervised or unsupervised data; and, said training by said controller is performed by at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected media being scanned with an electromagnetic radiation in the THz range stored in said communicable and readable database in order to generate information data being indicative of at least one said virus infected individuals, and
  (b) in said detection phase, said data is either supervised or unsupervised data; and, said controller performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected media being scanned with an electromagnetic radiation in the THz range stored in said communicable and readable database in order to generate information data being indicative of at least one said virus infected individuals.

18. The system of claim 1, additionally comprising at least one communicable and readable database storing instructions which, when executed by at least one processor, cause the controller to perform operations comprising:
  training a machine learning model to detect at least one parameter of said collected media being scanned with an electromagnetic radiation in the THz range of at least one tested individuals stored in said communicable and readable database in order to generate information data being indicative of said virus infected individuals; and
  after said step of training, real time detecting said parameter by means of said trained machine learning model, wherein said data is either supervised or unsupervised data; and, said controller performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof in order to generate information data being indicative of said virus infected individuals.

19. The system of claim 1, wherein the controller is further configured to perform fast Fourier transformations in order to generate information data being indicative of said virus infected individuals.

20. The system of claim 1, wherein the collected media is at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-lcyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, NO2 and any combination thereof.

21. A high throughput method for label-free, noncontact, noninvasive, and nondestructive detection of at least one virus infected or virus free individual from at least one tested individual, the method comprising:
  receiving data indicative of a collected media being selected from a group consisting of aerosol, any airborne compound, volatile compounds, VCs, and any combination thereof, being scanned with electromagnetic radiation in the THz range; and
  processing said data for identifying a signature being indicative of said virus infected or virus free individuals.

22. The method of claim 21, wherein said THz range is between 200 GHz to 1200 GHz.

23. The method of claim 21, wherein said tested individual is asymptomatic.

24. The method of claim 21, wherein detection of said virus free individuals provides clearance to healthy individuals and/or virus recovered individuals.

25. The method of claim 21, wherein said signature is information indicative of said virus; said information being selected from a group consisting of cell unit of said virus, viral proteins, cellular debris, debris of said virus, hydrates of said virus, hydrates of debris of said virus, hydrates of the 3D structure of said virus and a cell, aggregates of said virus, cytokines, increased level of interleukin interleukin IL-7, interleukin-2 receptor (IL-2R), interleukin-6 (IL-6), granulocytecolony, stimulating factor, interferon-y, inducible protein 10, monocyte chemoattractant, protein 1, macrophage, inflammatory protein 1-a, and tumor necrosis factor-a, and any combination thereof.

26. The method of claim 21, wherein said processing comprises performing a pattern recognition of said signature.

27. A sampler to be integrated into a system for label-free, noncontact, noninvasive, and nondestructive detection of at least one virus infected or virus free individuals from at least one tested individual, the sampler comprising:
a proximal end and a distal end interconnected by a longitudinal axis, and
at least one metamaterial membrane positioned along the longitudinal axis and configured to receive the exhaled breath of said tested individual, such that a propagation path of said exhaled breath and collected media therewithin intersect said at least one metamaterial membrane; said metamaterial membrane being configured and operable for trapping said collected media, said collected media being selected from a group consisting of aerosol, any airborne compound, volatile compounds, VCs, and any combination thereof.

28. The sampler of claim 27, wherein said system additionally comprising a controller configured to receive data indicative of said collected media being scanned with an electromagnetic radiation in the THz range and to process said data for identifying a signature being indicative of virus infected or virus free individuals, to thereby provide detection of said virus infected or virus free individuals.

29. The sampler of claim 27, wherein said sampler is configured to be sealed airtight such that said collected media released by said at least one tested individual's breath is prevented from exiting said sampler.

30. The sampler of claim 27, wherein said sampler comprises two parts reversibly coupled to each other along a main longitudinal axis, such that (a) said at least one metamaterial membrane is positioned therebetween along said main longitudinal axis; and (b) into said sampler the breath of said tested individual is exhaled, such that propagation paths of said exhaled breath and said collected media therewithin intersect said at least one metamaterial membrane.

31. The sampler of claim 27, wherein the membrane is made of at least one material selected from the group consisting of a meta-material membrane, a semi pressure permeable membrane, a meta-material, PET, open-cell foam-based melamine or any combination thereof.

32. The sampler of claim 27, wherein the sampler is made of polyoxymethylene-based material.

33. The sampler of claim 27, wherein the system is configured to be utilized in at least one public place selected from the group consisting of airports, schools, public clinics, convention centers, parks, kindergartens, stadiums or any combination thereof.

34. The sampler of claim 28, wherein the THz range is between 200 GHz to 1200 GHz.

35. The sampler of claim 28, wherein the signature comprises information indicative of said virus; said information being selected from a group consisting of cell unit of said virus, viral proteins, cellular debris, debris of said virus, hydrates of said virus, hydrates of debris of said virus, hydrates of the 3D structure of said virus and a cell, aggregates of said virus, cytokines, increased level of interleukin interleukin IL-7, interleukin-2 receptor (IL-2R), interleukin-6 (IL-6), granulocytecolony, stimulating factor, interferon-y, inducible protein 10, monocyte chemoattractant, protein 1, macrophage, inflammatory protein 1-a, and tumor necrosis factor-a, and any combination thereof.

36. The sampler of claim 27, wherein the membrane is coated with at least one material selected from a group consisting of silicon, silicon graphene or any combination thereof.

37. The sampler of claim 28, wherein the controller is configured to operate in modes including (a) a learning phase and (b) a detection phase, wherein:
(a) in said learning phase, said controller trains a machine learning model to detect at least one parameter in the absorption spectrum of said membrane with said collected media being scanned with an electromagnetic radiation in the THz range of a plurality of membrane stored in said communicable and readable database in order to generate information data being indicative of said virus infected individuals, wherein
(i) said parameter is selected from a group consisting of, trends in said database of said at least one tested individuals, eigenvector of said database of said at least one tested individuals, eigenvalues of said database of said at least one tested individuals, feature extraction step being configured to estimate the most relevant vectors defining the data using a principal component analysis, a pattern classification using a combined linear and nonlinear pattern recognition approach, known symptoms of said virus, known healthy individuals, healthy individual vital signs selected from fever, sweat, body temperature, blood pressure, pulse (heart rate), and breathing rate (respiratory rate) and any combination thereof, infected individual vital signs selected from fever, sweat, body temperature, blood pressure, pulse (heart rate), and breathing rate (respiratory rate) and any combination thereof, medicaments being administered to said tested individual, and any combination thereof,
(ii) in said learning phase, said data is either supervised or unsupervised data; and, said training by said controller is performed by at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected media being scanned with an electromagnetic radiation in the THz range stored in said communicable and readable database in order to generate information data being indicative of at least one said virus infected individuals, and
(b) in said detection phase, said data is either supervised or unsupervised data; and, said controller performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof on said collected media being scanned with an electromagnetic radiation in the THz range stored in said communicable and readable database in order to generate information data being indicative of at least one said virus infected individuals.

38. The sampler of claim 28, wherein the controller is configured to be communicated with a database storing instructions which, when executed, cause the controller to perform operations comprising:

training a machine learning model to detect at least one parameter of said collected media being scanned with an electromagnetic radiation in the THz range of at least one tested individuals stored in said communicable and readable database in order to generate information data being indicative of said virus infected individuals; and after said step of training, real time detecting said parameter by means of said trained machine learning model, wherein said data is either supervised or unsupervised data; and, said controller performs at least one algorithm selected from a group consisting of Leave One Out (LOO) algorithm, Principal Component Analysis algorithm, canberra distance, k-nearest neighbors algorithm, Quadrature, Fisher's linear discriminant, Fisher's nonlinear discriminant, Network Acceleration algorithm (NNA), any machine learning algorithm and any combination thereof in order to generate information data being indicative of said virus infected individuals.

39. The sampler of claim 28, wherein the controller is further configured to perform fast Fourier transformations in order to generate information data being indicative of said virus infected individuals.

40. The sampler of claim 27, wherein the collected media is at least one selected from a group consisting of organic compound, inorganic compound, mixture thereof, Ketones, aromatic alcohols, aldehydes, 1-butanol, dimethyl disulfide, methyl benzene, hexanal, phenylethane, heptanal, benzaldehyde, dimethyl trisulfide, phenol, 2-(2-ethoxyethoxy)ethanol, 2-ethyl-1-hexanol, 5-isopropenyl-1-methyl-1cyclohexene, acetophenone, 2-nonanone, 2-decanone, 2-isopropylphenol, benzothiazole, 2-undecanone, 1,3-diacetylbenzene, diethyl phthalate, 1,3-diphenyl propane, Ammonia, Greenhouse gases selected from Water vapor Methane ($CH_4$), Carbon dioxide ($CO_2$), Nitrous oxide ($N_2O$), Ozone ($O_3$), Chlorofluorocarbons (CFCs), Hydrofluorocarbons (includes HCFCs and HFCs), NO, NO2 and any combination thereof.

* * * * *